(12) United States Patent
Sindkhedkar et al.

(10) Patent No.: US 8,097,594 B2
(45) Date of Patent: Jan. 17, 2012

(54) MACROLIDES AND KETOLIDES HAVING ANTIMICROBIAL ACTIVITY

(75) Inventors: Milind Dattatraya Sindkhedkar, Pune (IN); Vijaya Narayan Desai, Pune (IN); Rajesh Maganlal Loriya, Rajkot (IN); Mahesh Vithalbhai Patel, Aurangabad (IN); Bharat Kalidas Trivedi, Aurangabad (IN); Rajesh Onkardas Bora, Aurangabad (IN); Santosh Devidas Diwakar, Ahmednagar (IN); Ganesh Rajaram Jadhav, Solapur (IN); Shivaji Sampatrao Pawar, Aurangabad (IN)

(73) Assignee: Wockhardt Ltd., Bandra-Kurla Complex, Bandra East, Mumbai (IN)

( * ) Notice: Subject to any disclaimer, the term of this patent is extended or adjusted under 35 U.S.C. 154(b) by 431 days.

(21) Appl. No.: 12/379,539

(22) Filed: Feb. 24, 2009

(65) Prior Publication Data

US 2009/0247478 A1 Oct. 1, 2009

Related U.S. Application Data

(63) Continuation-in-part of application No. PCT/IB2007/002405, filed on Aug. 22, 2007.

(30) Foreign Application Priority Data

Aug. 24, 2006 (IN) .......................... 1336/MUM/2006

(51) Int. Cl.
*A61K 31/70* (2006.01)
*C07H 17/08* (2006.01)
(52) U.S. Cl. ........................................... 514/29; 536/7.4
(58) Field of Classification Search .................... 536/7.4
See application file for complete search history.

(56) References Cited

U.S. PATENT DOCUMENTS 7,524,823 B2 * 4/2009 Kellenberger et al. .......... 514/29

* cited by examiner

*Primary Examiner* — Elli Peselev
(74) *Attorney, Agent, or Firm* — Bio Intellectual Property Services (Bio IPS) LLC; O. (Sam) Zaghmout

(57) ABSTRACT

The present invention provides compounds having antimicrobial activity for preventing and treating diseases caused by microbial infections. Thus, the present invention relates to novel semi-synthetic 11,12-γ lactone macrolides and ketolides having antimicrobial activity, processes for making compounds as well as pharmaceutical compositions containing said compounds as active ingredients and methods of treating microbial infections with the compounds.

18 Claims, No Drawings

MACROLIDES AND KETOLIDES HAVING ANTIMICROBIAL ACTIVITY

CROSS-REFERENCE TO RELATED APPLICATIONS

This application is a continuation-in-part of Application No. PCT/IB2007/002405, filed Aug. 22, 2007, published in English, which claims benefit of an Indian patent application No. 1336/MUM/2006, filed Aug. 24, 2006. The entire disclosure of these prior applications are hereby incorporated by reference.

STATEMENT REGARDING FEDERALLY SPONSORED RESEARCH OR DEVELOPMENT

This invention has been created without the sponsorship or funding of any federally sponsored research or development program.

FIELD OF THE INVENTION

The present invention relates to novel 11,12-γ lactone macrolides and ketolides having antimicrobial activity, pharmaceutical compositions containing the compounds and methods of treating microbial infections with the compounds.

BACKGROUND OF THE INVENTION

Macrolides are a well-known family of antimicrobial agents, erythromycin A, 14-membered macrolide, was isolated in 1952 from *Streptomyces erythraeus*. Examples of macrolides being used as therapeutic agents are roxithromycin, clarithromycin and azithromycin (azalide). Ketolides are semisynthetic 14-membered ring macrolide derivatives, characterized by the presence of a keto function at position 3 instead of L-cladinose moiety present in the macrolactone ring. Telithromycin and Cethromycin are examples of ketolides.

U.S. Pat. No. 4,331,803 discloses the 6-O-methyl derivative of erythromycin i.e. clarithromycin. The U.S. Pat. No. 4,349,545 discloses roxithromycin. The azalide azithromycin is disclosed in U.S. Pat. No. 4,517,359. Telithromycin is described in EP 680967 A1 and corresponding U.S. Pat. No. 5,635,485 and *Bioorg. Med. Chem. Lett.* 1999, 9(21), 3075-3080. Another ketolide Cethromycin (ABT 773) is disclosed in WO 98/09978, and *J. Med. Chem.* 2000, 43, 1045.

The U.S. Pat. No. 6,900,183 describes 11,12-γ lactone ketolides having C-21 of the lactone substituted with cyano or amino derivatives.

The patent application US 2004/0077557 and PCT publications WO 02/16380, WO 03/42228 WO 04/16634 and WO 03/072588 discloses 11,12-γ lactone ketolides.

DESCRIPTION OF THE INVENTION

In one general aspect there is provided macrolide and ketolide compounds of Formula I

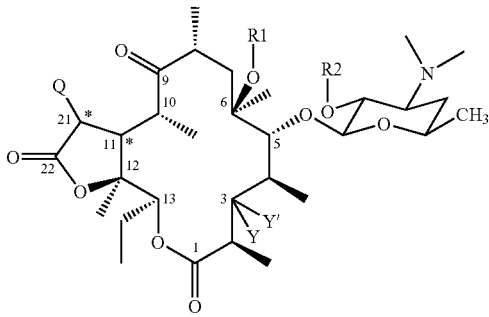

Formula I and their pharmaceutically acceptable salts, pharmaceutically acceptable solvates, polymorphs, enantiomers or diastereomers, wherein
* indicates a chiral center;
$R_1$ is hydrogen or methyl;
$R_2$ is hydrogen or hydroxyl protecting group,
wherein hydroxyl protecting groups are selected from the group consisting of triethylsilyl, trimethylsilyl, acetyl, benzoyl, methoxymethyl, benzyl, methoxyethoxymethyl or tertbutyldimethylsilyl;
Q is Het or

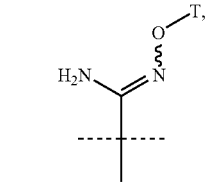

wherein
Het is selected from

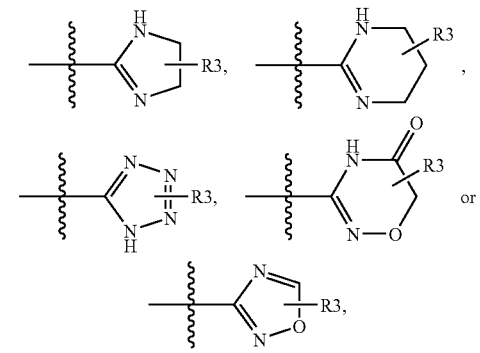

wherein $R_3$ is one or more substituent selected from the group consisting of $NO_2$, CN, halogen, $C_1$-$C_6$ alkyl, $C_2$-$C_6$ alkenyl, $CH_2CONH_2$, $CH_2CO_2Et$, $CH_2CN$, $CH_2CH_2OH$, $CH_2OCH_2CH_2OCH_3$, $NH_2$, substituted $C_1$-$C_6$ alkyl and substituted $C_2$-$C_6$ alkenyl;
T is selected from the group consisting of:
hydrogen, —$(CH_2)_m$—$R_5$, —$(CH_2)_m$—CH═CH—$R_5$, —$(CH_2)_m$—C≡C—$R_5$, -A-$(CH_2)_m$—$R_5$, -A-$(CH_2)_m$—CH═CH—$R_5$, -A-$(CH_2)_m$—C≡C—$R_5$, —$(CH_2)_m$—B—$R_5$, -A-$(CH_2)_m$—B—$R_5$, —(CH$_2$)$_m$—X—R$_6$, —(CH$_2$)$_m$—B—X—R$_6$, —(CH$_2$)$_m$—CH═CH—X—R$_6$, —(CH$_2$)$_m$—C≡C—X—R$_6$, -A-(CH$_2$)$_m$—X—R$_6$, -A-(CH$_2$)$_m$—B—X—R$_6$, -A-(CH$_2$)$_m$—CH═CH—X—R$_6$ and -A-(CH$_2$)$_m$—C≡C—X—R$_6$;

wherein, m is 0, 1, 2 or 3;

R$_5$ is selected from the group consisting of:
hydrogen, cyano, halogen, hydroxyl, CO$_2$(C$_1$-C$_6$ alkyl), CO NR$_a$R$_b$, NR$_a$R$_b$, C$_1$-C$_6$ alkyl or substituted C$_1$-C$_6$ alkyl, C$_2$-C$_6$ alkenyl or substituted C$_2$-C$_6$ alkenyl, C$_2$-C$_6$ alkynyl or substituted C$_2$-C$_6$ alkynyl, 6 membered substituted or unsubstituted aryl, 5-6 membered substituted or unsubstituted heteroaryl, 3-6 membered substituted or unsubstituted cycloalkyl and 3-6 membered substituted or unsubstituted heterocyclyl; wherein R$_a$ and R$_b$ are independently hydrogen, C$_1$-C$_6$ alkyl or R$_a$ and R$_b$ together with the nitrogen to which they are attached form a 5-6 membered heterocyclic ring wherein the heterocycle has one or more heteroatoms selected from N, O, S;

A is —CO— or —CONH—;

B is —O—, —S—, —SO—, —SO$_2$—, —CO—, —CONH—, —CON(CH$_3$)—, —NHCONH—, —C(NH$_2$)═N—O—,

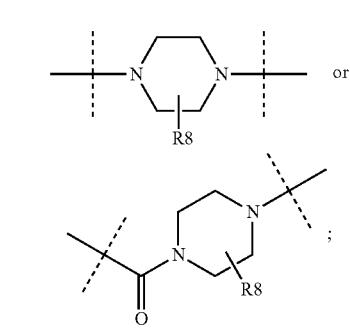

wherein

R$_8$ is a substitutent at any one of carbon of the heterocycle, R$_8$ is selected from the group comprising of hydrogen, C$_1$-C$_6$ alkyl, substituted C$_1$-C$_6$ alkyl, C$_2$-C$_6$ alkenyl and substituted C$_2$-C$_6$ alkenyl;

X is a 6 membered aryl or a 5-6 membered heteroaryl;

R$_6$ is aryl, heteroaryl, substituted aryl or substituted heteroaryl;

Y' is hydrogen and Y is OR$_7$, wherein R$_7$ is hydrogen or

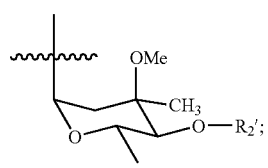

wherein R$_2$ is hydrogen, (when R$_2$ is hydrogen, R$_7$ is designated as cladinose) or hydroxyl protecting group, wherein hydroxyl protecting groups are selected from the group consisting of triethylsilyl, trimethylsilyl, acetyl, benzoyl, methoxymethyl, methoxyethoxymethyl, benzyl or tertbutyldimethylsilyl;

or

Y and Y' together with the carbon to which they are attached form C═O.

In one embodiment there is provided macrolide compound of Formula I-a, wherein,

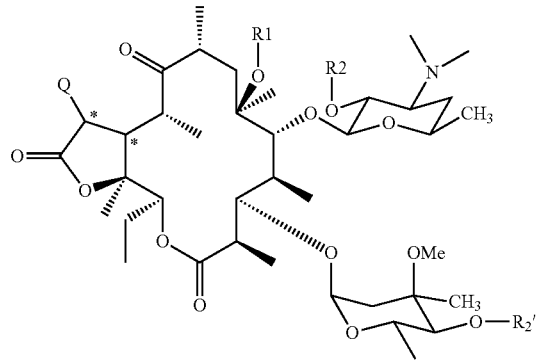

Formula I-a wherein Q, R$_1$, R$_2$ and R$_{2'}$ are as defined above.

Another embodiment relates to macrolide compound of Formula I-b,

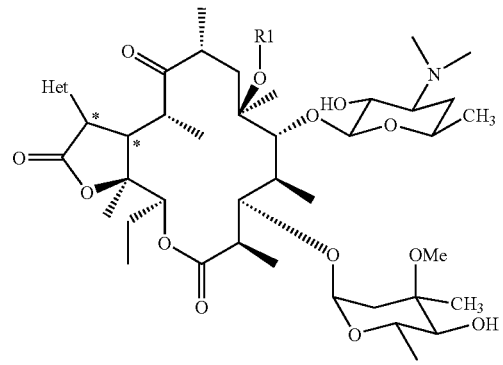

Formula I-b wherein R$_1$ and Het are as defined above.

Another embodiment relates to compound of Formula I-c,

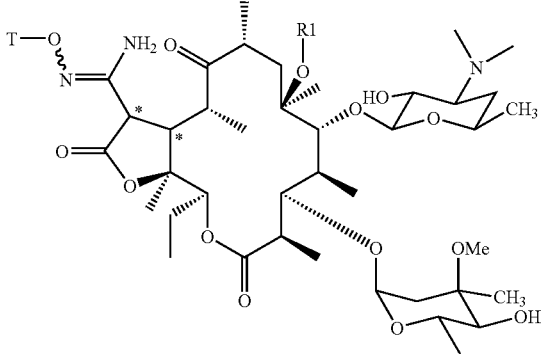

Formula I-c wherein T and R$_1$ are as defined above.

Another embodiment relates to ketolide compound of Formula I-d,

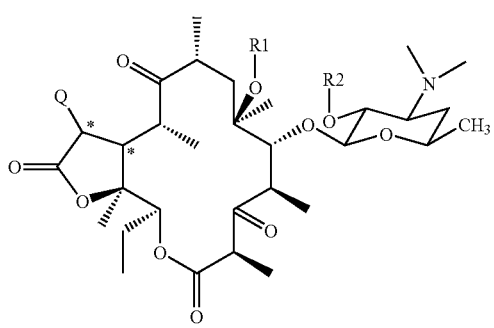

Formula I-d wherein $R_1$ is $CH_3$, $R_2$ and Q are as defined above.

Another embodiment relates to ketolide compound of the invention of Formula I-e,

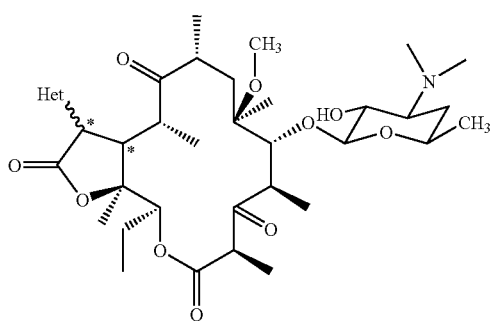

Formula I-e wherein Het is as defined above.

Another embodiment relates to ketolide compound of Formula I-f,

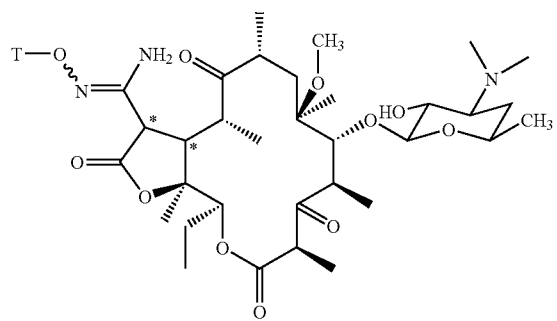

Formula I-f wherein T is as defined above.

Another embodiment relates to pharmaceutical compositions of compounds of Formula I and their pharmaceutically acceptable salts, pharmaceutically acceptable solvates, polymorphs, enantiomers or diastereomers, together with one or more pharmaceutically acceptable carriers, excipients or diluents, for the treatment and prevention of a microbial infection in human or animal.

In another embodiment the compounds of Formula I and their pharmaceutically acceptable salts, pharmaceutically acceptable solvates, polymorphs, enantiomers or diastereomers.

Yet another embodiment is also directed to a method of treating a subject having a condition caused by or contributed to by microbial infection, which comprises administering to the said subject a therapeutically effective amount of compound of Formula I and their pharmaceutically acceptable salts, pharmaceutically acceptable solvates, polymorphs, enantiomers or diastereomers.

Another embodiment is further directed to a method of preventing a subject from suffering from a condition caused by or contributed to by microbial infection, which comprises administering to the subject a prophylactically effective amount of compound of Formula I and their pharmaceutically acceptable salts, pharmaceutically acceptable solvates, polymorphs, enantiomers or diastereomers.

Another embodiment relates to method of preparation of the compounds of Formula I and their pharmaceutically acceptable salts, pharmaceutically acceptable solvates, polymorphs, enantiomers or diastereomers.

Other objects and advantages will become apparent to those skilled in the art from a review of the ensuing specification.

Representative compounds of the invention are

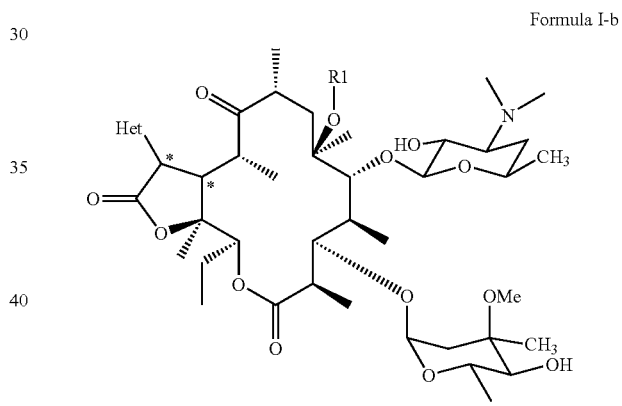

Formula I-b

Compound of Formula I-b where Het is 1H-tetrazol-5-yl, $R_1$ is $CH_3$;
Compound of Formula I-b where Het is 2-(2-methoxyethoxymethyl)-2H-tetrazol-5-yl, $R_1$ is $CH_3$;
Compound of Formula I-b where Het is 1-(2-methoxyethoxymethyl)-2H-tetrazol-5-yl, $R_1$ is $CH_3$;
Compound of Formula I-b where Het is 2-(ethoxycarbonylmethyl)-2H-tetrazol-5-yl, $R_1$ is $CH_3$;
Compound of Formula I-b where Het is 1-(ethoxycarbonylmethyl)-2H-tetrazol-5-yl, $R_1$ is $CH_3$;
Compound of Formula I-b where Het is 2-(carbamoylmethyl)-2H-tetrazol-5-yl, $R_1$ is $CH_3$;
Compound of Formula I-b where Het is 1-(carbamoylmethyl)-2H-tetrazol-5-yl, $R_1$ is $CH_3$;
Compound of Formula I-b where Het is 2-(cyanomethyl)-2H-tetrazol-5-yl, $R_1$ is $CH_3$;
Compound of Formula I-b where Het is 1-(cyanomethyl)-2H-tetrazol-5-yl, $R_1$ is $CH_3$;
Compound of Formula I-b where Het is 2-(allyl)-2H-tetrazol-5-yl, $R_1$ is $CH_3$;
Compound of Formula I-b where Het is 1-(allyl)-2H-tetrazol-5-yl, $R_1$ is $CH_3$;

Compound of Formula I-b where Het is 2-(hydroxyethyl)-2H-tetrazol-5-yl, $R_1$ is $CH_3$;
Compound of Formula I-b where Het is 1-(hydroxyethyl)-2H-tetrazol-5-yl, $R_1$ is $CH_3$;
Compound of Formula I-b where Het is 2-(carboxylic acid (3-fluoro-phenyl)-methylamide)-2H-tetrazol-5-yl, $R_1$ is $CH_3$;
Compound of Formula I-b where Het is 5-methyl-[1,2,4]oxadiazol-3-yl, $R_1$ is $CH_3$;
Compound of Formula I-b where Het is 4,5-dihydro-1H-imidazol-2-yl, $R_1$ is $CH_3$;
Compound of Formula I-b where Het is 1,4,5,6-tetrahydro-pyrimidin-2-yl, $R_1$ is $CH_3$;

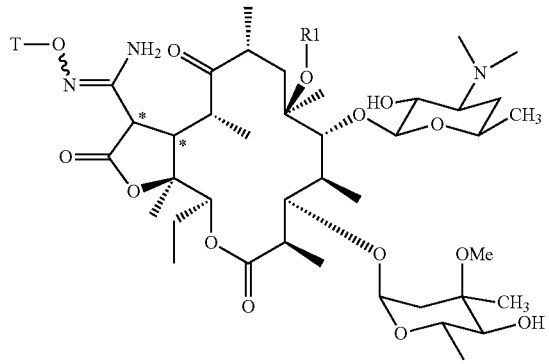

Formula I-c

Compound of Formula I-c where T is H, $R_1$ is $CH_3$;
Compound of Formula I-c where T is $CO(CH_2)_2$-(pyridin-3-yl), $R_1$ is $CH_3$;
Compound of Formula I-c where T is $COCH_2O$-(2-chlorophenyl), $R_1$ is $CH_3$;
Compound of Formula I-c where T is $CO(CH_2)_2$-(4-dimethylamino)phenyl, $R_1$ is $CH_3$;
Compound of Formula I-c where T is CO-(pyridin-3-yl), $R_1$ is $CH_3$;
Compound of Formula I-c where T is $CO(CH_2)_2$-(pyridin-4-yl), $R_1$ is $CH_3$;
Compound of Formula I-c where T is $CO(CH_2)_2$-(3-methoxy)phenyl, $R_1$ is $CH_3$;
Compound of Formula I-c where T is $CO(CH_2)_2$-(4-methoxy)phenyl, $R_1$ is $CH_3$;
Compound of Formula I-c where T is $CO(CH_2)_2$-(3-cyano)phenyl, $R_1$ is $CH_3$;
Compound of Formula I-c where T is $CO(CH_2)_2$-(4-cyano)phenyl, $R_1$ is $CH_3$;
Compound of Formula I-c where T is $COCH_2O$-(3-chloro)phenyl, $R_1$ is $CH_3$;
Compound of Formula I-c where T is $CO(CH_2)_2$-(3,5-dimethoxy)phenyl, $R_1$ is $CH_3$;
Compound of Formula I-c where T is $CO(CH_2)_2$-(2,3-dimethoxy)phenyl, $R_1$ is $CH_3$;
Compound of Formula I-c where T is $CO(CH_2)_2$-(2,5-dimethoxy)phenyl, $R_1$ is $CH_3$;
Compound of Formula I-c where T is $CO(CH_2)_2$-(3-fluoro)phenyl, $R_1$ is $CH_3$;
Compound of Formula I-c where T is $CO(CH_2)_2$-(4-trifluoromethyl)phenyl, $R_1$ is $CH_3$;
Compound of Formula I-c where T is $CO(CH_2)_2$-(4-(4-methyl-piperazine)phenyl), $R_1$ is $CH_3$;
Compound of Formula I-c where T is $CO(CH_2)_2$-(4-(2-methylphenyl)-piperazinyl), $R_1$ is $CH_3$;
Compound of Formula I-c where T is $CO(CH_2)_2$-(4-(2-methoxyphenyl)-piperazinyl), $R_1$ is $CH_3$;
Compound of Formula I-c where T is $CO(CH_2)_2$-(4-(3-methoxyphenyl)-piperazinyl), $R_1$ is $CH_3$;
Compound of Formula I-c where T is $CO(CH_2)_2$-(4-(2-fluorophenyl)-piperazinyl), $R_1$ is $CH_3$;
Compound of Formula I-c where T is $CO(CH_2)_2$-(4-(pyrimidin-2-yl)-piperazinyl), $R_1$ is $CH_3$;
Compound of Formula I-c where T is $CO(CH_2)_2$-(4-(pyridin-2-yl)-piperazinyl), $R_1$ is $CH_3$;
Compound of Formula I-c where T is $COCH_2O$-phenyl, $R_1$ is $CH_3$;
Compound of Formula I-c where T is $COCH_2O$-(2-methylphenyl), $R_1$ is $CH_3$;
Compound of Formula I-c where T is $COCH_2O$-(3-methylphenyl), $R_1$ is $CH_3$;
Compound of Formula I-c where T is $COCH_2O$-(4-methylphenyl), $R_1$ is $CH_3$;
Compound of Formula I-c where T is $COCH_2O$-(2-methoxyphenyl), $R_1$ is $CH_3$;
Compound of Formula I-c where T is $COCH_2O$-(4-methoxyphenyl), $R_1$ is $CH_3$;
Compound of Formula I-c where T is $COCH_2O$-(2,3,4,5,6-pentafluorophenyl), $R_1$ is $CH_3$;
Compound of Formula I-c where T is $COCH_2O$-(4-cyanophenyl), $R_1$ is $CH_3$;
Compound of Formula I-c where T is $CO(CH_2)_2$-(4-(phenyl)piperazinyl), $R_1$ is $CH_3$;
Compound of Formula I-c where T is $COCH_2S$-phenyl, $R_1$ is $CH_3$;
Compound of Formula I-c where T is $COCH_2S$-(4-fluorophenyl), $R_1$ is $CH_3$;
Compound of Formula I-c where T is $COCH_2S$-(2-fluorophenyl), $R_1$ is $CH_3$;
Compound of Formula I-c where T is $COCH_2S$-(3-fluorophenyl), $R_1$ is $CH_3$;
Compound of Formula I-c where T is $COCH_2S$-(3-methoxyphenyl), $R_1$ is $CH_3$;
Compound of Formula I-c where T is $CO(CH_2)_2$-(4-([1,2,3]-triazol-1-yl)phenyl), $R_1$ is $CH_3$;
Compound of Formula I-c where T is $CO(CH_2)_2$-(4-(imidazol-1-yl)phenyl), $R_1$ is $CH_3$;
Compound of Formula I-c where T is $CO(CH_2)_2$-(4-([1,2,4]-triazol-1-yl)phenyl), $R_1$ is $CH_3$;
Compound of Formula I-c where T is $CO(CH_2)_2$-(4-(4-acetyl-[1,2,3]triazol-1-yl))-phenyl, $R_1$ is $CH_3$;
Compound of Formula I-c where T is $CO(CH_2)_2$-(4-(4-cyano-[1,2,4]-triazol-1-yl)phenyl), $R_1$ is $CH_3$;
Compound of Formula I-c where T is $CO(CH_2)_2$-(benzo[1,3]dioxol-5-yl), $R_1$ is $CH_3$;
Compound of Formula I-c where T is $COCH_2$-(benzo[1,3]dioxol-5-yl), $R_1$ is $CH_3$;
Compound of Formula I-c where T is $CO(CH_2)_2$-(1-(4-methoxyphenyl)-1H-[1,2,3]triazol-4-yl), $R_1$ is $CH_3$;
Compound of Formula I-c where T is $CO(CH_2)_2$-(1-(pyridin-3-yl)-1H-[1,2,3]triazol-4-yl), $R_1$ is $CH_3$;
Compound of Formula I-c where T is $CO(CH_2)_2$-(1-(4-fluorophenyl)-1H-[1,2,3]triazol-4-yl), $R_1$ is $CH_3$;
Compound of Formula I-c where T is $CO(CH_2)_2$-(1-(3-methylphenyl)-1H-[1,2,3]triazol-4-yl), $R_1$ is $CH_3$;
Compound of Formula I-c where T is $CO(CH_2)_2$-(1-(3-chlorophenyl)-1H-[1,2,3]triazol-4-yl), $R_1$ is $CH_3$;
Compound of Formula I-c where T is $CO(CH_2)_2$-(1-(2-fluorophenyl)-1H-[1,2,3]triazol-4-yl), $R_1$ is $CH_3$;
Compound of Formula I-c where T is $CO(CH_2)_2$-(1-(2,4-difluorophenyl)-1H-[1,2,3]triazol-4-yl), $R_1$ is $CH_3$;

Compound of Formula I-c where T is CO(CH$_2$)$_2$-(1-(3,4-difluorophenyl)-1H-[1,2,3]triazol-4-yl), R$_1$ is CH$_3$;
Compound of Formula I-c where T is CO(CH$_2$)$_2$-(1-(2,3,4-trifluorophenyl)-1H-[1,2,3]triazol-4-yl), R$_1$ is CH$_3$;
Compound of Formula I-c where T is CO(CH$_2$)$_2$-(1-(2-fluoro-4-methyl-phenyl)-1H-[1,2,3]triazol-4-yl), R$_1$ is CH$_3$;
Compound of Formula I-c where T is CO(CH$_2$)$_2$-(1-(2-fluoro-4-methoxy-phenyl)-1H-[1,2,3]triazol-4-yl), R$_1$ is CH$_3$;
Compound of Formula I-c where T is CO(CH$_2$)$_2$-(1-(2,3-difluoro-4-ethoxy-phenyl)-1H-[1,2,3]triazol-4-yl), R$_1$ is CH$_3$;
Compound of Formula I-c where T is CO(CH$_2$)$_2$-(3-(4-fluoro-phenyl)-[1,2,4]oxadiazol-5-yl), R$_1$ is CH$_3$;
Compound of Formula I-c where T is CO(CH$_2$)$_2$-(3-(3-bromo-phenyl)-[1,2,4]oxadiazol-5-yl), R$_1$ is CH$_3$;
Compound of Formula I-c where T is CO(CH$_2$)$_2$-(3-(4-nitro-phenyl)-[1,2,4]oxadiazol-5-yl), R$_1$ is CH$_3$;
Compound of Formula I-c where T is CO(CH$_2$)$_2$-(3-(3-fluoro-phenyl)-[1,2,4]oxadiazol-5-yl), R$_1$ is CH$_3$;
Compound of Formula I-c where T is CO(CH$_2$)$_2$-(3-(3-chloro-phenyl)-[1,2,4]oxadiazol-5-yl), R$_1$ is CH$_3$;
Compound of Formula I-c where T is CO(CH$_2$)$_2$-(3-(3-methoxy-phenyl)-[1,2,4]oxadiazol-5-yl), R$_1$ is CH$_3$;
Compound of Formula I-c where T is CO(CH$_2$)$_2$-(3-(3,5-dimethoxy-phenyl)-[1,2,4]oxadiazol-5-yl), R$_1$ is CH$_3$;
Compound of Formula I-c where T is CO(CH$_2$)$_2$-(3-(4-chloro-phenyl)-[1,2,4]oxadiazol-5-yl), R$_1$ is CH$_3$;
Compound of Formula I-c where T is CO(CH$_2$)$_2$-(3-(4-bromo-phenyl)-[1,2,4]oxadiazol-5-yl), R$_1$ is CH$_3$;
Compound of Formula I-c where T is CO(CH$_2$)$_2$-(3-(pyridin-4-yl)-[1,2,4]oxadiazol-5-yl), R$_1$ is CH$_3$;
Compound of Formula I-c where T is CO(CH$_2$)$_2$-(3-(pyridin-3-yl)-[1,2,4]oxadiazol-5-yl), R$_1$ is CH$_3$;
Compound of Formula I-c where T is CO(CH$_2$)$_2$-(3-(2-fluoro-5-methoxy-phenyl)-[1,2,4]oxadiazol-5-yl), R$_1$ is CH$_3$;
Compound of Formula I-c where T is CO(CH$_2$)$_2$-(3-phenyl-4H-imidazol-1-yl), R$_1$ is CH$_3$;
Compound of Formula I-c where T is CO(CH$_2$)$_2$CONH-(4-methoxy-phenyl), R$_1$ is CH$_3$;
Compound of Formula I-c where T is CO(CH$_2$)$_2$CONH-(3-methoxy-phenyl), R$_1$ is CH$_3$;
Compound of Formula I-c where T is CO(CH$_2$)$_2$CONH-(2-methoxy-phenyl), R$_1$ is CH$_3$;
Compound of Formula I-c where T is CO(CH$_2$)$_2$CONH-(2,4-difluorophenyl), R$_1$ is CH$_3$;
Compound of Formula I-c where T is CO(CH$_2$)$_2$CO-(4-(3-fluoro-phenyl)piperazin-1-yl), R$_1$ is CH$_3$;
Compound of Formula I-c where T is CH$_2$CH$_2$CH$_3$, R$_1$ is CH$_3$;
Compound of Formula I-c where T is CH$_2$CH$_2$OH, R$_1$ is CH$_3$;
Compound of Formula I-c where T is CH$_2$CH$_2$OC$_2$H$_5$, R$_1$ is CH$_3$;
Compound of Formula I-c where T is CH$_2$CH$_2$CH(CH$_3$)$_2$, R$_1$ is CH$_3$;
Compound of Formula I-c where T is CH$_2$CH(CH$_3$)$_2$, R$_1$ is CH$_3$;
Compound of Formula I-c where T is CH$_2$(CH$_2$)$_2$-phenyl, R$_1$ is CH$_3$;
Compound of Formula I-c where T is CH$_2$-phenyl, R$_1$ is CH$_3$;
Compound of Formula I-c where T is CH$_2$-(4-nitro)-phenyl, R$_1$ is CH$_3$;
Compound of Formula I-c where T is CH$_2$-(4-bromo)-phenyl, R$_1$ is CH$_3$;
Compound of Formula I-c where T is CH$_2$-(2-fluoro)-phenyl, R$_1$ is CH$_3$;
Compound of Formula I-c where T is CH$_2$-(3,5-difluoro)-phenyl, R$_1$ is CH$_3$;
Compound of Formula I-c where T is CH$_2$-(2,4-difluoro)-phenyl, R$_1$ is CH$_3$;
Compound of Formula I-c where T is CH$_2$-(4-methyl)-phenyl, R$_1$ is CH$_3$;
Compound of Formula I-c where T is CH$_2$-(3-methoxy)-phenyl, R$_1$ is CH$_3$;
Compound of Formula I-c where T is CH$_2$-(2-methyl)-phenyl, R$_1$ is CH$_3$;
Compound of Formula I-c where T is CH$_2$CH$_2$-(4-(pyridin-2-yl)piperazinyl), R$_1$ is CH$_3$;
Compound of Formula I-c where T is CH$_2$CH$_2$-(1-(3-methoxy)phenyl-1H-[1,2,3]triazol-4-yl), R$_1$ is CH$_3$;
Compound of Formula I-c where T is CH$_2$-(1-(4-methoxy-2-fluoro-phenyl)-1H-[1,2,3]triazol-4-yl), R$_1$ is CH$_3$;
Compound of Formula I-c where T is CH$_2$-(5-methyl-[1,2,4]oxadiazol-3-yl), R$_1$ is CH$_3$;
Compound of Formula I-c where T is CH$_2$-(3-(5-fluoro-2-methoxyphenyl)-isoxazol-5-yl), R$_1$ is CH$_3$;
Compound of Formula I-c where T is CH$_2$CH=CH$_2$, R$_1$ is CH$_3$;
Compound of Formula I-c where T is CH$_2$CH$_2$CH=CH$_2$, R$_1$ is CH$_3$;
Compound of Formula I-c where T is CH$_2$CH=CH-phenyl, R$_1$ is CH$_3$;
Compound of Formula I-c where T is CH$_2$CH=CH-(2-methoxy)phenyl, R$_1$ is CH$_3$;
Compound of Formula I-c where T is CH$_2$CH=CH-(3-fluoro)phenyl, R$_1$ is CH$_3$;
Compound of Formula I-c where T is CH$_2$CH=CH-(4-cyano)phenyl, R$_1$ is CH$_3$;
Compound of Formula I-c where T is CH$_2$C(CH$_3$)=CH$_2$, R$_1$ is CH$_3$;
Compound of Formula I-c where T is CH$_2$CH=C(CH$_3$)$_2$, R$_1$ is CH$_3$;
Compound of Formula I-c where T is CH$_2$CH=CH-(3-cyano)phenyl, R$_1$ is CH$_3$;
Compound of Formula I-c where T is CH$_2$CH=CH-(3-acetoxy)phenyl, R$_1$ is CH$_3$;
Compound of Formula I-c where T is CH$_2$CH=CH-(3-hydroxymethyl)phenyl, R$_1$ is CH$_3$;
Compound of Formula I-c where T is CH$_2$CH=CH-(4-trifluoromethyl)phenyl, R$_1$ is CH$_3$;
Compound of Formula I-c where T is CH$_2$CH=CH-(3-trifluoromethyl)phenyl, R$_1$ is CH$_3$;
Compound of Formula I-c where T is CH$_2$CH=CH-(2,3-dihydro-benzo[1,4]dioxin-6-yl), R$_1$ is CH$_3$;
Compound of Formula I-c where T is CH$_2$CN, R$_1$ is CH$_3$;
Compound of Formula I-c where T is CH$_2$C(NH$_2$)=N—OH, R$_1$ is CH$_3$;
Compound of Formula I-c where T is CH$_2$C≡CH, R$_1$ is CH$_3$;
Compound of Formula I-c where T is CH$_2$C≡C-phenyl, R$_1$ is CH$_3$;
Compound of Formula I-c where T is CH$_2$C≡C-(3-cyano)phenyl, R$_1$ is CH$_3$;
Compound of Formula I-c where T is CH$_2$C≡C-(3-methyl)phenyl, R$_1$ is CH$_3$;
Compound of Formula I-c where T is COCH=CH-phenyl, R$_1$ is CH$_3$;
Compound of Formula I-c where T is CO(CH$_2$)$_2$-phenyl, R$_1$ is CH$_3$;
Compound of Formula I-c where T is COCH=CH-(pyridin-4-yl), R$_1$ is CH$_3$;

Compound of Formula I-c where T is COCH=CH-(pyridin-3-yl), R$_1$ is CH$_3$;
Compound of Formula I-c where T is COCH=CH-(pyridin-2-yl), R$_1$ is CH$_3$;
Compound of Formula I-c where T is COCH=CH-(1-(2-methoxy-phenyl)-1H-[1,2,3]triazol-4-yl), R$_1$ is CH$_3$;
Compound of Formula I-c where T is COCH=CH-(1-(3-methoxy-phenyl)-1H-[1,2,3]triazol-4-yl), R$_1$ is CH$_3$;
Compound of Formula I-c where T is COCH=CH-(1-(4-methoxy-phenyl)-1H-[1,2,3]triazol-4-yl), R$_1$ is CH$_3$;
Compound of Formula I-c where T is COCH=CH-(1-(4-fluoro-phenyl)-1H-[1,2,3]triazol-4-yl), R$_1$ is CH$_3$;
Compound of Formula I-c where T is COCH=CH-(1-(3-fluoro-phenyl)-1H-[1,2,3]triazol-4-yl), R$_1$ is CH$_3$;
Compound of Formula I-c where T is COCH$_2$NHCONH-phenyl, R$_1$ is CH$_3$;
Compound of Formula I-c where T is COCH$_2$NHCONH-(4-fluorophenyl), R$_1$ is CH$_3$;
Compound of Formula I-c where T is COCH$_2$NHCONH-(3-chloro-4-methylphenyl), R$_1$ is CH$_3$;
Compound of Formula I-c where T is CH$_2$CONH$_2$, R$_1$ is CH$_3$;
Compound of Formula I-c where T is CH$_2$CONH-phenyl, R$_1$ is CH$_3$;
Compound of Formula I-c where T is CH$_2$CONH-(3-fluoro)phenyl, R$_1$ is CH$_3$;
Compound of Formula I-c where T is CH$_2$CONH-(2-fluoro)phenyl, R$_1$ is CH$_3$;
Compound of Formula I-c where T is CH$_2$CONH-(4-fluoro)phenyl, R$_1$ is CH$_3$;
Compound of Formula I-c where T is CH$_2$CONH-(2,4-difluoro)phenyl, R$_1$ is CH$_3$;
Compound of Formula I-c where T is CH$_2$CONH-(3,4-difluoro)phenyl, R$_1$ is CH$_3$;
Compound of Formula I-c where T is CH$_2$CONH-(2,3,4-trifluoro)phenyl, R$_1$ is CH$_3$;
Compound of Formula I-c where T is CH$_2$CONH-(3-chloro)phenyl, R$_1$ is CH$_3$;
Compound of Formula I-c where T is CH$_2$CONH-(2-methoxy)phenyl, R$_1$ is CH$_3$;
Compound of Formula I-c where T is CH$_2$CONH-(3-methoxy)phenyl, R$_1$ is CH$_3$;
Compound of Formula I-c where T is CH$_2$CONH-(3,5-dimethoxy)phenyl, R$_1$ is CH$_3$;
Compound of Formula I-c where T is CH$_2$CONH-cyclopropyl, R$_1$ is CH$_3$;
Compound of Formula I-c where T is CH$_2$CON(CH$_3$)-(3-fluoro)phenyl, R$_1$ is CH$_3$;
Compound of Formula I-c where T is CH$_2$CON(CH$_3$)-(4-chloro)phenyl, R$_1$ is CH$_3$;
Compound of Formula I-c where T is CH$_2$CONH-(6-pyrazol-1-yl-pyridin-3-yl), R$_1$ is CH$_3$;
Compound of Formula I-c where T is CH$_2$CONH-(3-(pyrazol-1-yl)-pyridin-5-yl), R$_1$ is CH$_3$;
Compound of Formula I-c where T is CH$_2$-(1-(4-fluorophenyl)-1H-[1,2,3]-triazol-5-yl), R$_1$ is CH$_3$;
Compound of Formula I-c where T is CH$_2$-(1-(3-fluorophenyl)-1H-[1,2,3]-triazol-5-yl), R$_1$ is CH$_3$;
Compound of Formula I-c where T is CH$_2$-(1-(3,5-difluoro phenyl)-1H-[1,2,3]-triazol-5-yl), R$_1$ is CH$_3$;
Compound of Formula I-c where T is CH$_2$-(1-(3,4-difluoro phenyl)-1H-[1,2,3]-triazol-5-yl), R$_1$ is CH$_3$;
Compound of Formula I-c where T is CH$_2$-(1-(3,4,5-trifluoro phenyl)-1H-[1,2,3]-triazol-5-yl), R$_1$ is CH$_3$;
Compound of Formula I-c where T is CH$_2$-(1-(3-chlorophenyl)-1H-[1,2,3]-triazol-5-yl), R$_1$ is CH$_3$;
Compound of Formula I-c where T is CH$_2$-(5-(pyridin-3-yl)-[1,2,4]-oxadiazol-3-yl), R$_1$ is CH$_3$;
Compound of Formula I-c where T is CH$_2$CO$_2$CH$_2$CH$_3$, R$_1$ is CH$_3$;
Compound of Formula I-c where T is CONH-phenyl, R$_1$ is CH$_3$;
Compound of Formula I-c where T is CONH-(4-ethyl-phenyl), R$_1$ is CH$_3$;
Compound of Formula I-c where T is CH$_2$CO-(4-(phenyl)-piperazinyl), R$_1$ is CH$_3$;
Compound of Formula I-c where T is CH$_2$CO-(4-(2-fluorophenyl)-piperazinyl), R$_1$ is CH$_3$;
Compound of Formula I-c where T is CO(CH$_2$)$_2$CO-(4-phenyl)-piperazinyl, R$_1$ is CH$_3$;
Compound of Formula I-c where T is CO(CH$_2$)$_2$-[3-(4-methoxy-phenyl)-[1,2,4]oxadiazol-5-yl], R$_1$ is CH$_3$;
Compound of Formula I-c where T is CO(CH$_2$)$_2$-(1-pyridin-3-yl-1H-[1,2,3]-triazol-4yl), R$_1$ is CH$_3$;
Compound of Formula I-c where T is CO(CH$_2$)$_2$-(1-(2-methoxy)phenyl)-1H-[1,2,3]triazol-4-yl), R$_1$ is CH$_3$;
Compound of Formula I-c where T is CO(CH$_2$)$_2$-(1-(3-fluorophenyl)-1H-[1,2,3]triazol-4-yl), R$_1$ is CH$_3$;
Compound of Formula I-c where T is CO(CH$_2$)$_2$-(3-phenyl-[1,2,4]oxadiazol-5-yl), R$_1$ is CH$_3$;
Compound of Formula I-c where T is CO(CH$_2$)$_2$-(3-naphthalen-2-yl-[1,2,4]oxadiazol-5-yl), R$_1$ is CH$_3$;
Compound of Formula I-c where T is CO(CH$_2$)$_2$-(1-(pyridin-3-yl)-[1,2,4]oxadiazol-5-yl), R$_1$ is CH$_3$;
Compound of Formula I-c where T is CO(CH$_2$)$_2$-(1-(3,5-difluoro-phenyl)-1H-[1,2,3]triazol-4-yl), R$_1$ is CH$_3$;
Compound of Formula I-c where T is CO(CH$_2$)$_2$-(1-(3,4-difluoro-phenyl)-1H-[1,2,3]triazol-4-yl), R$_1$ is CH$_3$;
Compound of Formula I-c where T is CO(CH$_2$)$_2$-(4-(2-methoxy-phenyl)-piperazine-1-yl), R$_1$ is CH$_3$;
Compound of Formula I-c where T is CO(CH$_2$)$_2$-(1-(3,5-dimethoxy-phenyl)-1H-[1,2,3]triazol-4-yl), R$_1$ is CH$_3$;
Compound of Formula I-c where T is CO(CH$_2$)$_2$-(1-(3-methoxy-phenyl)-1H-[1,2,3]triazol-4-yl), R$_1$ is CH$_3$;
Compound of Formula I-c where T is CO(CH$_2$)$_2$-(3-(2-fluoro-5-methoxy-phenyl)-[1,2,4]oxadiazol-5-yl), R$_1$ is CH$_3$;

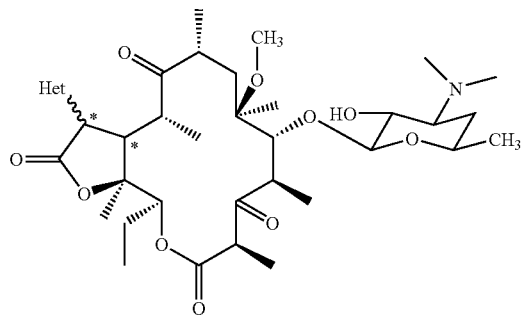

Formula I-e

Compound of Formula I-e where Het is 1H-tetrazol-5-yl;
Compound of Formula I-e where Het is 5-methyl-[1,2,4]oxadiazol-3-yl;
Compound of Formula I-e where Het is 4,5-dihydro-1H-imidazol-2-yl;
Compound of Formula I-e where Het is 1,4,5,6-tetrahydropyrimidin-2-yl;
Compound of Formula I-e where Het is 2-(2-methoxyethoxy)-2H-tetrazol-5-yl;
Compound of Formula I-e where Het is 1-(2-methoxyethoxy)-1H-tetrazol-5-yl;

Compound of Formula I-e where Het is [1,2,4]-oxadiazol-3yl;
Compound of Formula I-e where Het is (5-trifluoromethyl)-[1,2,4]-oxadiazol-3yl;
Compound of Formula I-e where Het is (4,5)-dihydro-1H-imidazol-2-yl;
Compound of Formula I-e where Het is 1-(allyl)-1H-tetrazol-5-yl
Compound of Formula I-e where Het is 2-(allyl)-2H-tetrazol-5-yl Formula I-f

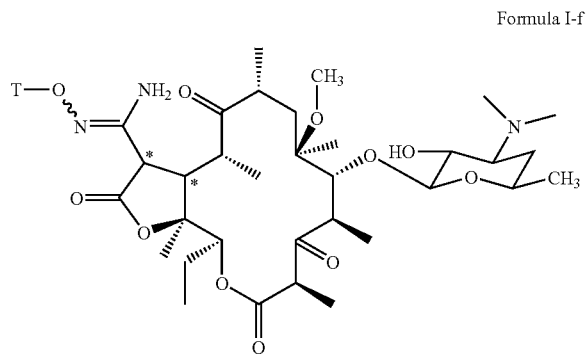

Compound of Formula I-f where T is H;
Compound of Formula I-f where T is $CH_3$;
Compound of Formula I-f where T is $CH_2CH_2CH_3$;
Compound of Formula I-f where T is $CH_2CN$;
Compound of Formula I-f where T is $CH_2OCH_2CH_2OCH_3$;
Compound of Formula I-f where T is $CH_2CH_2CH(CH_3)_2$;
Compound of Formula I-f where T is $CH_2$-cyclopropyl;
Compound of Formula I-f where T is $CH_2CH=CH_2$;
Compound of Formula I-f where T is $CH_2C(=CH_2)CH_3$;
Compound of Formula I-f where T is $CH_2CH=C(CH_3)_2$;
Compound of Formula I-f where T is $CH_2CH=CHCH_3$;
Compound of Formula I-f where T is $CH_2C(F)=CH_2$;
Compound of Formula I-f where T is $CH_2CH=CH$-phenyl;
Compound of Formula I-f where T is $CH_2CH=CH$-(3-fluoro)phenyl;
Compound of Formula I-f where T is $CH_2CH=CH$-(3-chloro)phenyl;
Compound of Formula I-f where T is $CH_2CH=CH$-(3-trifluoromethyl)phenyl;
Compound of Formula I-f where T is $CH_2CH=CH$-(2-trifluoromethyl)phenyl;
Compound of Formula I-f where T is $CH_2CH=CH$-(pyridin-3-yl);
Compound of Formula I-f where T is $CH_2CH=CH$-(pyrimidin-5-yl);
Compound of Formula I-f where T is $CH_2C\equiv CH$;
Compound of Formula I-f where T is $CH_2C\equiv C$-phenyl;
Compound of Formula I-f where T is $CH_2C\equiv C$-(3-cyano)phenyl;
Compound of Formula I-f where T is $CH_2C\equiv C$-(3-methyl)phenyl;
Compound of Formula I-f where T is $CH_2C\equiv C$-(3-fluoro)phenyl;
Compound of Formula I-f where T is $CH_2C\equiv C$-(3-chloro)phenyl;
Compound of Formula I-f where T is $CH_2C\equiv C$-(3-methoxy)phenyl;
Compound of Formula I-f where T is $CH_2C\equiv C$-(pyridin-2-yl);
Compound of Formula I-f where T is $CH_2C\equiv C$-(2-chloropyridin-5-yl);
Compound of Formula I-f where T is $CH_2C\equiv C$-(2-fluoropyridin-5-yl);
Compound of Formula I-f where T is $CH_2C\equiv C$-(pyridin-3-yl);
Compound of Formula I-f where T is $CH_2$-phenyl;
Compound of Formula I-f where T is $CH_2(CH_2)_2$-phenyl;
Compound of Formula I-f where T is $CH_2$-(4-methoxyphenyl);
Compound of Formula I-f where T is $CH_2$-(3-chlorophenyl);
Compound of Formula I-f where T is $CH_2$-(3-methoxyphenyl);
Compound of Formula I-f where T is $CH_2$-(2-fluorophenyl);
Compound of Formula I-f where T is $CH_2$-(4-(isopropyl)phenyl);
Compound of Formula I-f where T is $CH_2$-(4-(1H-[1,2,4]-triazol)phenyl);
Compound of Formula I-f where T is $CH_2$-(4-(pyrimidin-5-yl)phenyl);
Compound of Formula I-f where T is $CH_2$-(4-(pyridin-2-yl)phenyl);
Compound of Formula I-f where T is $CH_2$-(5-phenyl[1,3,4]oxadiazol-2-yl);
Compound of Formula I-f where T is $CH_2$-(5-(pyridin-3-yl)[1,3,4]oxadiazol-2-yl);
Compound of Formula I-f where T is $CH_2$-(5-(3-fluorophenyl)[1,3,4]oxadiazol-2-yl);
Compound of Formula I-f where T is $CH_2$-(5-(4-methoxyphenyl)[1,3,4]oxadiazol-2-yl);
Compound of Formula I-f where T is $CH_2$-(5-(pyridin-2-yl)[1,3,4]oxadiazol-2-yl);
Compound of Formula I-f where T is $CH_2$-(5-(pyrazin-2-yl)[1,3,4]oxadiazol-2-yl);
Compound of Formula I-f where T is $CH_2$-(5-(3,5-dimethoxyphenyl)[1,3,4]oxadiazol-2-yl);
Compound of Formula I-f where T is $CH_2$-(5-(pyrimidin-2-yl)[1,3,4]oxadiazol-2-yl);
Compound of Formula I-f where T is $CH_2$-(5-(6-methoxypyridin-2-yl)[1,3,4]oxadiazol-2-yl);
Compound of Formula I-f where T is $CH_2$-((5-cyclopropyl)-[1,3,4]oxadiazol-2-yl);
Compound of Formula I-f where T is $CH_2$-(5-(5-methylpyridin-2-yl)[1,3,4]oxadiazol-2-yl);
Compound of Formula I-f where T is $CH_2$-(5-(5-cyclopropyl-pyridin-2-yl)[1,3,4]oxadiazol-2-yl)
Compound of Formula I-f where T is $CH_2$-(5-(5-cyano-pyridin-2-yl)[1,3,4]oxadiazol-2-yl);
Compound of Formula I-f where T is $CH_2$-(5-(5-dimethylamino-pyridin-2-yl)[1,3,4]oxadiazol-2-yl);
Compound of Formula I-f where T is $CH_2$-(5-(5-methoxypyridin-2-yl) [1,3,4]oxadiazol-2-yl);
Compound of Formula I-f where T is $CH_2$-(5-(5-fluoro-pyridin-2-yl)[1,3,4]oxadiazol-2-yl);
Compound of Formula I-f where T is $CH_2$-(5-(5-chloro-pyridin-2-yl)[1,3,4]oxadiazol-2-yl);
Compound of Formula I-f where T is $CH_2$-(5-(pyrimidin-5-yl)[1,3,4]oxadiazol-2-yl);
Compound of Formula I-f where T is $CH_2$-3-phenyl[1,2,4]oxadiazol-5-yl);
Compound of Formula I-f where T is $CH_2$-(3-(3-fluorophenyl)[1,2,4]oxadiazol-5-yl);
Compound of Formula I-f where T is $CH_2$-(3-(3-chlorophenyl)[1,2,4]oxadiazol-5-yl);
Compound of Formula I-f where T is $CH_2$-(3-(4-chlorophenyl)[1,2,4]oxadiazol-5-yl);

Compound of Formula I-f where T is CH$_2$-(3-(4-methoxyphenyl)[1,2,4]oxadiazol-5-yl);
Compound of Formula I-f where T is CH$_2$-(3-(3,5-dimethoxyphenyl)[1,2,4]oxadiazol-5-yl);
Compound of Formula I-f where T is CH$_2$-(3-(pyridin-3-yl)[1,2,4]oxadiazol-5-yl);
Compound of Formula I-f where T is CH$_2$-(3-(pyridin-2-yl)[1,2,4]oxadiazol-5-yl);
Compound of Formula I-f where T is CH$_2$-(3-(pyrimidin-2-yl)[1,2,4]oxadiazol-5-yl);
Compound of Formula I-f where T is CH$_2$-(3-cyclopropyl[1,2,4]oxadiazol-5-yl);
Compound of Formula I-f where T is CH$_2$-(3-(6-methylpyridin-2-yl)[1,2,4]oxadiazol-5-yl);
Compound of Formula I-f where T is CH$_2$-(3-(3-methylpyridin-2-yl)[1,2,4]oxadiazol-5-yl);
Compound of Formula I-f where T is CH$_2$-(5-methyl[1,2,4]oxadiazol-3-yl);
Compound of Formula I-f where T is CH$_2$-(5-phenyl[1,2,4]oxadiazol-3-yl);
Compound of Formula I-f where T is CH$_2$-(5-(3-fluorophenyl)[1,2,4]oxadiazol-3-yl);
Compound of Formula I-f where T is CH$_2$-(5-(3-chlorophenyl)[1,2,4]oxadiazol-3-yl);
Compound of Formula I-f where T is CH$_2$-(5-(3-fluoro-4-methoxyphenyl)[1,2,4]oxadiazol-3-yl);
Compound of Formula I-f where T is CH$_2$-(5-(3-cyanophenyl)[1,2,4]oxadiazol-3-yl);
Compound of Formula I-f where T is CH$_2$-(5-(pyridin-3-yl)[1,2,4]oxadiazol-3-yl);
Compound of Formula I-f where T is CH$_2$-(5-(pyrazin-2-yl)[1,2,4]oxadiazol-3-yl);
Compound of Formula I-f where T is CH$_2$-(5-(pyridin-2-yl)[1,2,4]oxadiazol-3-yl);
Compound of Formula I-f where T is CH$_2$-(5-(pyridin-4-yl)[1,2,4]oxadiazol-3-yl);
Compound of Formula I-f where T is CH$_2$-(5-(2-chloropyridin-3-yl)[1,2,4]oxadiazol-3-yl);
Compound of Formula I-f where T is CH$_2$-(5-(2-methoxypyridin-3-yl)[1,2,4]oxadiazol-3-yl);
Compound of Formula I-f where T is CH$_2$-(5-(2-fluoropyridin-3-yl)[1,2,4]oxadiazol-3-yl);
Compound of Formula I-f where T is CH$_2$-(5-cyclopropyl[1,2,4]oxadiazol-3-yl);
Compound of Formula I-f where T is CH$_2$-(5-(6-methylpyridin-2-yl)[1,2,4]oxadiazol-3-yl);
Compound of Formula I-f where T is CH$_2$-(5-methyl[1,2,4]oxadiazol-3-yl);
Compound of Formula I-f where T is CH$_2$-(5-trifluoromethyl[1,2,4]oxadiazol-3-yl);
Compound of Formula I-f where T is CH$_2$-(5-(pyridazin-2-yl)-[1,2,4]oxadiazol-3-yl);
Compound of Formula I-f where T is CH$_2$-(5-(2-methyl-oxazol-4-yl)-[1,2,4]oxadiazol-3-yl);
Compound of Formula I-f where T is CH$_2$-(5-(2-methyl-thiazol-4-yl)-[1,2,4]oxadiazol-3-yl);
Compound of Formula I-f where T is CH$_2$-(5-(pyrimidin-2-yl)-[1,2,4]oxadiazol-3-yl);
Compound of Formula I-f where T is CH$_2$-(3-(pyridin-3-yl)-isoxazol-5-yl);
Compound of Formula I-f where T is CH$_2$-(3-(3-fluorophenyl)-isoxazol-5-yl);
Compound of Formula I-f where T is CH$_2$-(3-(3-chlorophenyl)-isoxazol-5-yl);
Compound of Formula I-f where T is CH$_2$-(3-(4-fluorophenyl)-isoxazol-5-yl);
Compound of Formula I-f where T is CH$_2$-(3-(pyridin-2-yl)-isoxazol-5-yl);
Compound of Formula I-f where T is CH$_2$-(3-(3-methoxyphenyl)-isoxazol-5-yl);
Compound of Formula I-f where T is CH$_2$-(3-phenyl-isoxazol-5-yl);
Compound of Formula I-f where T is CH$_2$-(3-methyl-isoxazol-5-yl);
Compound of Formula I-f where T is CH$_2$-(3-(6-methoxypyridin-2-yl)-isoxazol-5-yl);
Compound of Formula I-f where T is CH$_2$-(3-(2-methoxypyridin-5-yl)-isoxazol-5-yl);
Compound of Formula I-f where T is CH$_2$CONH$_2$;
Compound of Formula I-f where T is CH$_2$CON(CH$_3$)$_2$;
Compound of Formula I-f where T is CH$_2$CONH-(cyclopropyl);
Compound of Formula I-f where T is CH$_2$CONH-(3-chlorophenyl);
Compound of Formula I-f where T is CH$_2$CONH-(3-fluorophenyl);
Compound of Formula I-f where T is CH$_2$CO-(4-phenylpiperazin-1yl);
Compound of Formula I-f where T is CO(CH$_2$)$_2$-(3-fluorophenyl);
Compound of Formula I-f where T is CO(CH$_2$)$_2$-(4-methoxyphenyl);
Compound of Formula I-f where T is CO(CH$_2$)$_2$-(2,3-dimethoxyphenyl);
Compound of Formula I-f where T is CO(CH$_2$)$_2$-(3-(3-fluorophenyl)-[1,2,4]oxadiazol-5-yl);
Compound of Formula I-f where T is CONH-(4-ethylphenyl);
Compound of Formula I-f where T is CH$_2$-(3-(5-methylpyridin-2-yl)[1,2,4]oxadiazol-5-yl);
Compound of Formula I-f where T is CH$_2$-(3-(5-cyclopropyl-pyridin-2-yl)[1,2,4]oxadiazol-5-yl);
Compound of Formula I-f where T is CH$_2$-(3-(5-cyano-pyridin-2-yl)[1,2,4]oxadiazol-5-yl);
Compound of Formula I-f where T is CH$_2$-(3-(5-dimethyl amino-pyridin-2-yl)[1,2,4]oxadiazol-5-yl);
Compound of Formula I-f where T is CH$_2$-(3-(5-methoxy-pyridin-2-yl)[1,2,4]oxadiazol-5-yl);
Compound of Formula I-f where T is CH$_2$-(3-(5-fluoro-pyridin-2-yl)[1,2,4]oxadiazol-5-yl);
Compound of Formula I-f where T is CH$_2$-(3-(5-chloro-pyridin-2-yl)[1,2,4]oxadiazol-5-yl);
Compound of Formula I-f where T is CH$_2$-(3-(pyrimidin-5-yl)[1,2,4]oxadiazol-5-yl);
Compound of Formula I-f where T is CH$_2$-(5-(5-methyl-pyridin-2-yl)-[1,2,4]oxadiazol-3-yl);
Compound of Formula I-f where T is CH$_2$-(5-(5-cyclopropyl-pyridin-2-yl)-[1,2,4]oxadiazol-3-yl);
Compound of Formula I-f where T is CH$_2$-(5-(5-cyano-pyridin-2-yl)-[1,2,4]oxadiazol-3-yl);
Compound of Formula I-f where T is CH$_2$-(5-(5-dimethyl amino-pyridin-2-yl)-[1,2,4]oxadiazol-3-yl);
Compound of Formula I-f where T is CH$_2$-(5-(5-methoxy-pyridin-2-yl)-[1,2,4]oxadiazol-3-yl);
Compound of Formula I-f where T is CH$_2$-(5-(5-fluoro-pyridin-2-yl)-[1,2,4]oxadiazol-3-yl);
Compound of Formula I-f where T is CH$_2$-(5-(5-chloro-pyridin-2-yl)-[1,2,4]oxadiazol-3-yl);
Compound of Formula I-f where T is CH$_2$-(5-(pyrimidin-5-yl)-[1,2,4]oxadiazol-3-yl);
Compound of Formula I-f where T is CH$_2$-(5-(3-fluorophenyl)-isoxazol-3-yl);

Compound of Formula I-f where T is CH$_2$-(5-(3-chlorophenyl)-isoxazol-3-yl);
Compound of Formula I-f where T is CH$_2$-(5-(4-fluorophenyl)-isoxazol-3-yl);
Compound of Formula I-f where T is CH$_2$-(5-(3-methoxyphenyl)-isoxazol-3-yl);
Compound of Formula I-f where T is CH$_2$-(5-phenyl)-isoxazol-3-yl);
Compound of Formula I-f where T is CH$_2$-(5-methyl)-isoxazol-3-yl);
Compound of Formula I-f where T is CH$_2$-(5-(6-methoxy-pyridin-2-yl)-isoxazol-3-yl);
Compound of Formula I-f where T is CH$_2$-(5-(2-methoxy-pyridin-5-yl)-isoxazol-3-yl);
Compound of Formula I-f where T is CH$_2$-(5-(5-methyl-pyridin-2-yl)-isoxazol-3-yl);
Compound of Formula I-f where T is CH$_2$-(5-(5-cyclopropyl-pyridin-2-yl)-isoxazol-3-yl);
Compound of Formula I-f where T is CH$_2$-(5-(5-cyano-pyridin-2-yl)-isoxazol-3-yl);
Compound of Formula I-f where T is CH$_2$-(5-(5-dimethyl amino-pyridin-2-yl)-isoxazol-3-yl);
Compound of Formula I-f where T is CH$_2$-(5-(5-methoxy-pyridin-2-yl)-isoxazol-3-yl);
Compound of Formula I-f where T is CH$_2$-(5-(5-fluoro-pyridin-2-yl)-isoxazol-3-yl);
Compound of Formula I-f where T is CH$_2$-(5-(5-chloro-pyridin-2-yl)-isoxazol-3-yl);
Compound of Formula I-f where T is CH$_2$-(pyrimidin-5-yl)-isoxazol-3-yl);
Compound of Formula I-f where T is CH$_2$CH$_2$-(4-(pyridin-2-yl)-1H-imidazol-1-yl);
Compound of Formula I-f where T is CH$_2$CH$_2$-(4-(pyridin-3-yl)-1H-imidazol-1-yl);
Compound of Formula I-f where T is CH$_2$CH$_2$-(4-(6-methyl-pyridin-2-yl)-1H-imidazol-1-yl);
Compound of Formula I-f where T is CH$_2$CH$_2$-(4-(4-methoxy-pyridin-2-yl)-1H-imidazol-1-yl);
Compound of Formula I-f where T is CH$_2$-(4-(pyridin-2-yl)-pyrazol-4-yl);
Compound of Formula I-f where T is CH$_2$-(4-(pyridin-3-yl)-pyrazol-4-yl);
Compound of Formula I-f where T is CH$_2$-(4-(6-methyl-pyridin-2-yl)-pyrazol-4-yl);
Compound of Formula I-f where T is CH$_2$-(4-(4-methoxy-pyridin-2-yl)-pyrazol-4-yl);
Compound of Formula I-f where T is CH$_2$-(4-(5-methoxy-pyridin-2-yl)-pyrazol-4-yl);
Compound of Formula I-f where T is CH$_2$-(1-(pyridin-2-yl)-1H-imidazol-4-yl);
Compound of Formula I-f where T is CH$_2$-(1-(pyridin-3-yl)-1H-imidazol-4-yl);
Compound of Formula I-f where T is CH$_2$-(1-(6-methyl-pyridin-2-yl)-1H-imidazol-4-yl);
Compound of Formula I-f where T is CH$_2$-(1-(4-methoxy-pyridin-2-yl)-1H-imidazol-4-yl);
Compound of Formula I-f where T is CH$_2$-(1-(5-methoxy-pyridin-2-yl)-1H-imidazol-4-yl);
Compound of Formula I-f where T is CH$_2$-(2-(pyridin-2-yl)-oxazol-4-yl);
Compound of Formula I-f where T is CH$_2$-(2-(pyridin-3-yl)-oxazol-4-yl);
Compound of Formula I-f where T is CH$_2$-(2-(6-methyl-pyridin-2-yl)-oxazol-4-yl);
Compound of Formula I-f where T is CH$_2$-(2-(4-methoxy-pyridin-2-yl)-oxazol-4-yl);
Compound of Formula I-f where T is CH$_2$-(2-(5-methoxy-pyridin-2-yl)-oxazol-4-yl);

The compounds of present invention include stereoisomers. The term "stereoisomer" refers to compounds, which have identical chemical composition, but differ with regard to arrangement of the atoms and the groups in space. These include enantiomers, diastereomers, geometrical isomers, atropisomer and conformational isomers. Geometric isomers may occur when a compound contains a double bond or some other feature that gives the molecule a certain amount of structural rigidity. An enantiomer is a stereoisomer of a reference molecule that is the nonsuperimposable mirror image of the reference molecule. A diastereomer is a stereoisomer of a reference molecule that has a shape that is not the mirror image of the reference molecule. An atropisomer is a conformation of a reference compound that converts to the reference compound only slowly on the NMR or laboratory time scale. Conformational isomers (or conformers or rotational isomers or rotamers) are stereoisomers produced by rotation about a bonds, and are often rapidly interconverting at room temperature. Racemic mixtures are also encompassed within the scope of this invention. Some of the compounds of the present invention may have trans and cis isomers and geometric E- and Z-isomers. The wavy bond indicates that the compounds may be present as either of E- or Z-isomer. Also some of the compounds according to this invention may exist as diastereomers. In addition, where the process for the preparation of the compounds according to the invention give rise to mixture of stereoisomers, these isomers, may be separated by conventional techniques such as preparative chromatography and HPLC. The compounds may be prepared as a single stereoisomer or in racemic form as a mixture of some possible stereoisomer.

Furthermore, some of the compounds may exists as different polymorphs such as crystalline or amorphous forms and as such are intended to be included in the present invention. In addition, some of the compounds may form solvates with water (i.e. hydrates) which, contains various amounts of water, for instance the hydrate, hemihydrate and sesquihydrate forms. Also the compound can form solvates with common organic solvents, and such solvates are also intended to be encompassed within the scope of this invention.

DESCRIPTION OF TERMS

The following definitions are used, unless otherwise described.

The term "C$_1$-C$_6$ alkyl" refers to saturated, straight or branched chain hydrocarbon radicals containing between one and six carbon atoms. Examples of C$_1$-C$_6$ alkyl radicals, include but are not limited to, methyl, ethyl, propyl, butyl, pentyl, hexyl, and their branched isomers such as iso-propyl, iso-butyl, tert-butyl.

The term "C$_2$-C$_6$ alkenyl" refers to straight or branched-chain hydrocarbon radicals comprising two to six carbon atoms, which contain one or more carbon-carbon double bonds. Examples of C$_2$-C$_6$ alkenyl radicals, include but are not limited to, ethenyl, propenyl, butenyl, 1-methyl-2-buten-1-yl, and the like.

The term "C$_2$-C$_6$ alkynyl" refers to straight or branched chain hydrocarbon radicals comprising two to six carbon atoms respectively, which contain one or more carbon-carbon triple bonds. Examples of C$_2$-C$_6$ alkynyl radicals, include but are not limited to, ethynyl, propynyl, butynyl, 1-methyl-2-butyn-1-yl, and the like.

The substituted C$_1$-C$_6$ alkyl, substituted C$_2$-C$_6$ alkenyl, C$_2$-C$_6$ substituted alkynyl is defined as the respective alkyl, alkenyl, alkynyl substituted, by independent replacement of one or two or three of the hydrogen atoms thereon with Cl, Br, F, 1, $NO_2$, CN, OH, haloalkyl, $C_1$-$C_6$ alkoxy, amino, alkylamino, dialkylamino, mercapto, formyl, carboxy, alkoxycarbonyl and carboxamide (C(O)NR'R"), aryl, heteroaryl, substituted aryl, substituted heteroaryl.

Examples of $C_1$-$C_6$ alkoxy are methoxy, ethoxy, propyloxy, isopropyloxy, butyloxy, pentyloxy, hexyloxy.

The term "haloalkyl" denotes an alkyl group, as defined above, having one, two or three halogen atoms attached thereto and is exemplified by such groups as chloromethyl, bromoethyl, trifluoromethyl, and the like.

The term "alkylamino" refers to a group having the structure —NH($C_1$-$C_6$ alkyl) where $C_1$-$C_6$ alkyl is as previously defined.

The term "dialkylamino" refers to a group having the structure —N($C_1$-$C_6$ alkyl) ($C_1$-$C_6$ alkyl), where $C_1$-$C_6$ alkyl is as previously defined. Examples of dialkylamino are, but not limited to, dimethylamino, diethylamino, methylethylamino and the like.

The term "aryl" refers to a mono (6-membered) or bicyclic carbocyclic ring system having one or two aromatic ring including but not limited to phenyl, naphthyl, tetrahydronaphthyl, indanyl, indenyl and the like.

The term "heteroaryl" refers to a mono i.e. 5-6 membered or bicyclic i.e. fused aromatic ring system having at least one carbon atom of the aromatic ring replaced by an atom selected from the group of N, O, S. The ring may be connected to the remaining part of the molecule via any of the ring atoms. For example pyridinyl, pyrazinyl, pyrimidinyl, pyrrolyl, pyrazolyl, imidazolyl, thiazolyl, isothiazolyl, oxazolyl, isoxazolyl, thiadiazolyl, oxadiazolyl, thienyl, triazolyl, triazinyl, tetrazolyl, furanyl, N-oxo-pyridinyl, and the like. It includes the fused biaryl systems such as indolyl, quinolinyl, isoquinolinyl, benzothiazolyl, benzoxazolyl, benzothienyl, N-oxoquinolyl, benzimidazolyl, benzopyranyl, benzoisothiazolyl, benzodiazinyl, benzofurazanyl, indazolyl, indolizinyl, benzofuryl, quinoxalinyl, pyrrolopyridinyl, furopyridinyl (such as furo[2,3-c]pyridinyl, furo[3,2-b]pyridinyl, furo[2,3-b]pyridinyl), naphthyridinyl, phthalazinyl, pyridinopyridinyl, quinazolinyl, thienofuryl, thienopyridinyl, thienotheinyl, purinyl (such as 9H-purin-1-yl, 6-amino-9H-purin-9-yl), pyridinyl-1H-pyrazol-1-yl and the like.

The aryl or the heteroaryl group can be optionally substituted by independent replacement of one or more of hydrogen atoms thereon with substituents selected from $C_1$-$C_6$ alkyl, substituted $C_1$-$C_6$ alkyl, cyano, hydroxy, halogen, amino, formyl, carboxy, carboxamide, $C_1$-$C_6$ alkoxy, $C_1$-$C_6$ thioalkoxy, $C_1$-$C_6$ alkylcarbonyl, amino, alkylamino, dialkylamino, mercapto, nitro, carboxy, alkoxycarbonyl, aminocarbonyl, alkylthio, arylthio, heteroarylthio, haloalkyl.

The "aralkyl" is defined as an alkyl group substituted with an aryl group for example benzyl, benzhydryl, trityl, wherein the aryl group may be optionally substituted as defined below.

The "heteroaralkyl" is defined as an alkyl group substituted with a heteroaryl group for example pyridinyl-methyl wherein the heteroaryl group may be optionally substituted as defined below.

The "aroyl" group refers to a carbonyl group attached to an aryl group for example benzoyl, wherein the aryl group may be optionally substituted as defined below.

The "heteroaroyl" is defined as a carbonyl group attached to a heteroaryl group for example pyridinyl carbonyl, wherein the heteroaryl group may be optionally substituted as defined below.

The "aralkanoyl" refers a carbonyl group attached to an aralkyl group for example phenylacetyl. The "heteroaralkanoyl" refers a carbonyl group attached to heteroaralkyl group for example pyridinylylacetyl. The cycloalkyl refers to 3-7 membered cyclic structures for example cyclopropyl, cyclobutyl, cyclopentyl, cyclohexyl, cycloheptyl.

The heterocyclyl refers to 3-7 membered cyclic structures including one or more heteroatoms such as N, O, S or can be defined as up to 4 heteroatoms selected from N, O, S. Examples of heterocyclyls are oxetanyl (oxetane is a four membered ring with an oxygen in the ring oxetanyl is a substituted oxetane). pyrrolidinyl, pyrazolinyl, imidazolinyl, imidazolidinyl, oxazolinyl, oxazolidinyl, isoxazolinyl, thiazolidinyl, isothiazolidinyl, tetrahydrofuryl, piperidinyl, piperazinyl, 2-oxopiperazinyl, 2-oxopiperidinyl, 2-oxopyrrolidinyl, 4-oxo piperidinyl, tetrahydropyranyl, tetrahydrothiopyranyl, morpholinyl, [1,3]-dioxolane and the like.

The "hydroxyl protecting group" as used herein refers to an easily removable group which is known in the art to protect a hydroxyl group against undesirable reaction during synthetic procedures and to be selectively removable. The use of hydroxy-protecting groups against undesirable reactions during a synthesis procedure and any such protecting groups are known cf., for example, T. H. Greene and P. G. M. Wuts, Protective Groups in Organic Synthesis, $2^{nd}$ edition, John Wiley & sons, New York (1991). Examples of hydroxyl protecting groups include but are not limited to triethylsilyl, trimethylsilyl, acetyl, benzoyl, methoxymethyl, methoxyethoxymethyl, benzyl, tertbutyldimethylsilyl and the like.

The terms "halo", "halide" and "halogen" as used herein refer to an atom selected from fluorine, chlorine, bromine and iodine. The term "formyl" as used herein refers to a group of Formula —CHO. The term "sulphonyl" refers to a group of Formula —$SO_2$—. "Thiol" or "mercapto" refers to the group —SH.

The term "$C_1$-$C_6$ alkoxy" refers to a $C_1$-$C_6$ alkyl group, as previously defined, attached to the parent molecular moiety through an oxygen atom. Examples of $C_1$-$C_6$-alkoxy include, but are not limited to, methoxy, ethoxy, propoxy, isopropoxy, n-butoxy, tert-butoxy, neopentoxy and n-hexoxy.

The term "carboxamide" as used herein refers to a group of Formula C(O)NR'R" wherein R' and R" are independently selected from hydrogen or $C_1$-$C_6$ alkyl or R' and R" taken together may form a six or five membered heterocycle such as piperidine, pyrrolidine, piperazine and the like.

The term "ester" or "alkoxycarbonyl" refers to an $C_1$-$C_6$ alkoxy group attached to the parent molecular moiety through a carbonyl group such as methoxycarbonyl ($CO_2Me$), ethoxycarbonyl ($CO_2Et$), and the like.

The term "($C_1$-$C_6$)alkylcarbonyl" unless otherwise indicated, includes —C(O)-alkyl groups wherein "alkyl" is as defined above.

The terms "Me", "Et", "Ph", "allyl" stands for methyl, ethyl, phenyl and $CH_2CH$=$CH_2$ respectively. "MEM" stands for methoxyethoxymethyl.

The term "animal" refers to an animal such as a mammal, fish or a bird.

The phrase "pharmaceutically acceptable salt" as used herein refers to one or more salts of the free base of the invention which possess the desired pharmacological activity of the free base and which are neither biologically nor otherwise undesirable. The salts are suitable for use in contact with the tissues of human and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting the free base function with a suitable acid. These salts may be obtained from inorganic or organic acids. Examples of inorganic acids are hydrochloric acid, nitric acid, perchloric acid, hydrobromic acid, sulphuric acid or phosphoric acid. Examples of organic acids are acetic acid, propionic acid, oxalic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulphonic acid, p-toluene sulphonic acid, salicyclic acid and the like. Also included are the salts with various amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine or the optically active isomers thereof or the racemic mixtures thereof or dipeptides, tripeptides and polypeptides derived from the monoaminoacid units thereof.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malonate, 2-naphthalenesulfonate, nicotinate, oleate, palmitate, pamoate, pectinate, persulfate, 3-phenylpropionate, phosphate, picrate, pivalate, propionate, stearate, sulfate, tartrate, thiocyanate, p-toluenesulfonate, undecanoate, valerate salts, and the like.

Salt of an acid moiety in the compound can also be prepared by reacting with a suitable base. These suitable salts are furthermore those of the inorganic or organic bases. Inorganic bases such as KOH, NaOH, Ca(OH)$_2$, Al(OH)$_3$. The organic base salts from basic amines such as ethylamine, triethylamine, diethanolamine, ethylenediamine, guanidine or heterocyclic amines such as piperidine, hydroxyethylpyrrolidine, hydroxyethylpiperidine, morpholine, piperazine, N-methyl piperazine and the like or basic amino acids such as optically pure and racemic isomers of arginine, lysine, histidine, tryptophan and the like.

Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

"Therapeutically effective amount" means that amount of active compound(s) or pharmaceutical agent(s) that elicit the biological or medicinal response in a tissue system, animal or human sought by a researcher, veterinarian, medical doctor or other clinician, which response includes alleviation of the symptoms of the disease or disorder being treated. The specific amount of active compound(s) or pharmaceutical agent(s) needed to elicit the biological or medicinal response will depend on a number of factors, including but not limited to the disease or disorder being treated, the active compound(s) or pharmaceutical agent(s) being administered, the method of administration, and the condition of the patient. The term "treatment" unless otherwise indicated, includes the treatment or prevention of a microbial infection as provided in the method of the present invention.

As used herein, unless otherwise indicated, the term "microbial infection(s)" includes bacterial infections and protozoa infections which occur in human or animals including mammals, fish and birds as well as disorders related to bacterial infections and protozoa infections that may be treated or prevented by administering antibiotics such as the compounds of the present invention. Such bacterial infections and protozoa infections and disorders related to such infections include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus*, or *Peptostreptococcus* spp.; pharynigitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *Streptococcus pyogenes, Streptococcus agalactiae*, Streptococcal groups C-F (minute-colony streptococci), viridans streptococci, *Corynebacterium minutissimum, Clostridium* spp., or *Bartonella henselae*; uncomplicated acute urinary tract infections related to infection by *Staphylococcus saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and Toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis related to infection by *Helicobacter pylori* or *Chlamydia pneumoniae*. Bacterial infections and protozoa infections and disorders related to such infections that may be treated or prevented in animals include the following: bovine respiratory diseases related to infection by *P. haem., P. multocida, Mycoplasma bovis*, or *Bordetella* spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae, Klebsiella* spp., *Corynebacterium*, or *Enterococcus* spp.; swine respiratory disease related to infection by *A. pleuro., P. multocida*, or *Mycoplasma* spp.; swine enteric disease related to infection by *E. coli, Lawsonia intracellularis, Salmonella*, or *Serpulina hyodyisinteriae*; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *Staph. epidermidis, Staph. intermedius*, coagulase neg. *Staph.* or *P. multocida*; and dental or mouth infections in dogs and cats related to infection by *Alcaligenes* spp., *Bacteroides* spp., *Clostridium* spp., *Enterobacter* spp., *Eubacterium, Peptostreptococcus, Porphyromonas*, or *Prevotella*.

Antimicrobial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium for the observed bacterial isolates. Antimicrobial agents were serially diluted (2-fold) in DMSO to produce a concentration range, from about 64 µg/ml to about 0.03 µg/ml. The diluted compounds (2 µl/well) were then spotted to sterile 96-well microtiter plates. The inoculum for each bacterial strain was adjusted to $5.5 \times 10^5$ CFU/ml in appropriate MIC medium; 200 µl/well of this inoculum was added to the 96-well microtiter plate resulting in a final concentration of $1 \times 10^5$ CFU/ml. The 96 well plates were covered and incubated in a humidified atmosphere at 35±2° C. for 16-24 h depending on the bacterial strain tested. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 µg/ml to about 0.03 µg/ml.

All in vitro testing follows the guidelines described in the Approved Standards M7-A5 protocol, published by the National Committee for Clinical Laboratory Standards (NC-CLS).

The present invention encompasses certain compounds, dosage forms, and methods of administering the compounds to a human or other animal subject. Specific compounds and compositions to be used in the invention must, accordingly, be pharmaceutically acceptable. As used herein, such a "pharmaceutically acceptable" component is one that is suitable for use with humans and/or animals without undue adverse side effects (such as toxicity, irritation, and allergic response) commensurate with a reasonable benefit/risk ratio.

The pharmaceutical compositions are prepared according to conventional procedures used by persons skilled in the art to make stable and effective compositions. In the solid, liquid, parenteral and topical dosage forms, an effective amount of the active compound or the active ingredient is any amount, which produces the desired results.

For the purpose of this invention the pharmaceutical compositions may contain the active compounds of the invention, their derivatives, salts and hydrates thereof, in a form to be administered alone, but generally in a form to be administered in admixture with a pharmaceutical carrier selected with regard to the intended route of administration and standard pharmaceutical practice. Suitable carriers which can be used are, for example, diluents or excipients such as fillers, extenders, binders, emollients, wetting agents, disintegrates, surface active agents and lubricants which are usually employed to prepare such drugs depending on the type of dosage form.

Any suitable route of administration may be employed for providing the patient with an effective dosage of the compound of the invention their derivatives, salts and hydrates thereof. For example, oral, rectal, parenteral (subcutaneous, intramuscular, intravenous), transdermal, topical, ophthalmic, otic and like forms of administration may be employed. Dosage forms include (solutions, suspensions, etc) tablets, pills, powders, troches, dispersions, suspensions, emulsions, solutions, capsules, injectable preparations, patches, ointments, creams, lotions, shampoos and the like.

The prophylactic or therapeutic dose of the compounds of the invention, their derivatives, salts or hydrates thereof, in the acute or chronic management of disease will vary with the severity of condition to be treated, and the route of administration. In addition, the dose, and perhaps the dose frequency, will also vary according to the age, body weight and response of the individual patient. In general, the total daily dose range, for the compounds of the invention, the derivatives, salts or hydrates thereof, for the conditions described herein, is from about 200 mg to about 1500 mg, in single or divided doses. While intramuscular administration may be a single dose or up to 3 divided doses, intravenous administration can include a continuous drip. It may be necessary to use dosages outside these ranges in some cases as will be apparent to those skilled in the art. The term "an amount sufficient to eradicate such infections but insufficient to cause undue side effects" is encompassed by the above-described dosage amount and dose frequency schedule.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation.

The compositions of the present invention include compositions such as suspensions, solutions, elixirs, aerosols, and solid dosage forms.

Because of their ease of administration, tablets and capsules represent the most advantageous oral dosage unit form, in which case solid pharmaceutical carriers are employed. Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween (fatty acid ester of polyoxyethylenesorbitan), sodium lauryl sulfate, stearic acid monoglyceride, starch, and lactose, disintegration inhibitors such as white sugar, stearic acid glyceryl ester, cacao butter and hydrogenated oils, absorption promoters such as quaternary ammonium bases and sodium lauryl sulfate, humectants such as glycerol and starch, absorbents such as starch, lactose, kaolin, bentonite and colloidal silicic acid, and lubricants such as purified talc, stearic acid salts, boric acid powder, polyethylene glycol and solid polyethylene glycol.

The tablet, if desired, can be coated, and made into sugar-coated tablets, gelatin-coated tablets, enteric-coated tablets, film-coated tablets, or tablets comprising two or more layers.

If desired, tablets may be coated by standard aqueous or non-aqueous techniques. In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, gelatin, and semi-synthetic glycerides.

In one embodiment method for treating or preventing microbial infections in a human or an animal, comprising administering to said animal or human a therapeutically effective amount of a compound of Formula I or the pharmaceutical composition of compound of Formula I is provided. The microbial infections may be caused by Gram-positive, Gram-negative bacteria, aerobic, anaerobic bacteria, atypical bacteria or protozoa.

Abbreviations

Abbreviations which may be used in the descriptions of the schemes and the examples that follow are: Ac for acetyl; AIBN for azobis-isobutyronitrile; Bn for benzyl; Boc for t-butoxycarbonyl; Bu$_3$SnH for tributyltin hydride; Bz for benzoyl; CDI for carbonyldiimidazole; DBU for 1,8-diazabicyclo[5.4.0]undec-7-ene; DBN for 1,5-diazabicyclo[4.3.0]non-5-ene; DCC for 1,3-dicyclohexylcarbodiimide; DEAD for diethylazodicarboxylate; DIC for 1,3-diisopropylcarbodiimide; DMAP for dimethylaminopyridine; DMF for dimethyl formamide; DPPA for diphenylphosphoryl azide; EtOAc for ethyl acetate; KHMDS for potassium bis(trimethylsilyl)amide; LHMDS for Lithium bis(trimethylsilyl)amide; LDA for lithium diisopropyl amide; MeOH for methanol; Me$_2$S for dimethyl sulfide; MOM for methoxymethyl; NaN(TMS)$_2$ for sodium bis(trimethylsilyl)amide; NCS for N-chlorosuccinimide; NMO for 4-methylmorpholine N-oxide; PCC for pyridinium chlorochromate; PDC for pyridinium dichromate; Ph for phenyl; TEA for triethylamine; THF for tetrahydrofuran; TPP or PPh$_3$ for triphenylphosphine; TBS for tert-butyl dimethylsilyl; TMS for trimethylsilyl.

In a further embodiment is provided a process for the preparation of macrolide and ketolide compounds having Formula I, wherein the variables have the previously defined meanings, the method comprising the process will be better understood in connection with the following synthetic Schemes. The synthesis of the compounds of the invention can be broadly summarized as a. Synthesis of the novel macrolides bearing 11,12-γ-lactone
b. Synthesis of the novel ketolides
c. Further conversions to generate the compounds of Formula I.

a) Synthesis of the Novel Macrolides Bearing 11,12-γ-lactone

As depicted in the Scheme 1, erythromycin A or clarithromycin or derivatives of erythromycin and clarithromycin are used as the starting material for the reactions. All the above starting materials are used with optionally protected hydroxyl and/or amino groups with a suitable protecting group familiar to those skilled in the art. Exemplary protecting groups are, but not limited to silyl ethers such as triethylsilyl, trimethylsilyl, tert-butyldimethylsilyl, triisopropylsilyl. The protecting groups include benzyl, allyl, acetyl, benzoyl, pivalolyl and the like. For the amino protection, benzyloxycarbonyl, acetyl, tert-butoxycarbonyl (henceforth BOC) and the like may be used. The suitable macrolide starting material, depicted by compound (II) in the Scheme 1, is treated with triphosgene in a suitable solvent such as halogenated solvents such as dichloromethane, chloroform or THF in the presence of pyridine to provide the 11,12-carbonate (III, wherein R1, R2, R2' have the same meaning defined in Formula I).

Scheme 1

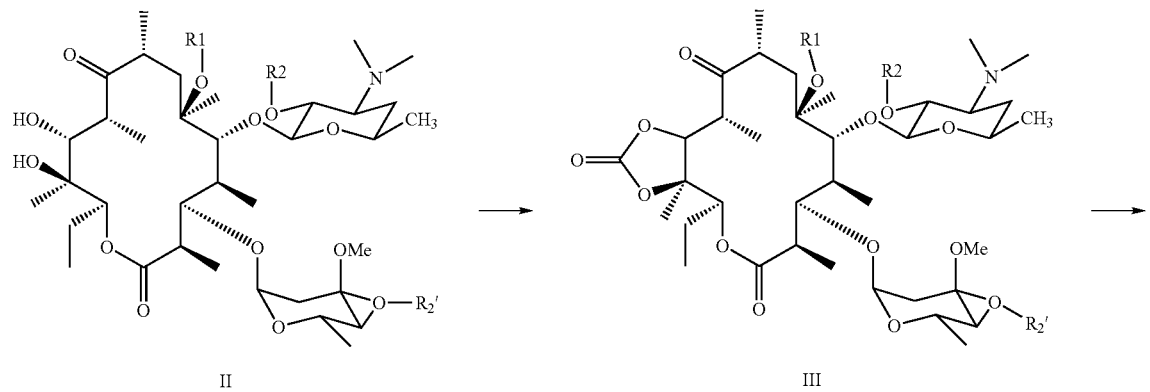

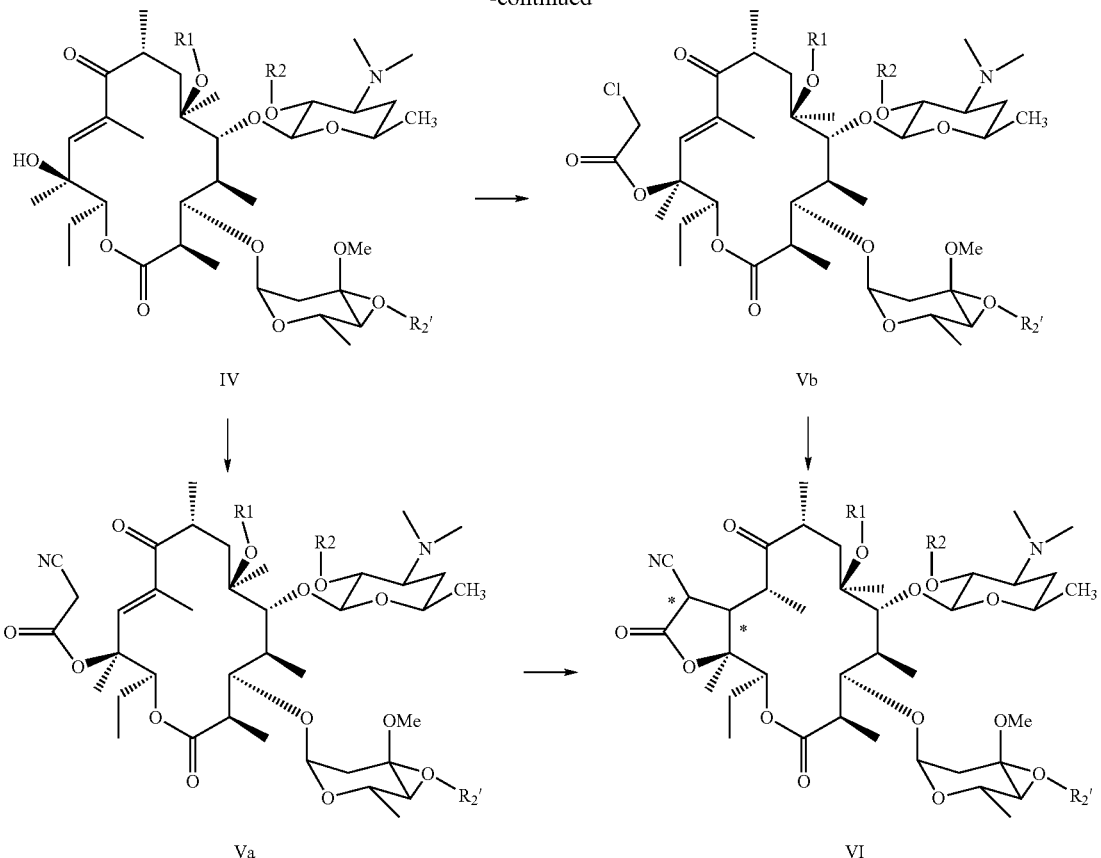

The compound III obtained from Scheme 1, is dissolved in solvent such as ethyl acetate, acetonitrile, tetrahydrofuran or mixtures thereof and treated with a base such as 1,8-diazabicyclo[5.4.0]undec-7-ene, KHMDS, LDA, triethylamine at 50-80° C., to give compound IV.

The compound IV is treated with cyanoacetic acid in presence of a ester coupling reagent such as DCC, 2,4,6-trichlorobenzoyl chloride, EEDQ, EDCI, Boc-Cl in a presence of a base such as pyridine, DMAP, N,N-Diisopropylethylamine, triethylamine and the like in a suitable solvent such as dichloromethane, acetonitrile, tetrahydrofuran, N,N-dimethylformamide or mixtures thereof to give compound Va. The compound Va is further treated with a base such as pyridine, DBU, DBN, LHMDS, LDA to give compound of Formula VI.

Alternatively, the compound IV, is dissolved in solvent such as dichloromethane or acetonitrile or tetrahydrofuran or N,N-dimethylformamide or mixtures thereof and treated with chloroacetic anhydride in presence of a base such as pyridine and dimethylamino pyridine at 5-40° C., to give compound Vb. The compound Vb, is dissolved in a solvent such as acetonitrile or tetrahydrofuran or N,N-dimethylformamide or DMSO or mixture thereof and treated with potassium cyanide at 15-40° C., to give compound VI.

The compound VI is dissolved in solvent such as tetrahydrofuran or methanol or ethanol or mixture thereof and treated with hydroxylamine hydrochloride in the presence of base such as sodium bicarbonate or sodium acetate or potassium hydroxide to give compound VII (Scheme 2).

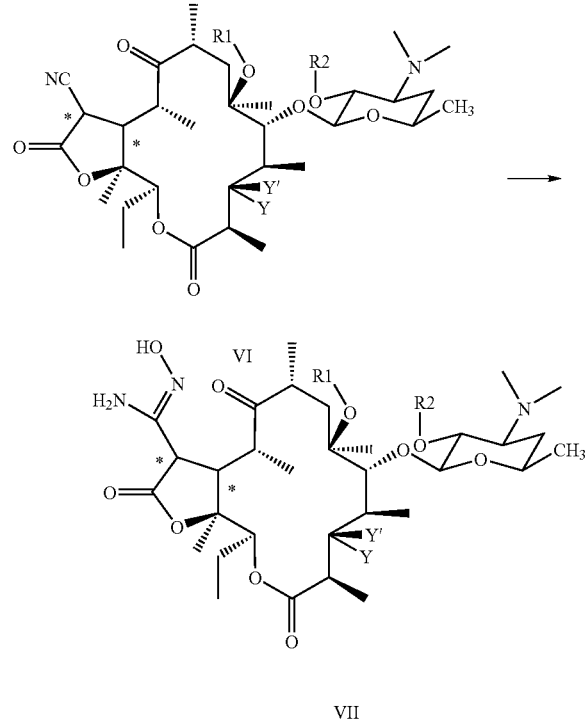

b) Synthesis of the Ketolide Derivatives:

For the synthesis of the C-3 ketolide, the cladinose sugar is removed by hydrolysis according to procedures described in the art.

The 3-O-cladinose sugar of the compound of Formula I-a is cleaved with an inorganic acid such as hydrochloric acid, sulphuric acid at temperature ranging from −10° C. to 60° C. for 0.5 to 24 h. to give compound VIII as shown in Scheme 3. Before derivatizing the generated C-3-hydroxyl, the 2'-OH group of the 5-desosamine is protected as shown in Scheme 3 by use of an acetyl group. The acetylation is done using acetyl chloride or acetic anhydride in presence or absence of a base in a suitable solvent such as acetone, acetonitrile or dichoromethane, at room temperature for 6-24 h to give compound (IX, $R_2$=COCH$_3$), Scheme 3. An alternate protecting group may also be used by treatment the compound VIII with reagents such as trialkylsilyl chloride benzoyl chloride, benzoic anhydride, benzyl chloroformate, hexamethyldisilazane.

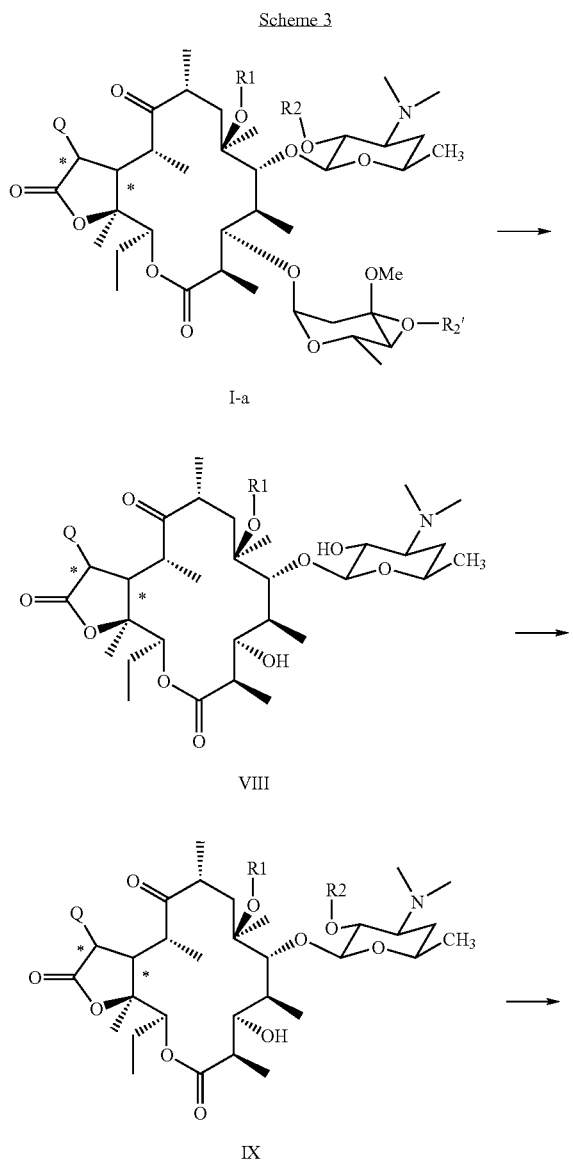

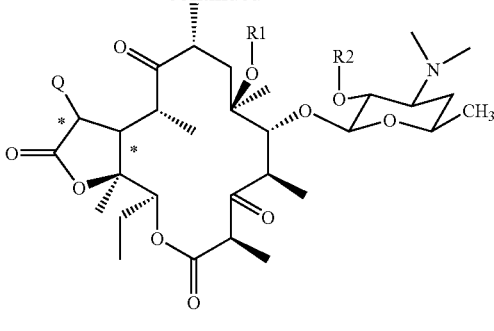

The conversion of the 3-hydroxy group to 3-ketone is accomplished by using a Corey-Kim oxidation with N-chlorosuccinimide-dimethyl sulphide (NCS-DMS) or a Moffat oxidation with carbodiimide-dimethylsulphoxide (DMSO) complex in the presence of pyridinium trifluoroacetate or Dess-Martin periodinane. Such name reactions are carried out according to general procedures described in the art. In general, the compound (IX, $R_2$=COCH$_3$ or $R_2$=TES), obtained in Scheme 3 is dissolved in a chlorinated solvent such as dichloromethane or chloroform and Dess-Martin periodinane reagent was added and stirred at an ambient temperature for about 0.5 to 1 h to get the corresponding 3-ketone compound X, Scheme 3.

c) Further Manipulations to Generate the Compounds of Formula I.

The manner in which the following procedures are to be used to provide the actual compounds listed in the table will be readily apparent to those persons skilled in the art of synthesis. The sequence of the reactions can be altered as will be readily apparent to those persons skilled in the art of synthesis. The examples described in the Experimental section later in this specification are illustrative and representative of how these procedures are to be used for all of the compounds listed in the table.

For the O-acylation of the amidoxime in the 11,12-γ-lactone ring i.e. the formation of compound XIIa or XIIb, the unsubstituted amidoxime is esterified with a suitable carboxylic acid reagent of the Formula $R_9$—COOH, wherein $R_9$ represents —(CH$_2$)$_m$—R$_5$, —(CH$_2$)$_m$—CH=CH—R$_5$, —(CH$_2$)$_m$—C≡C—R$_5$, —(CH$_2$)$_m$—B—R$_5$, —(CH$_2$)$_m$—CH=CH—B—R$_5$, —(CH$_2$)$_m$—C≡C—B—R$_5$, —(CH$_2$)$_m$—X—R$_6$, —(CH$_2$)$_m$—CH=CH—X—R$_6$, —(CH$_2$)$_m$—C≡C—X—R$_6$, wherein R$_5$, R$_6$, X, B and m are as defined above. A mixture of suitably substituted acid, a condensing agent such as EDC, EDCI, DCC or EEDQ, HBTU and 1-hydroxy-benzotriazole in a halogenated solvent such as chloroform or dichloromethane, acetonitrile, THF, DMF was stirred at a temperature between −10° C. to 45° C. Compound of Formula VIIa or VIIb was treated with the above mixture in the presence of a such as catalyst N,N-dimethylamino pyridine, at the temperature in the range of 0 to 45° C. to give compound of Formula XIa and XIb respectively (Scheme 4).

The macrolide compounds of Formula XIIa are obtained from the corresponding macrolides of Formula XIa by treating with a fluoride source such as tetrabutylammonium fluoride or HF-pyridine complex, preferably HF-pyridine complex in a suitable solvent such as dichloromethane or chloroform or acetonitrile or DMF, at a temperature in the range of 0° C. to 50° C.

For the ketolide compounds of Formula XIIb, the corresponding 3-hydroxyl compounds of Formula XIb are treated with an oxidizing agent as described above for the ketolides in Scheme 3, followed by deprotection of the 2'-hydroxyl of the desosamine sugar with a fluoride source as described above to afford ketolides of Formula XIIb, wherein all the variables are as defined above in Formula I.

Scheme 4

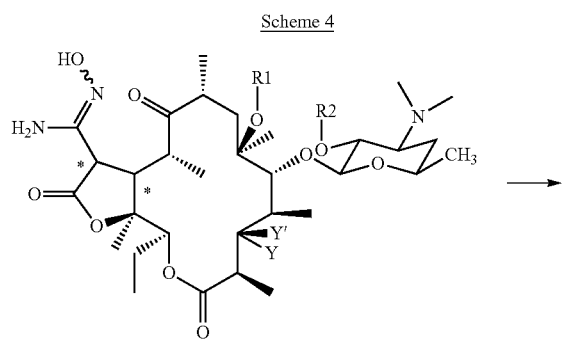

VIIa, Y' is H, Y is Ocladinose, R2, R2' is TES
VIIb, Y' is H, Y is OH, R2, is TES

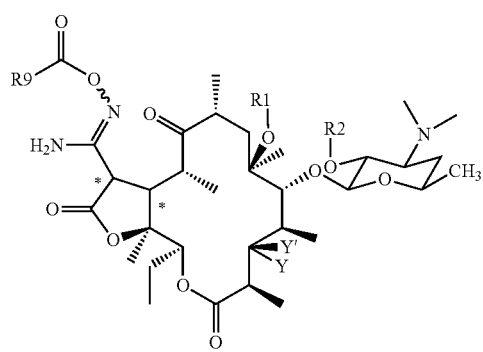

XIa, Y' is H, Y is Ocladinose, R2, R2' is TES
XIb, Y' is H, Y is OH, R2, is TES

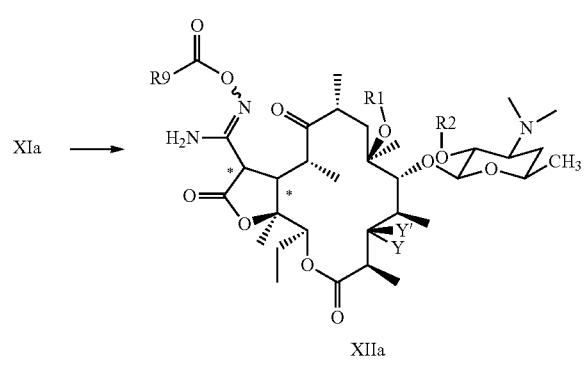

XIa →
XIb →

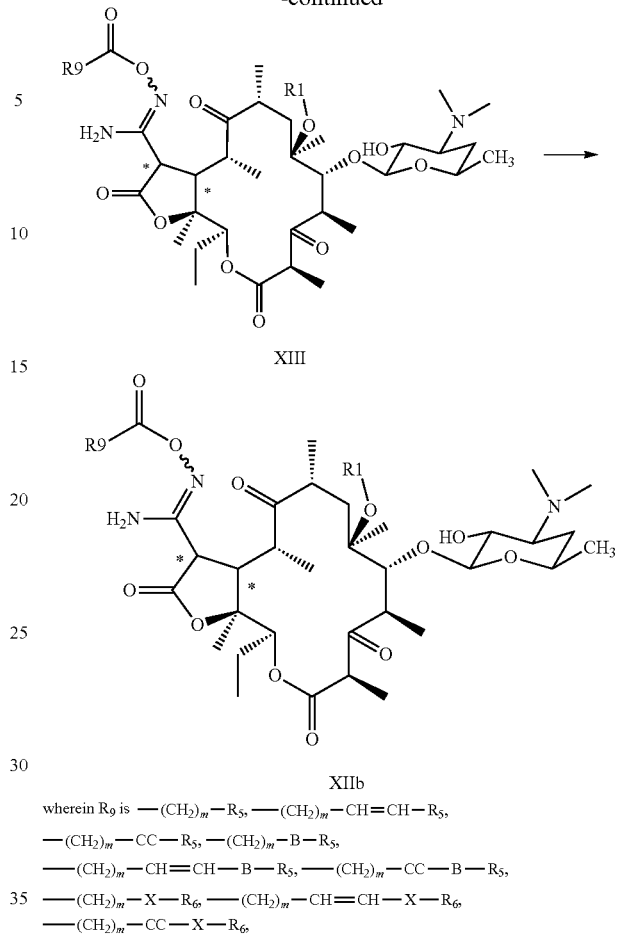

XIII

XIIb wherein $R_9$ is $—(CH_2)_m—R_5$, $—(CH_2)_m—CH=CH—R_5$,
$—(CH_2)_m—CC—R_5$, $—(CH_2)_m—B—R_5$,
$—(CH_2)_m—CH=CH—B—R_5$, $—(CH_2)_m—CC—B—R_5$,
$—(CH_2)_m—X—R_6$, $—(CH_2)_m—CH=CH—X—R_6$,
$—(CH_2)_m—CC—X—R_6$, The unsubstituted amidoxime was treated with a suitable isocyanate to obtain carbamates of Formula XVa or XVb as shown in Scheme 5.

Compound of Formula VIIa or VIIb was treated with isocyanate of Formula $R_9—N=C=O$, wherein $R_9$ represents $—(CH_2)_m—R_5$, $—(CH_2)_m—CH=CH—R_5$, $—(CH_2)_m—C≡C—R_5$, $—(CH_2)_m—B—R_5$, $—(CH_2)_m—CH=CH—B—R_5$, $—(CH_2)_m—C≡C—B—R_5$, $—(CH_2)_m—X—R_6$, $—(CH_2)_m—CH=C H—X—R_6$, $—(CH_2)_m—C≡C—X—R_6$, wherein $R_5$, $R_6$, X, B and m are as defined above, in a solvent such as chloroform or dichloromethane, at a temperature between 0 to 40° C., to afford the corresponding compound of Formula XIVa and XIVb respectively.

The macrolide compounds of Formula XVa are obtained from the corresponding macrolides of Formula XIVa by treating with a fluoride source such as tetrabutylammonium fluoride or HF-pyridine complex, preferably HF-pyridine complex in a suitable solvent such as dichloromethane or chloroform or acetonitrile or DMF, at a temperature in the range of 0° C. to 50° C.

For the ketolide compounds of Formula XVb, the corresponding 3-hydroxyl compounds of Formula XIVb are treated with a oxidizing agent as described above for the ketolides in Scheme 3, followed by deprotection of the 2'-hydroxyl of the desosamine sugar with a fluoride source as described above to afford ketolides of Formula XIVb, wherein all the variables are as defined above in Formula I.

Scheme 5

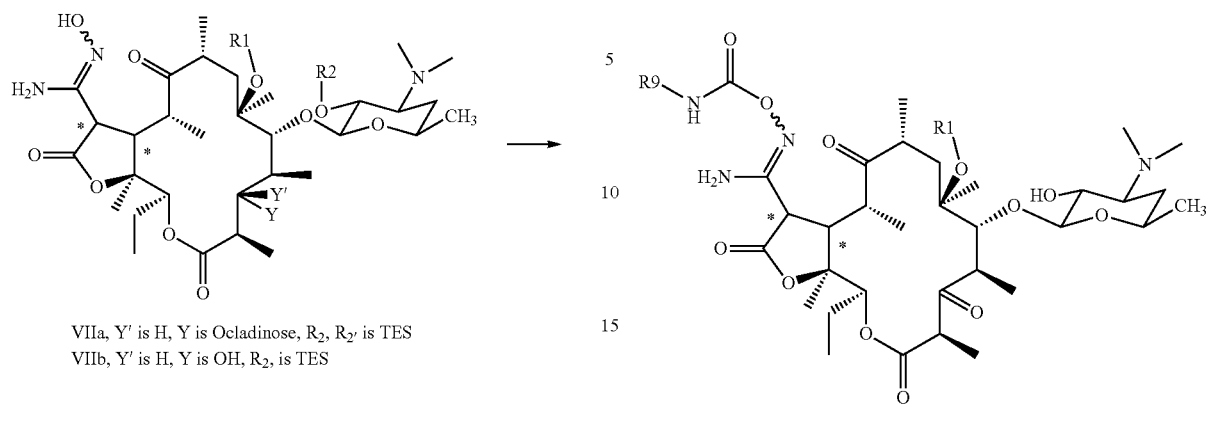

VIIa, Y' is H, Y is Ocladinose, $R_2$, $R_{2'}$ is TES
VIIb, Y' is H, Y is OH, $R_2$ is TES

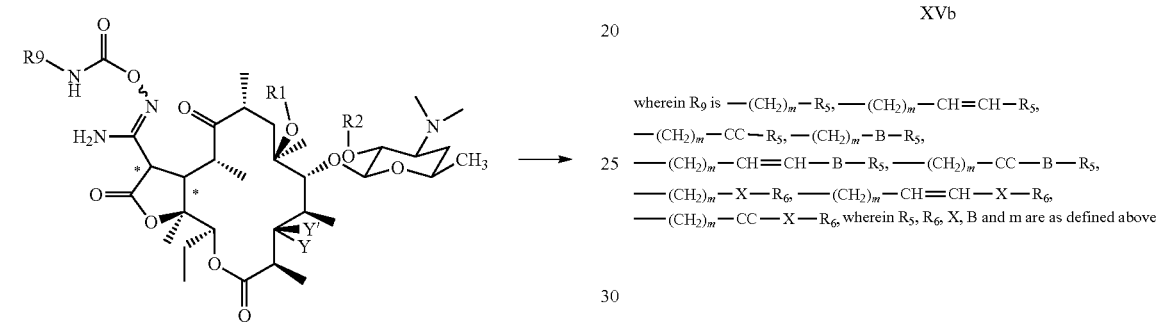

XIVa, Y' is H, Y is Ocladinose, $R_2$, $R_{2'}$ is TES
XIVb, Y' is H, Y is OH, $R_2$ is TES XIVa ⟶

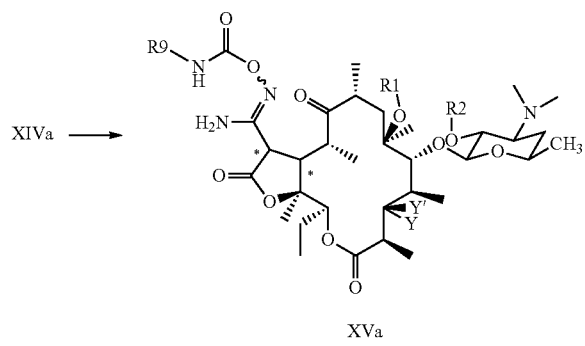

XVa

XIVb ⟶

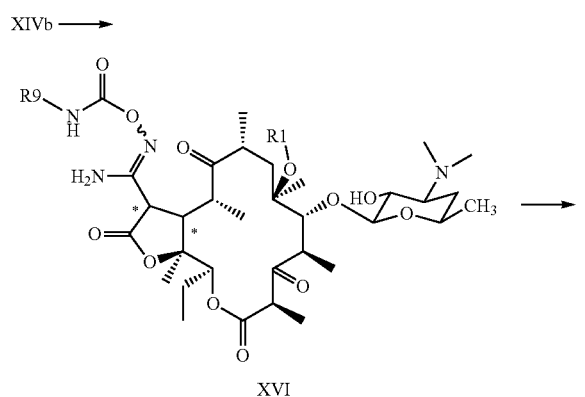

XVI

XVb wherein $R_9$ is —$(CH_2)_m$—$R_5$, —$(CH_2)_m$—CH═CH—$R_5$,
—$(CH_2)_m$—CC—$R_5$, —$(CH_2)_m$—B—$R_5$,
—$(CH_2)_m$—CH═CH—B—$R_5$, —$(CH_2)_m$—CC—B—$R_5$,
—$(CH_2)_m$—X—$R_6$, —$(CH_2)_m$—CH═CH—X—$R_6$,
—$(CH_2)_m$—CC—X—$R_6$, wherein $R_5$, $R_6$, X, B and m are as defined above For the O-alkylation of the amidoxime in the 11,12-γ-lactone ring i.e. the formation of macrolide or ketolide of Formula XVIIa or XVIIb as shown in Scheme 6, the compound of Formula VIIa or VIIb was treated with a suitable alkylating reagent of Formula halo-$R_9$ wherein $R_9$ represents —$(CH_2)_m$—$R_5$, —$(CH_2)_m$—CH═CH—$R_5$, —$(CH_2)_m$—C≡C—$R_5$—$(CH_2)_m$—B—$R_5$, —$(CH_2)_m$—CH═CH—B—$R_5$, —$(CH_2)_m$—C≡C—B—$R_5$, —$(CH_2)_m$—X—$R_6$, —$(CH_2)_m$—CH═CH—X—$R_6$, —$(CH_2)_m$—C≡C—X—$R_6$, wherein B, X, $R_5$, $R_6$ and m are as defined above and halo is a chlorine, bromine or iodine. The compound VIIa or VIIb was dissolved in a solvent such as benzene or toluene or xylene or dialkyl ether or DMF or THF or mixture thereof, at a temperature in the range of 0-100° C., in the presence of a base such as sodium hydride, potassium hydride or potassium carbonate or potassium hydroxide, optionally in the presence of phase transfer catalyst such as 18-crown-6-ether or trialkyl ammonium sulfate, to provide the compound XVIa and XVIb. The macrolide compounds of Formula XVIIa are obtained from the corresponding macrolides of Formula XVIa by treating with a fluoride source such as tetrabutylammonium fluoride or HF-pyridine complex, preferably HF-pyridine complex in a suitable solvent such as dichloromethane or chloroform or acetonitrile or DMF, at a temperature in the range of 0° C. to 50° C.

For the ketolide compounds of Formula XVIIb, the corresponding 3-hydroxyl compounds of Formula XVIb are treated with a oxidizing agent as described above for the ketolides in Scheme 3, followed by deprotection of the 2'-hydroxyl of the desosamine sugar with a fluoride source as described above to afford ketolides of Formula XVIIb, wherein all the variables are as defined above in Formula I.

Scheme 6

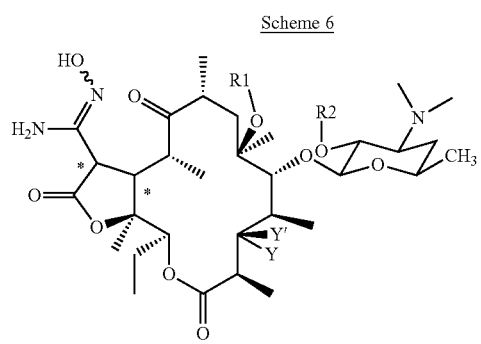

VIIa, Y' is H, Y is Ocladinose, R2, R2' is TES
VIIb, Y' is H, Y is OH, R2, is TES

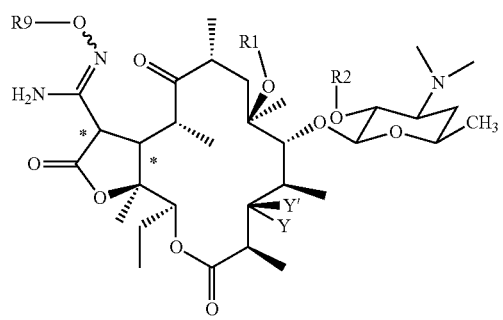

XVIa, Y' is H, Y is Ocladinose, R2, R2' is TES
XVIb, Y' is H, Y is OH, R2, is TES XIVa ⟶

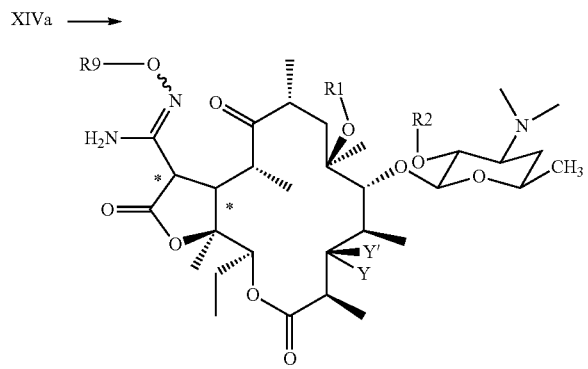

XVIIa

XVIb ⟶

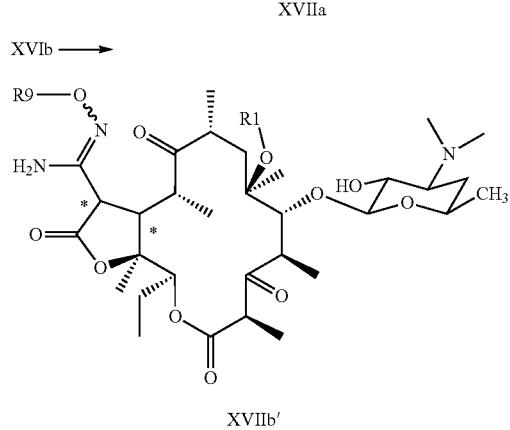

XVIIb'

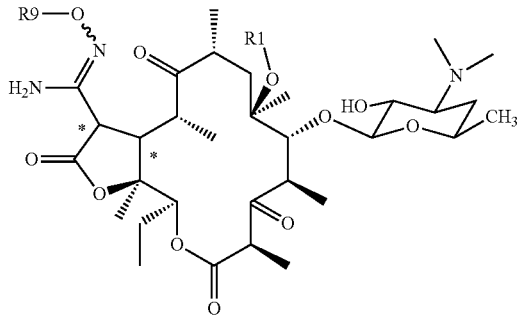

XVIIb wherein $R_9$ is —$(CH_2)_m$—$R_5$, —$(CH_2)_m$—CH=CH—$R_5$,
—$(CH_2)_m$—CC—$R_5$, —$(CH_2)_m$—B—$R_5$,
—$(CH_2)_m$—CH=CH—B—$R_5$, —$(CH_2)_m$—CC—B—$R_5$,
—$(CH_2)_m$—X—$R_6$, —$(CH_2)_m$—CH=CH—X—$R_6$,
—$(CH_2)_m$—CC—X—$R_6$ Compounds of Formula XXa or XXb are prepared as shown in Scheme 7 by using Heck coupling reaction. Compound of Formula XVIIIa or XVIIIb, are treated a halo-aryl reagent of Formula halo-$R_5$ or halo-X—$R_6$ in presence of a palladium (II) or palladium (0) catalyst such as palladium acetate ($Pd(OAc)_2$) in presence of a phosphine reagent such as triphenylphosphine, tri(o-totyl)phosphine and a base such as triethylamine, sodium carbonate, sodium bicarbonate, or in presence of sodium acetate, in a suitable solvent such as N,N-dimethylformamide (DMF), acetonitrile, tetrahydrofuran (THF) to give the corresponding compound of Formula XIXa or XIXb respectively as shown in Scheme 7, wherein G is —$(CH_2)_m$—, -A-$(CH_2)_m$—; U is —$R_5$ or —X—$R_6$, The macrolide compounds of Formula XXa are obtained from the corresponding macrolides of Formula XIXa by treating with a fluoride source such as tetrabutylammonium fluoride or HF-pyridine complex, preferably HF-pyridine complex in a suitable solvent such as dichloromethane, chloroform, acetonitrile, DMF or mixtures thereof, at a temperature in the range of 0° C. to 50° C.

Scheme 7

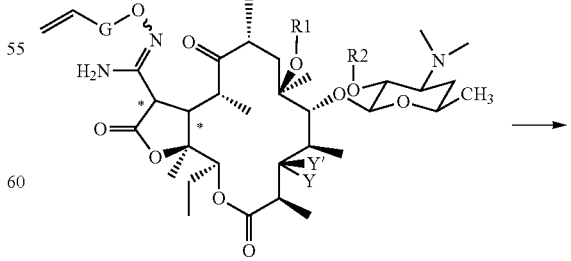

XVIIIa, Y' is H, Y is Ocladinose, R2, R2' is TES
XVIIIb, Y' is H, Y is OH, R2, is TES

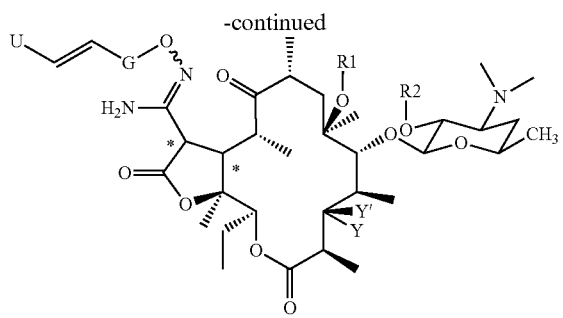

XIXa, Y' is H, Y is Ocladinose, R2, R2' is TES
XIXb, Y' is H, Y is OH, R2, is TES XIXa →

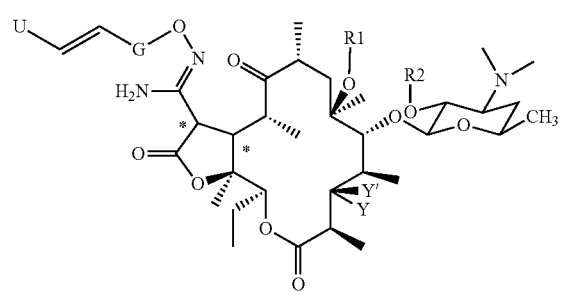

XXa

XIXb →

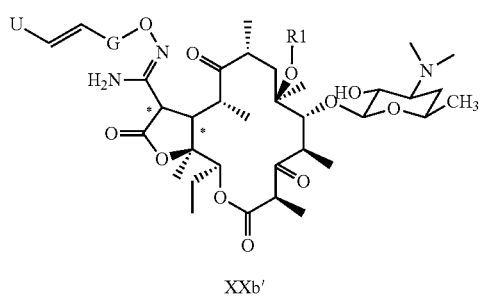

XXb'

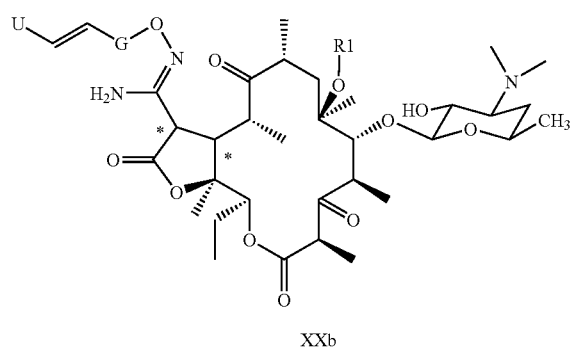

XXb

For the ketolide compounds of Formula XXb, the corresponding 3-hydroxyl compounds of Formula XIXb are treated with an oxidizing agent as described above for the ketolides in Scheme 3, followed by deprotection of the 2'-hydroxyl of the desosamine sugar with a fluoride source as described above to afford ketolides of Formula XXb, wherein all the variables are as defined above in Formula I.

Compounds of Formula XXIIIa or XXIIIb are prepared as shown in Scheme 8 by using Sonagashira coupling reaction. Compound of Formula XXIa or XXIb are treated a halo-aryl reagent of Formula halo-$R_5$ or halo-X—$R_6$, wherein $R_5$, $R_6$ are as defined above, in presence of a palladium catalyst such as dichlorobis(triphenylphosphine)palladium (II) or $Pd(PPh_3)_4$ in presence of a base such as triethylamine, diethyl amine, butylamine, piperidine, in a suitable solvent such as N,N-dimethylformamide (DMF), acetonitrile, tetrahydrofuran (THF) to give the compound of Formula XXIIa or XXIIb respectively as shown in Scheme 8.

The macrolide compounds of Formula XXIIIa are obtained from the corresponding macrolides of Formula XXIIa by treating with a fluoride source such as tetrabutylammonium fluoride or HF-pyridine complex, preferably HF-pyridine complex in a suitable solvent such as dichloromethane or chloroform or acetonitrile or DMF, at a temperature in the range of 0° C. to 50° C.

For the ketolide compounds of Formula XXIIIb, the corresponding 3-hydroxyl compounds of Formula XXIIb are treated with an oxidizing agent as described above for the ketolides in Scheme 3, followed by deprotection of the 2'-hydroxyl of the desosamine sugar with a fluoride source as described above to afford ketolides of Formula XXIIIb, wherein all the variables are as defined above in Formula I.

Scheme 8

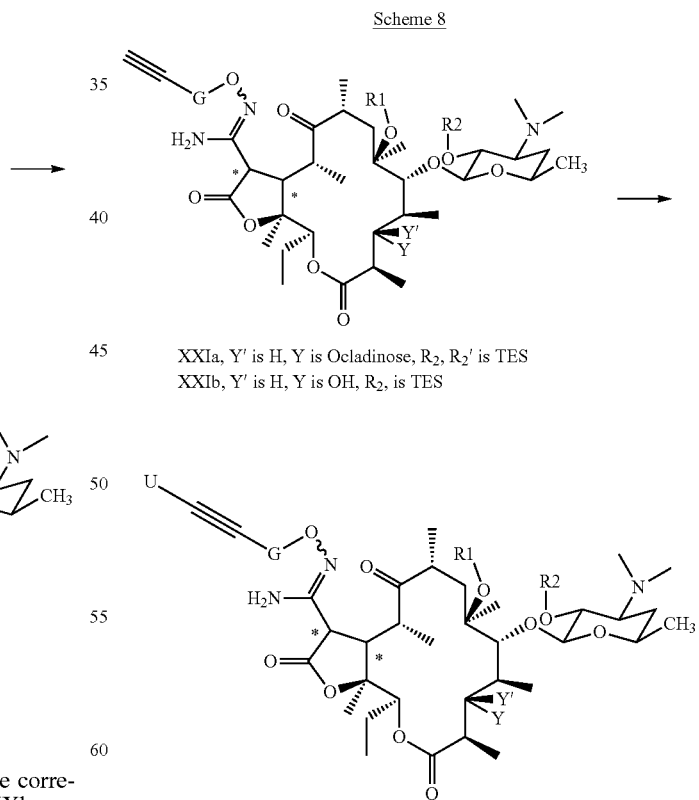

XXIa, Y' is H, Y is Ocladinose, $R_2$, $R_2'$ is TES
XXIb, Y' is H, Y is OH, $R_2$, is TES XXIIa, Y' is H, Y is Ocladinose, $R_2$, $R_2'$ is TES
XXIIb, Y' is H, Y is OH, $R_2$, is TES -continued XXIIa ⟶

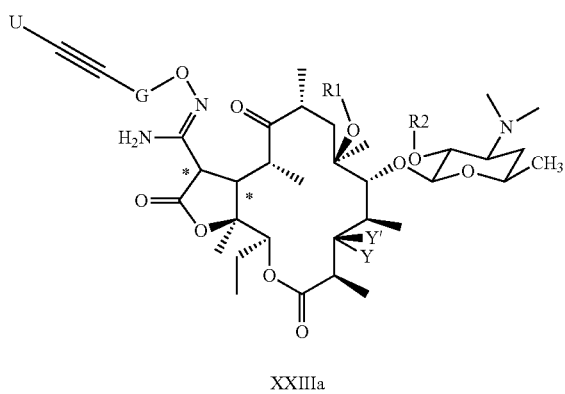

XXIIIa

XXIIb ⟶

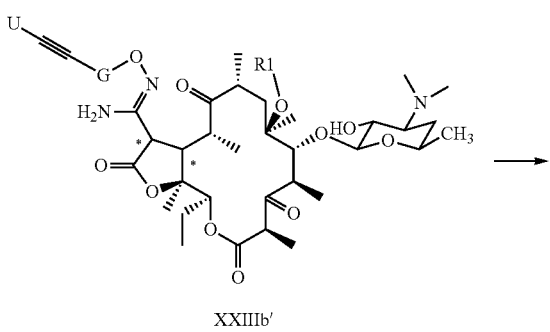

XXIIIb'

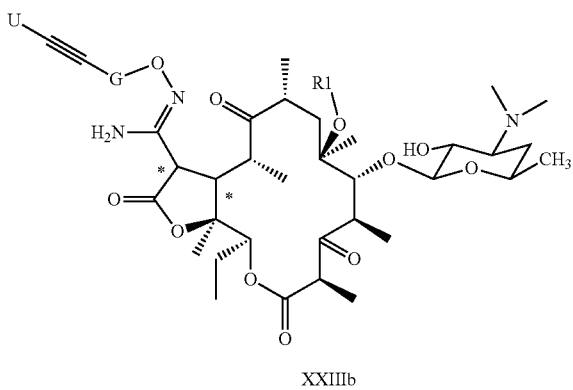

XXIIIb wherein G is —(CH$_2$)$_m$—, —A—(CH$_2$)$_m$—;
U is —R$_5$, —X—R$_6$,

The macrolide or ketolide of Formula XXIVa or XXIVb, wherein T is —(CH$_2$)$_m$—CH=CH—R$_5$, —(CH$_2$)$_m$—C≡C—R$_5$, -A-(CH$_2$)$_m$—CH=CH—R$_5$, -A-(CH$_2$)$_m$—C≡C—R$_5$, —(CH$_2$)$_m$—CH=CH—X—R$_6$, —(CH$_2$)$_m$—C≡C—X—R$_6$, -A-(CH$_2$)$_m$—CH=CH—X—R$_6$, -A-(CH$_2$)$_m$—C≡C—X—R$_6$, are treated with a hydrogenating catalyst such as 10% Pd/C, 5% Pd/C or 20% Pd(OH)$_2$ in presence of a hydrogen source such as hydrogen gas, ammonium formate, to give the corresponding compounds saturated compounds.

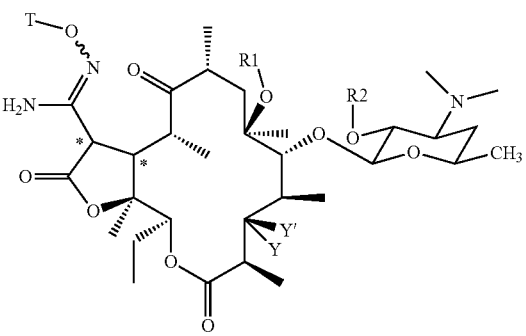

XXIVa, Y' is H, Y is Ocladinose,
XXIVb, Y', Y together C=O

Compound of Formula VIa or VIb is treated with a suitable reagent such as azidotrimethylsilane, sodiumazide in presence of catalyst such as tributyltinoxide to afford the corresponding tetrazol compound of Formula XXVa or XXVb. The tetrazol may be further alkylated using suitable alkylating reagent of Formula R$_3$-halo to afford the corresponding alkylated tetrazole derivatives, wherein R$_3$ is as defined above.

Compound of Formula VIa or VIb is treated with a suitable diamine such as ethylenediamine or propylenediamine in presence of sulphur at a temperature in the range of 100-150° C. to afford the corresponding dihydro imidazolyl compound of Formula XXVa or XXVb.

Compound of Formula VIIa or VIIb is treated with N,N-dimethylformamide dimethylacetal or trifluoroacetic anhydride, optionally in presence of a base such as triethylamine to afford the corresponding [1,2,4]-oxadiazole derivatives of Formula XXVa or XXVb.

The macrolide compounds of Formula XXVIa are obtained from the corresponding macrolides of Formula XXVa by treating with a fluoride source such as tetrabutylammonium fluoride or HF-pyridine complex, preferably HF-pyridine complex in a suitable solvent such as dichloromethane or chloroform or acetonitrile or DMF, at a temperature in the range of 0° C. to 50° C.

For the ketolide compounds of Formula XXVIb, the corresponding 3-hydroxyl compounds of Formula XXVb are treated with an oxidizing agent as described above for the ketolides in Scheme 9, followed by deprotection of the 2'-hydroxyl of the desosamine sugar with a fluoride source as described above to afford ketolides of Formula XXVIb, wherein all the variables are as defined above in Formula I.

Scheme 9
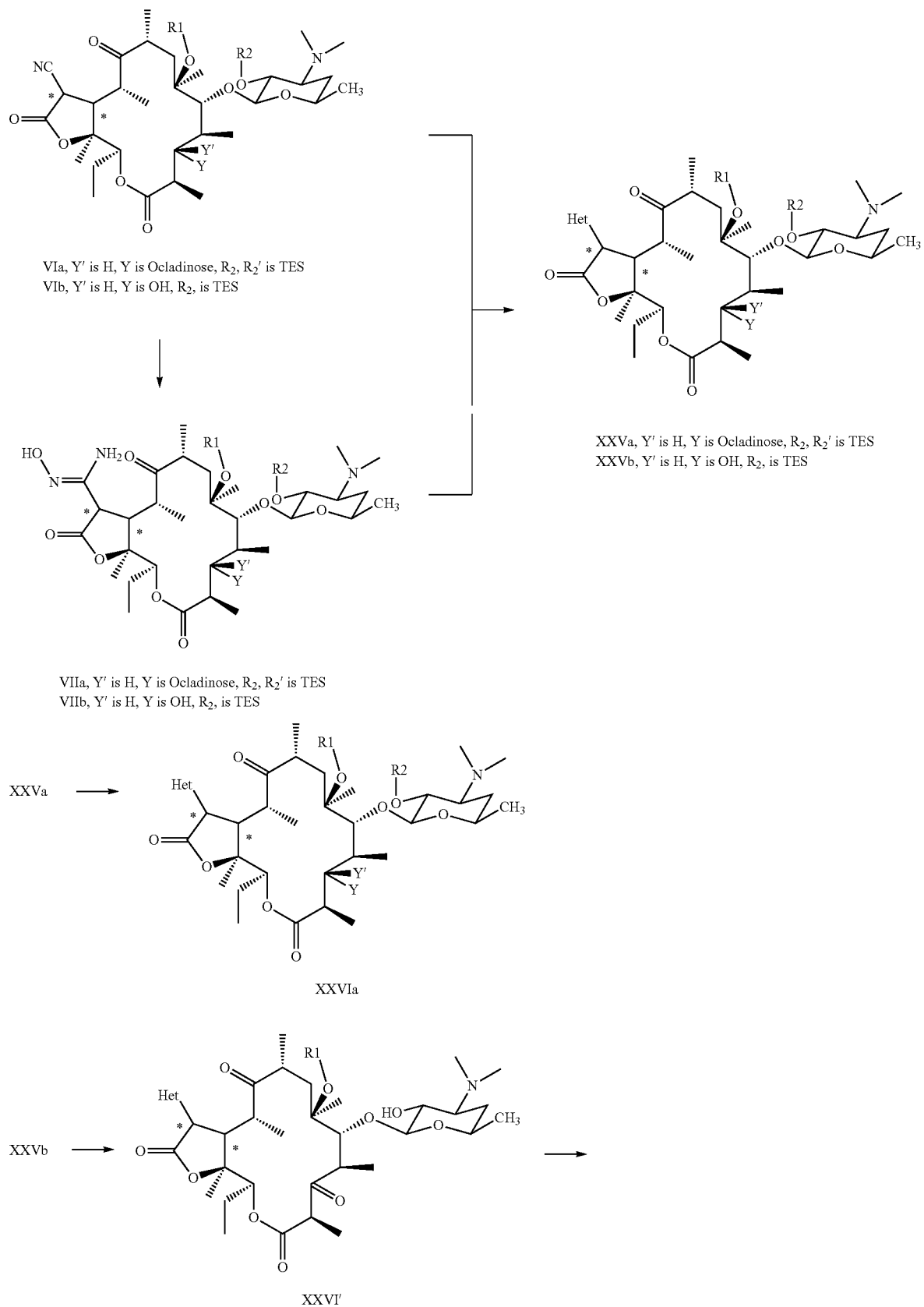
VIa, Y' is H, Y is Ocladinose, R₂, R₂' is TES
VIb, Y' is H, Y is OH, R₂, is TES
VIIa, Y' is H, Y is Ocladinose, R₂, R₂' is TES
VIIb, Y' is H, Y is OH, R₂, is TES
XXVa, Y' is H, Y is Ocladinose, R₂, R₂' is TES
XXVb, Y' is H, Y is OH, R₂, is TES
XXVa →
XXVIa
XXVb →
XXVI'

-continued

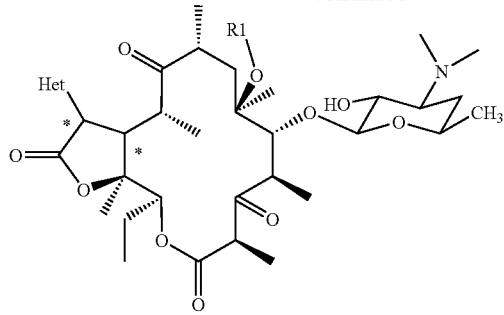

XXVIb

Biological Activity

The compounds of this invention are useful antimicrobial agents, effective against various human and veterinary pathogens, including multiple-resistant staphylococci and streptococci, enteroccoci, as well as anaerobic organisms such bacteroides and *clostridia* species, and acid resistant organisms such as *Mycobacterium tuberculosis* and *Mycobacterium avium*.

Test Example 1

MIC Test Method: Overnight grown cultures of *S. aureus* organisms in Tryptic Soya broth were diluted in Mueller Hinton Broth to give optical density matching with MacFarland tube 0.5 standard. Cultures were further diluted 1:10 in Mueller Hinton broth. Using Denley's mutipoint inoculator, $10^4$ cells were deposited on Mueller Hinton agar (Difco) containing range of 2 fold dilutions of test compounds. These plates were incubated for 24 hrs at 35° C. and MIC results recorded. MIC is defined as minimum drug concentration that inhibits test organisms. For determining MIC of test compounds against *Streptococcus pneumoniae*, Mueller Hinton agar containing 5% sheep blood was employed. The following strains were used to screen the compounds of invention. The compounds inhibited the growth of these bacteria with MIC's in the range of about 0.03 μg/mL to about 64 μg/mL.

| Strain |
| --- |
| *Staphylococcus aureus* ATCC 25923 |
| *Staphylococcus aureus* 014 |
| *Staphylococcus epidermidis* 110 |
| *Staphylococcus haemolyticus* ATCC 25923 |
| *Enterococcus faecalis* 401 |
| *Enterococcus faecium* 303 |
| *Streptococcus pneumoniae* 49619 |
| *Streptococcus pneumoniae* 706 |
| *Streptococcus pyogenes* 801 |
| *Streptococcus pyogenes* 805 |
| *Haemophilus influenzae* 49247 |
| *Mycobacterium tuberculosis* |
| *Mycobacterium avium* |

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, Formulations and/or methods of the invention may be made.

EXAMPLES

The following examples describe in detail the chemical synthesis of some of the representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

Example 1

Compound III of Scheme 1, $R_1$ is $CH_3$, $R_2$, $R_{2'}$ is Triethylsilyl

Step A: To a stirred solution of 6-methyl erythromycin A (15 g, 20.1 mmol) in anhydrous acetonitrile (120 ml) cooled to 0° C. Triethyl amine (19.5 ml, 140 mmol), DMAP (12.25 g, 100 mmol) and chloro triethyl silane (20 ml, 120 mmol) were added under nitrogen atmosphere. The resulting mixture was stirred at 25-30° C. temperature for 3 hr. Then water (120 ml) was added, the solid precipitated was filtered under suction. The wet cake was stirred with methanol (50 ml) at 25-30° C. temperature for 1 hr and filtered under suction, dried to provide step-1 product 2',4"-Di-TES-6-O-methyl-erythromycin A as white solid in 80% (16 g) yield. MS: m/z: 976.8 (M+1).

Step B: To a solution of product obtained in above step (10 g, 10.2 mmol) in anhydrous dichloromethane (70 ml) was added pyridine (5 ml, 61.2 mmol) and followed by triphosgene (3.04 g, 10.2 mmol) at 0° C. under an inert atmosphere. The reaction mixture was further stirred at 0-5° C. for 0.5 h. To the reaction mixture water (15 ml) was added, the organic layer was separated. The organic layer was dried ($Na_2SO_4$) and evaporated under reduced pressure to give the title compound (9.7 g) as white solid. m\z ([MH]$^+$)=1002.5.

Example 2

Compound IV of Scheme 1, $R_1$ is $CH_3$, $R_2$, $R_{2'}$ is Triethylsilyl

To a solution of Example 1 (9.5 g, 9.5 mmol) in ethyl acetate (70 ml), 1,8-diazabicyclo[5.4.0]undec-7-ene (3 ml, 20 mmol) was added at an ambient temperature and the reaction mixture was further heated under reflux for 6 h. The reaction mixture was cooled to room temperature and water (15 ml) was added to it and stirred for 10 min. The organic layer was separated, dried and evaporated under reduced pressure to afford the title compound (9.3 g). m\z ([MH]$^+$)=958.

Example 3

Compound Vb of Scheme 1, $R_1$ is $CH_3$, $R_2$, $R_{2'}$ is Triethylsilyl

To the solution of Example 2 (9.3 g, 9.7 mmol) in anhydrous dichloromethane (30 ml) was added pyridine (4.7 ml, 58.2 mmol), DMAP (0.6 g, 4.8 mmol) and followed by chloroacetic anhydride (3.7 g, 21.3 mmol) at 0° C. After completion of addition it was allowed to come to room temperature and stirred further for 3 h. To the reaction mixture water (30 ml) was added and stirred vigorously for 10 min. and separated the organic layer. The organic layer was then washed with a saturated solution of sodium bicarbonate followed by the brine. The organic layer was dried ($Na_2SO_4$) and upon removal of the solvent under reduced pressure a gummy mass was obtained which was taken into the methanol and stirred for 2 h to provide the title compound (8 g). m\z ([MH]$^+$)=1034.

Example 4

Compound VI of Scheme 1, $R_1$ is $CH_3$, $R_2$, $R_{2'}$ is Triethylsilyl

Method 1:

Example 3 (6 g, 5.8 mmol) was dissolved into N,N-dimethylformamide (20 ml) and to it potassium cyanide (0.6 g, 8.7 mmol) was added carefully under inert atmosphere at room temperature. The reaction mixture was further stirred for 2 h. The reaction mixture was filtered and poured into the 5% sodium bicarbonate solution (30 ml), the cream color solid separated out was filtered and washed successively by solution of ferrous sulphate and water. The crude solid obtained was crystallized from dichloromethane and n-hexane to provide the title compound (5.15 g). m\z ([MH]$^+$)=1025.

Method 2:

Step A: Compound Va of Scheme 1, $R_1$ is $CH_3$, $R_2$, $R_2$ is triethylsilyl: To the stirred solution of cyanoacetic acid (1.11 g, 13.1 mmol) in anhydrous dichloromethane (50 ml), 2,4,6-trichlorobenzoyl chloride was added at 0° C. N,N-Diisopropylethylamine (2.05 ml, 13.1 mmol) was added to the reaction mixture and it was stirred at 0° C. for 30 min. Example 2 (5 gm, 5.3 mmol) and N,N-diisopropylethylamine (2.05 ml, 13.1 mmol) were added to the reaction mixture and it was stirred at 25-30° C. temperature for 24 hr. To the reaction mixture was quenched by addition of aqueous solution of saturated sodium bicarbonate (50 ml) and stirred vigorously for 10 min. Organic layer was separated. The organic layer was washed with a water (50 ml), dried over $Na_2SO_4$ and solvent was evaporated under vacuum to afford yellow foam. The foam was stirred with acetonitrile at 0-5° C. and filtered to give step-4 product as a pale yellow solid in 70% (3.7 gm) yield. MS: m\z: 1025.7 (M+1).

Step B: To the stirred solution of product obtained in above step (3.6 g, 3.51 mmol) in N,N-dimethylformamide (15 ml), 1,8-diazabicyclo[5.4.0]undec-7-ene (0.545 g. 3.51 mmol) added at 25-30° C. temperature and stirred for 1 hr. Reaction mixture was diluted with water (50 ml) and the solid was filtered under suction to afford title compound in 40% (1.5 g) yield. MS: m\z: 1025.7 (M+1).

Example 5

Compound VII of Scheme 2, $R_1$ is $CH_3$, $R_2$, $R_{2'}$ is Triethylsilyl, Y' is H, Y is O-cladinose To a solution of Example 4 (5 g, 4.8 mmol) in methanol (25 ml), hydroxylamine hydrochloride (3.7 g, 53.7 mmol) and sodium bicarbonate (4.6 g, 54.6 mmol) was added and heated under reflux for 15 h. The solid separated out was filtered and washed with water. The crude solid obtained was purified by recrystallization from methanol to afford the title compound as white solid (4.3 g). m\z ([MH]$^+$)=1058.

Example 6

Compound IX of Scheme 3, $R_1$ is $CH_3$, $R_2$ is Triethylsilyl, Q is CN

To a solution of Example 4 (10 g, 9.7 mmol) in acetonitrile (40 ml), a 2N HCl (10 ml) was slowly added at 0° C. The reaction mixture was further stirred at room temperature for 4 h. It was then cooled to 0° C. and the pH of the solution was brought to 8 by slow addition of a saturated solution of sodium bicarbonate. The aqueous layer was extracted into chloroform (3×25 ml). The combined organic layer was dried ($Na_2SO_4$) and evaporated under reduced pressure to furnish the crude solid. The solid obtained was purified by column chromatography over silica gel using chloroform:methanol (7:3) as an eluent to provide a white solid (6 g). In this reaction condition the hydroxyl protecting group of desosamine sugar was cleaved, therefore we have again protected the hydroxyl group by using the following procedure. The deprotected solid (6 g, 9.4 mmol) was taken into acetonitrile:N,N-dimethylformamide (8:2, 30 ml). To this solution triethylamine (5.2 ml, 37.6 mmol), DMAP (4.5 g, 37.6 mmol) followed by chlorotriethylsilane (6.3 ml, 37.6 mmol) was added at room temperature and stirred for 3 h. To the reaction mixture water (50 ml) was added and it was extracted into n-hexane (3×40 ml). The combined organic layer was dried ($Na_2SO_4$) and evaporated to give the gummy mass, which on trituration with n-pentane provided the title compound as a white solid (6 g). m\z ([MH]$^+$)=753.

Example 7

Compound VII of Scheme 2, $R_1$ is $CH_3$, $R_2$ is Triethylsilyl, Y is OH, Y' is H Using the Example 6 (0.5 g) and following the same procedure as described for the Example 5, the title compound obtained a white solid (0.5 g). m\z ([MH]$^+$)=786.

Example 8

Compound X of Scheme 3, $R_1$ is $CH_3$, $R_2$ is Triethylsilyl, Q is CN

The Example 6 (6 g, 7.9 mmol) was dissolved in dichloromethane (60 ml). To the reaction mixture a solution Dess-Martin periodinane (15% in DCM, 27 ml, 9.5 mmol) was added under an inert atmosphere. The reaction mixture was stirred at room temperature for 5 min. and a solution of $Na_2S_2O_3$ (10% in saturated aqueous solution of sodium bicarbonate, 60 ml) was added and stirred for 10 min. The organic layer was separated and the aqueous layer was extracted with dichloromethane (3×15 ml) and the combine organic layer was dried ($Na_2SO_4$). The removal of the solvent under reduced pressure provided the crude solid, which was purified by column chromatography over silica gel using n-hexane:

EtOAc (8:2) as an eluent. The title compound was obtained a white solid (3.5 g). m\z ([MH]⁺)=751.

Example 9

Compound VII of Scheme 2, $R_1$ is $CH_3$, $R_2$ is Triethylsilyl, Y, Y' Together C=O Using the Example 8 (3.5 g, 4.6 mmol) and following the same procedure as described for the Example 5, the title compound obtained a white solid (3.5 g). m\z ([MH]⁺)=784.

Example-10

Compound of Formula I-c, $R_1$ is $CH_3$, T is H

To the solution of Example 5 (0.950 g, 0.89 mmol) in anhydrous THF (25 ml) was added 70% hydrogen fluoride in pyridine (77 µl, 2.7 mmol). The reaction mixture was stirred at an ambient temperature under inert atmosphere for 14 h. To the reaction mixture water (15 ml) was added and extracted with ethyl acetate (3×15 ml). The combined organic layer was dried ($Na_2SO_4$) and evaporated under reduced pressure. The thick liquid on trituration with n-pentane furnished the title compound (0.582 g) as a white solid. MS 830 (M+H)⁺.

Example-11

Compound of Formula I-b where Het is 1H-tetrazol-5-yl

Step A: To the stirring solution of Example 4 (29.3 mmol) in toluene was added tributyltinoxide (0.25 eq) and azidotrimethylsilane (2 eq). The reaction mixture was heated at 90° C. for 16-20 hours. The reaction mixture was concentrated and purified using silica gel column chromatography (Ethyl acetate:Hexane 1:1). Yield 70%.

Step C: To the stirring solution of compound obtained in Step B (0.36 mmol) in tetrahydrofuran was added HF-Pyridine complex (3.5 eq) and stirred it for 16 hours. The reaction mixture was concentrated and water was added. The product was extracted in chloroform. Yield 80%. Yield: Mass: m/z: 840.1 (M+H)⁺, M. P. 162-164° C.

Example-12

Compound of Formula I-b where Het is 2-(1-methoxy-ethoxymethyl)-1H-tetrazol-5-yl

Example-13

Compound of Formula I-b where Het is 2-(2-methoxy-ethoxymethyl)-2H-tetrazol-5-yl Step A: To the stirring solution of Example 4 (29.3 mmol) in toluene was added tributyltinoxide (0.25 eq) and azidotrimethylsilane (2 eq). The reaction mixture was heated at 90° C. for 16-20 hours. The reaction mixture was concentrated and purified using silica gel column chromatography (Ethyl acetate:Hexane 1:1). Yield 70%.

Step B: To the stirring solution of the compound obtained in above step A (0.93 mmol) in acetone was added TEA (1.3 eq) and MEM-Cl (1.2 eq) and heated it at reflux temperature for 1 hours. The reaction mixture was concentrated and water was added. Filtered the solid residue and dried it over high vacuo. It was a mixture of two regio isomers. It was then separated using 100-200-mesh silica gel column chromatography. Yield 42%.

Step C: To the stirring solution of compound obtained in Step B (0.36 mmol) in tetrahydrofuran was added HF-Pyridine complex (3.5 eq) and stirred it for 16 hours. The reaction mixture was concentrated and water was added. The product was extracted in chloroform. Yield 80%. Yield: Isomer-A: Mass: m/z: 928 (M+H). M.P. 210-212° C., Isomer-B: 190 mg Mass: m/z: 928 (M+H)⁺, M. P. 150-152° C.

Following examples were prepared by using above procedure and by using reactant A.

Formula I-b

| Example | Het | Reactant (A) | Mp (° C.) | Mass (M + 1) |
|---|---|---|---|---|
| 14 | 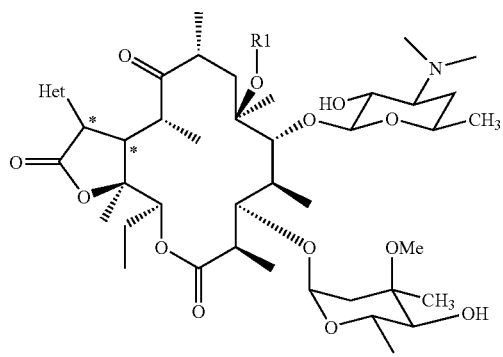 | Tetrazol-2-yl-acetic acid ethyl ester | 150-154 | 926.11 |

Formula I-b

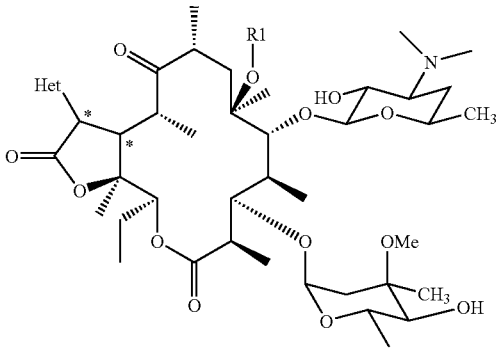

| Example | Het | Reactant (A) | Mp (° C.) | Mass (M + 1) |
|---|---|---|---|---|
| 15 | H₂N-C(=O)-CH₂-N(tetrazole) | 2-Tetrazol-2-yl-acetamide | 198-200 | 897.1 |
| 16 | NC-CH₂-N(tetrazole) (2-yl) | Tetrazol-2-yl-acetonitrile | 218-220 | 879.1 |
| 17 | NC-CH₂-N(tetrazole) (1-yl) | Tetrazol-1-yl-acetonitrile | 202-204 | 879.1 |
| 18 | allyl-N(tetrazole) | 2-Allyl-2H-tetrazole | 188-190 | 880.1 |
| 19 | (3-fluorophenyl)-N(Me)-C(=O)-CH₂-N(tetrazole) | Tetrazole-2-carboxylic acid (3-fluoro-phenyl)-methyl amide | 230-232 | 1005.1 |
| 20 | HOCH₂CH₂-N(tetrazole) | 2-Tetrazole-2-yl-ethanol | 220-222 | 884.1 |

Example-21

Compound of Formula I-c, T is CO(CH₂)₂-(pyridin-3-yl), R₁ is CH₃

To the solution of 3-pyridin-3-yl-propionic acid (1.42 g, 7.5 mmol) in dichloromethane (40 ml) was added dicyclohexyl carbodiimide (1.55 g, 7.5 mmol) and stirred for 0.5 h at room temperature. To this reaction mixture Example 5 (2 g, 1.9 mmol) followed by dimethyl amino pyridine (0.131 g, 1.0 mmol) was added and stirred further for 2 h. The solid precipitated out was filtered and washed with dichloromethane (10 ml). The combined filtrate was evaporated under reduced pressure to furnish a thick liquid, which was used as it is without purification for further reaction.

To the solution of thick liquid (1.8 g, 1.5 mmol) obtained as above in THF (10 ml) was added 70% hydrogen fluoride in pyridine (130 μl, 4.53 mmol) under inert atmosphere and stirred for 15 h. The residue obtained after evaporation of solvent under reduced pressure was dissolved in ethyl acetate (15 ml) and washed with water (2×10 ml). The organic layer was dried (Na$_2$SO$_4$) and evaporated under reduced pressure to provide a white solid as title compound (1.3 g, 82%). MS 963 (M+H)$^+$.

Using the above procedure following examples were synthesized by using the corresponding carboxylic acid.

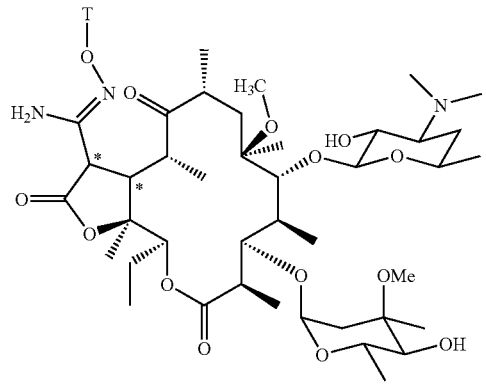

| Example | T | Reactant (A) | MP (° C.) | Mass (M + 1) |
|---|---|---|---|---|
| 22 | COCH$_2$O-(2-chlorophenyl) | (2-Chloro-phenoxy)-acetic acid | 150-152 | 998 |
| 23 | CO(CH$_2$)$_2$-(4-dimethylamino)phenyl | 3-(4-dimethylamino-phenyl)-propionic acid | 168-170 | 996 |
| 24 | CO(CH$_2$)$_2$-(3-fluoro)phenyl | 3-(3-fluorophenyl)-propionic acid | 170-172 | 980 |
| 25 | CO(CH$_2$)$_2$-(4-(4-methyl-piperazine)phenyl) | 3-[4-(4-methyl-piperazin-1-yl)-phenyl]-propionic acid | 168-170 | 1060 |
| 26 | CO(CH$_2$)$_2$-(4-(4-acetyl-[1,2,3]triazol-1-yl))-phenyl | 3-[4-(4-acetyl-[1,2,3]triazol-1-yl)-phenyl]-propionic acid | 174-176 | 1071 |
| 27 | CO(CH$_2$)$_2$-(4-phenyl-piperazinyl) | 3-(4-phenyl-piperazin-1-yl)-propionic acid | 165-167 | 1045 |
| 28 | CO(CH$_2$)$_2$-(4-(2-methoxy-phenyl)-piperazine-1-yl) | 3-[4-(2-methoxy-phenyl)-piperazin-1-yl]-propionic acid | 155-156 | 1076 |
| 29 | COCH$_2$—S-(3-methoxy phenyl) | (3-methoxy-phenylsulfanyl)-acetic acid | 158-160 | 1010 |
| 30 | CO(CH$_2$)$_2$CONH-(3-methoxy-phenyl) | N-(3-methoxy-phenyl)-succinamic acid | 170-172 | 1035 |
| 31 | CO(CH$_2$)$_2$CONH-(2,4-difluorophenyl) | N-(2,4-difluoro-phenyl)-succinamic acid | 190-192 | 1040 |
| 32 | CO(CH$_2$)$_2$CO-(4-phenyl-piperazin-1-yl | 4-oxo-4-(4-phenyl-piperazin-1-yl)-butyric acid | 162-163 | 1075 |
| 33 | COCH═CH-(pyridin-4-yl) | 3-pyridin-4-yl-acrylic acid | 210-212 | 961.1 |
| 34 | COCH═CH-(pyridin-3-yl) | 3-pyridin-3-yl-acrylic acid | 157-159 | 961.1 |
| 35 | COCH═CH-(pyridin-2-yl) | 3-pyridin-2-yl-acrylic acid | 107-110 | 961.1 |
| 36 | COCH═CH-(1-(2-methoxy-phenyl)-1H-[1,2,3]triazol-4-yl) | 3-[1-(2-methoxy-phenyl)-1H-[1,2,3]triazol-4-yl]-acrylic acid | 172-175 | 1057.2 |
| 37 | COCH═CH-(1-(3-methoxy-phenyl)-1H-[1,2,3]triazol-4-yl) | 3-[1-(3-methoxy-phenyl)-1H-[1,2,3]triazol-4-yl]-acrylic acid | 148-151 | 1057.2 |
| 38 | COCH═CH-(1-(4-fluoro-phenyl)-1H-[1,2,3]triazol-4-yl) | 3-[1-(4-fluoro-phenyl)-1H-[1,2,3]triazol-4-yl]-acrylic acid | 198-200 | 1045.1 |
| 39 | COCH═CH-(1-(3-fluoro-phenyl)-1H-[1,2,3]triazol-4-yl) | 3-[1-(3-fluoro-phenyl)-1H-[1,2,3]triazol-4-yl]-acrylic acid | 188-190 | 1045.1 |
| 40 | COCH═CH-(1-(4-methoxy-phenyl)-1H-[1,2,3]triazol-4-yl) | (E)-3-[1-(4-methoxy-phenyl)-1H-[1,2,3]triazol-4-yl]-acrylic acid | 203-202 | 1057.2 |
| 41 | CO(CH$_2$)$_2$-phenyl | 3-phenyl-propionic acid | 140-142 | 962.1 |
| 42 | CO(CH$_2$)$_2$-(pyridin-2-yl) | 3-pyridin-2-yl-propionic acid | 116-118 | 963.1 |
| 43 | CO(CH$_2$)$_2$-(1-(4-methoxyphenyl)-1H-[1,2,3]triazol-4-yl) | 3-[1-(4-methoxy-phenyl)-1H-[1,2,3]triazol-4-yl]-propionic acid | 182-184 | 1059.2 |
| 44 | CO(CH$_2$)$_2$-(1-(4-fluoro phenyl)-1H-[1,2,3]triazol-4-yl) | 3-[1-(4-fluoro-phenyl)-1H-[1,2,3]triazol-4-yl]-propionic acid | 202-205 | 1047.2 |
| 45 | CO(CH$_2$)$_2$-(pyridin-4-yl) | 3-pyridin-4-yl-propionic acid | 166-168 | 963.1 |

-continued

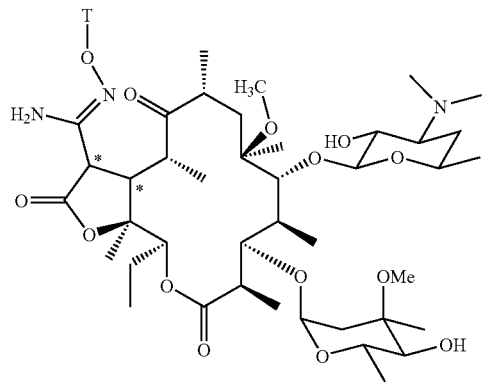

| Example | T | Reactant (A) | MP (° C.) | Mass (M + 1) |
|---|---|---|---|---|
| 46 | CO(CH$_2$)$_2$-(3-methoxy)phenyl | 3-(3-methoxy-phenyl)-propionic acid | 172-174 | 992.1 |
| 47 | CO(CH$_2$)$_2$-(4-methoxy)phenyl | 3-(4-methoxy-phenyl)-propionic acid | 164-167 | 992.1 |
| 48 | CO(CH$_2$)$_2$-(1-methyl phenyl)-1H-[1,2,3]triazol-4-yl) | 3-(1-m-tolyl-1H-[1,2,3]triazol-4-yl)-propionic acid | 172-174 | 1043.2 |
| 49 | CO(CH$_2$)$_2$-(1-chlorophenyl)-1H-[1,2,3]triazol-4-yl) | 3-[1-(3-chloro-phenyl)-1H [1,2,3]triazol-4-yl]-propionic acid | 176-178 | 1063.6 |
| 50 | CO(CH$_2$)$_2$-(3-(4-fluoro-phenyl)-[1,2,4]oxadiazol-5-yl) | 3-[3-(4-fluoro-phenyl)-[1,2,4]oxadiazol-5-yl]-propionic acid | 148-154 | 1048.1 |
| 51 | CO(CH$_2$)$_2$-(3-(3-bromo-phenyl)-[1,2,4]oxadiazol-5-yl) | 3-[3-(3-bromo-phenyl)-[1,2,4]oxadiazol-5-yl]-propionic acid | 158-160 | 1109.1 |
| 52 | CO(CH$_2$)$_2$-(3-(4-nitro-phenyl)-[1,2,4]oxadiazol-5-yl) | 3-[3-(4-nitro-phenyl)-[1,2,4]oxadiazol-5-yl]-propionic acid | 198-201 | 1075.2 |
| 53 | CO(CH$_2$)$_2$-(4-(pyridin-2-yl)-piperazinyl) | 3-(4-pyridin-2-yl-piperazin-1-yl)-propionic acid | 138-140 | 1047.281 |
| 54 | CO(CH$_2$)$_2$-(3-cyano)phenyl | 3-(3-Cyano-phenyl)-propionic acid | 170-172 | 987.1 |
| 55 | COCH$_2$O-(3-chloro)phenyl | 3-(3-Chloro-phenyl)-propionic acid | 158-161 | 996.6 |
| 56 | CO(CH$_2$)$_2$-(3,5-dimethoxy)phenyl | 3-(3,5-Dimethoxy-phenyl)-propionic acid | 118-120 | 1022.2 |
| 57 | CO(CH$_2$)$_2$-(2,3-dimethoxy)phenyl | 3-(2,3-Dimethoxy-phenyl)-propionic acid | 152-154 | 1022.2 |
| 58 | CO(CH$_2$)$_2$-(3-(3-fluoro-phenyl)-[1,2,4]oxadiazol-5-yl) | 3-[3-(3-Fluoro-phenyl)-[1,2,4]oxadiazol-5-yl]-propionic acid | 166-170 | 1048.1 |
| 59 | CO(CH$_2$)$_2$-(3-(3-chloro-phenyl)-[1,2,4]oxadiazol-5-yl) | 3-[3-(3-Chloro-phenyl)-[1,2,4]oxadiazol-5-yl]-propionic acid | 158-160 | 1064.6 |
| 60 | CO(CH$_2$)$_2$-(3-(3-methoxy-phenyl)-[1,2,4]oxadiazol-5-yl) | 3-[3-(3-Methoxy-phenyl)-[1,2,4]oxadiazol-5-yl]-propionic acid | 148-150 | 1060.2 |
| 61 | CO(CH$_2$)$_2$-(3-(3,5-dimethoxy-phenyl)-[1,2,4]oxadiazol-5-yl) | 3-[3-(3,5-Dimethoxy-phenyl)-[1,2,4]oxadiazol-5-yl]-propionic acid | 160-163 | 1090.2 |
| 62 | CO(CH$_2$)$_2$-(3-(4-chloro-phenyl)-[1,2,4]oxadiazol-5-yl) | 3-[3-(4-Chloro-phenyl)-[1,2,4]oxadiazol-5-yl]-propionic acid | 144-146 | 1064.6 |

-continued

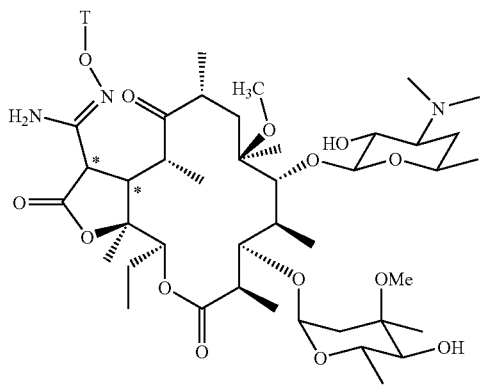

| Example | T | Reactant (A) | MP (° C.) | Mass (M + 1) |
|---|---|---|---|---|
| 63 | CO(CH$_2$)$_2$-(3-(4-bromo-phenyl)-[1,2,4]oxadiazol-5-yl) | 3-[3-(4-Bromo-phenyl)-[1,2,4]oxadiazol-5-yl]-propionic acid | 152-154 | 1109.1 |
| 64 | CO(CH$_2$)$_2$-(3-(pyridin-4-yl)-[1,2,4]oxadiazol-5-yl) | 3-(3-Pyridin-4-yl-[1,2,4]oxadiazol-5-yl)-propionic acid | 156 | 1031.1 |
| 65 | CO(CH$_2$)$_2$-(4-(2-methylphenyl)-piperazinyl) | 3-(4-o-tolyl-piperazin-1-yl)-propionic acid | 170 | 1060.3 |
| 67 | CO(CH$_2$)$_2$-(4-(3-methoxyphenyl)-piperazinyl | 3-[4-(3-Methoxy-phenyl)-piperazin-1-yl]-propionic acid | 146 | 1076.3 |
| 68 | CO(CH$_2$)$_2$-(4-(2-fluorophenyl)-piperazinyl) | 3-[4-(2-Fluoro-phenyl)-piperazin-1-yl]-propionic acid | 152 | 1064.2 |
| 69 | CO(CH$_2$)$_2$-(4-(pyrimidin-2-yl)-piperazinyl) | 3-(4-pyrimidin-2-yl-piperazin-1-yl)-propionic acid | 170 | 1048.2 |
| 70 | CO(CH$_2$)$_2$-(1-(2-fluorophenyl)-1H-[1,2,3]triazol-4-yl) | 3-[1-(2-fluoro-phenyl)-1H-[1,2,3]triazol-4-yl]-propionic acid | 162 | 1047.2 |
| 71 | CO(CH$_2$)$_2$-(4-trifluoromethyl)phenyl | 3-(4-trifluoromethyl-phenyl)-propionic acid | 168 | 1030.1 |
| 72 | CO(CH$_2$)$_2$-(3-(2-fluoro-5-methoxy-phenyl)-[1,2,4]oxadiazol-5-yl) | 3-[3-(2-fluoro-5-methoxy-phenyl)-[1,2,4]oxadiazol-5-yl]-propionic acid | 158 | 1078.2 |
| 73 | CO(CH$_2$)$_2$-(3-phenyl-4H-imidazol-1-yl) | 3-(4-phenyl-4H-imidazol-1-yl)-propionic acid | 172-174 | 1028.2 |
| 74 | COCH$_2$NHCONH-phenyl | (3-phenyl-ureido)-acetic acid | 164-168 | 1006.1 |
| 75 | CO(CH$_2$)$_2$-(4-([1,2,3]triazol-1-yl)phenyl) | 3-(4-[1,2,3]triazol-1-yl-phenyl)-propionic acid | 180-183 | 1029.2 |
| 76 | CO(CH$_2$)$_2$-(4-cyano)phenyl | 3-(4-Cyano-phenyl)-propionic acid | 168-170 | 987.1 |
| 77 | CO(CH$_2$)$_2$-(2,5-dimethoxy)phenyl | 3-(2,5-dimethoxy-phenyl)-propionic acid | 166-169 | 1022.2 |
| 78 | CO(CH$_2$)$_2$-(benzo[1,3]dioxol-5-yl) | 3-benzo[1,3]dioxol-5-yl-propionic acid | 138-140 | 1006.1 |
| 79 | CO(CH$_2$)$_2$-(3,5-dimethoxy)phenyl | 3-(3,5-dimethoxy-phenyl)-propionic acid | 170-174 | 1022.1 |
| 80 | CO(CH$_2$)$_2$-(1-(2,4-difluorophenyl)-1H-[1,2,3]triazol-4-yl) | 3-[1-(2,4-difluoro-phenyl)-1H-[1,2,3]triazol-4-yl]-propionic acid | 158-161 | 1065.2 |
| 81 | CO(CH$_2$)$_2$-(1-(3,4-difluorophenyl)-1H-[1,2,3]triazol-4-yl) | 3-[1-(3,4-difluoro-phenyl)-1H-[1,2,3]triazol-4-yl]-propionic acid | 172-175 | 1065.2 |

-continued

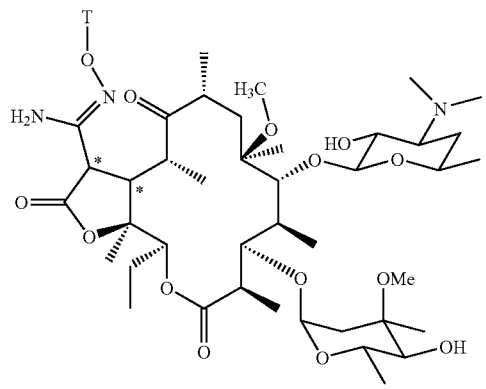

| Example | T | Reactant (A) | MP (° C.) | Mass (M + 1) |
|---|---|---|---|---|
| 82 | CO(CH$_2$)$_2$-(1-(2,3,4-trifluorophenyl)-1H-[1,2,3]triazol-4-yl) | 3-[1-(2,3,4-trifluoro-phenyl)-1H-[1,2,3]triazol-4-yl]-propionic acid | 108-110 | 1083.1 |
| 83 | CO(CH$_2$)$_2$-(1-(2-fluoro-4-methyl-phenyl)-1H-[1,2,3]triazol-4-yl) | 3-[1-(2-fluoro-4-methyl-phenyl)-1H-[1,2,3]triazol-4-yl]-propionic acid | 138-141 | 1061.2 |
| 84 | CO(CH$_2$)$_2$-(1-(2-fluoro-4-methoxy-phenyl)-1H-[1,2,3]triazol-4-yl) | 3-[1-(2-fluoro-4-methoxy-phenyl)-1H-[1,2,3]triazol-4-yl]-propionic acid | 168.000 | 1077.2 |
| 85 | CO(CH$_2$)$_2$-(1-(2,3-difluoro-4-ethoxy-phenyl)-1H-[1,2,3]triazol-4-yl) | 3-[1-(4-Ethoxy-2,3-difluoro-phenyl)-1H-[1,2,3]triazol-4-yl]-propionic acid | 136-139 | 1109.2 |
| 86 | CO(CH$_2$)$_2$-(4-(4-cyano-[1,2,4]triazol-1-yl)phenyl) | 3-[4-(4-Cyano-[1,2,3]triazol-1-yl)-phenyl]propionic acid | 144-148 | 1054.2 |
| 87 | CO(CH$_2$)$_2$CONH-(3-methoxy-phenyl) | N-(3-Methoxy-phenyl)-succinamic acid | 170-173 | 1035.2 |
| 88 | CO(CH$_2$)$_2$-(4-(imidazol-1-yl)phenyl) | 3-(4-Imidazol-1-yl-phenyl)-propionic acid | 168-171 | 1028.2 |
| 89 | CO(CH$_2$)$_2$-(4-([1,2,4]triazol-1-yl)phenyl) | 3-(4-[1,2,4]triazol-1-yl-phenyl)-propionic acid | 185-187 | 1029.2 |
| 90 | CO(CH$_2$)$_2$CONH-(2-methoxy-phenyl) | N-(2-Methoxy-phenyl)-succinamic acid | 186-188 | 1035.2 |
| 91 | CO(CH$_2$)$_2$CONH-(2,4-difluorophenyl) | N-(2,4-Difluoro-phenyl)-succinamic acid | 190-192 | 1041.1 |
| 92 | CO(CH$_2$)$_2$CO-(4-(4-fluoro-phenyl)piperazin-1-yl) | 4-[4-(2-Fluoro-phenyl)-piperazin-1-yl]-4-oxo-butyric acid | 160-164 | 1092.2 |
| 93 | COCH$_2$NHCONH-phenyl | (3-Phenyl-ureido)-acetic acid | 164-168 | 1006.1 |
| 94 | COCH$_2$-(benzo[1,3]dioxol-5-yl) | benzo[1,3]dioxol-5-yl-acetic acid | 170-174 | 992.1 |
| 95 | COCH$_2$NHCONH-(4-fluorophenyl) | [3-(4-fluoro-phenyl)-ureido]-acetic acid | 172-175 | 1024.1 |
| 96 | COCH$_2$NHCONH-(3-chloro-4-methylphenyl) | [3-(3-chloro-4-methyl-phenyl)-ureido]-acetic acid | 176-178 | 1054.6 |
| 97 | COCH$_2$O-phenyl | phenoxy-acetic acid | 160-164 | 964.1 |
| 98 | COCH$_2$S-phenyl | phenylsulfanyl-acetic acid | 158-160 | 980.2 |

Example-99

Compound of Formula I-c where T is CO(CH$_2$)$_2$-(1-(3,5-difluoro-phenyl)-1H-[1,2,3]triazol-4-yl), R$_1$ is CH$_3$ To a solution of 3-[1-(3,5-difluoro-phenyl)-1H-[1,2,3]triazol-4-yl]-propionic acid (0.288 g, 1.13 mmol) in dichloromethane (50 ml) was added dicyclohexylcarbodiimide (0.486 g, 2.35 mmol) and 1-hydroxy-benzotriazole (0.040 g, 0.296 mmol) at an ambient temperature. The reaction mixture was stirred further for 1 h. To this reaction mixture then added Example 5 (1.0 g, 0.946 mmol) and followed by dimethyl amino pyridine (0.033 g, 0.270 mmol) at an ambient temperature. The reaction mixture was further stirred for 1 h. The reaction mixture was filtered and the filtered solid was washed with dichloromethane (10 ml). The combined filtrate was evaporated under reduced pressure to provide a thick liquid (1.1 g), which was used as it is without purification for further reaction.

To a solution of above thick liquid (1.1 g, 0.876 mmol) in THF (20 ml) was added 70% hydrogen fluoride in pyridine (72 μl, 2.52 mmol) at room temperature under inert atmosphere. The resulting solution was further for 15 h. The solvent evaporated under reduced pressure. The residue was dissolved into water (30 ml) and washed with diethyl ether (3×25 ml). The aqueous layer upon saturation with sodium chloride a white solid was precipitated out, it was filtered and dried. The white solid obtained was triturated with diethyl ether to give the title compound as a white solid (0.400 g).

Using the above procedure following examples were synthesized by using the corresponding carboxylic acid.

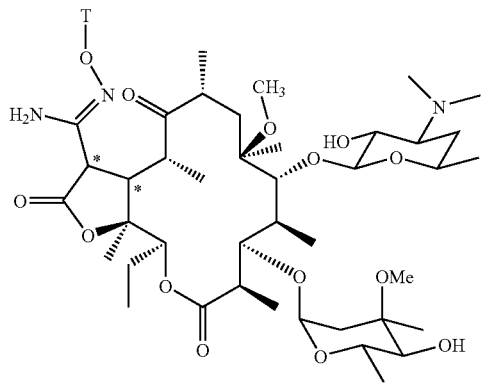

| Example | T | Carboxylic acid | MP (°C.) | Mass M + 1 |
|---|---|---|---|---|
| 100 | CO(CH$_2$)$_2$-(1-(2-methoxy)phenyl)-1H-[1,2,3]triazol-4-yl) | 3-[1-(2-Methoxy-phenyl)-1H-[1,2,3]triazol-4-yl]-propionic acid | 176-178 | 1059 |
| 101 | CO(CH$_2$)$_2$-(1-(3-fluoro-phenyl)-1H-[1,2,3]triazol-4-yl) | 3-[1-(3-fluoro-phenyl)-1H-[1,2,3]triazol-4-yl]propionic acid | 186-188 | 1047 |
| 102 | CO(CH$_2$)$_2$-(1-(3,4-difluoro-phenyl)-1H-[1,2,3]triazol-4-yl) | 3-[1-(3,4-difluoro-phenyl)-1H-[1,2,3]triazol-4-yl]-propionic acid | 168-170 | 868 |
| 103 | CO(CH$_2$)$_2$-(1-(3,5-dimethoxy-phenyl)-1H-[1,2,3]triazol-4-yl) | 3-[1-(3,5-dimethoxy-phenyl)-1H-[1,2,3]triazol-4-yl]-propionic acid | 180-182 | 1089 |
| 104 | CO(CH$_2$)$_2$-(1-(3-methoxy-phenyl)-1H-[1,2,3]triazol-4-yl) | 3-[1-(3-methoxy-phenyl)-1H-[1,2,3]triazol-4-yl]-propionic acid | 186-187 | 1032 |
| 105 | CO(CH$_2$)$_2$-(1-(pyridin-3-yl)-1H-[1,2,3]triazol-4-yl) | 3-(1-pyridin-3-yl-1H-[1,2,3]triazol-4-yl)-propionic acid | 170-172 | 1030 |

Example-106

Compound of Formula I-c where T is CO(CH$_2$)$_2$-(3-(2-fluoro-5-methoxy-phenyl)-[1,2,4]oxadiazol-5-yl), R$_1$ is CH$_3$ To a solution of 3-[3-(2-fluoro-5-methoxy-phenyl)-[1,2,4]oxadiazol-5-yl]-propionic acid (0.413 g, 1.89 mmol) in dichloromethane (50 ml) was added dicyclohexylcarbodiimide (0.486 g, 2.35 mmol) and 1-hydroxy-benzotriazole (0.040 g, 0.296 mmol) at an ambient temperature. The reaction mixture was stirred further for 1 h. To this reaction mixture then added Example 5 (1.0 g, 0.946 mmol) and followed by dimethyl amino pyridine (0.033 g, 0.270 mmol) at an ambient temperature. The reaction mixture was further stirred for 1 h. The reaction mixture was filtered and the filtered solid was washed with dichloromethane (10 ml). The combined filtrate was evaporated under reduced pressure to provide a thick liquid (1.1 g), which was used as it is without purification for further reaction.

To a solution of above thick liquid (1.1 g, 0.876 mmol) in THF (20 ml) was added 70% hydrogen fluoride in pyridine (65 μl, 2.27 mmol) at room temperature under inert atmosphere. The resulting solution was further for 15 h. The solvent evaporated under reduced pressure. The residue was dissolved into water (30 ml) and washed with diethyl ether (3×25 ml). The aqueous layer upon saturation with sodium chloride a white solid was precipitated out, it was filtered and dried. The white solid obtained was triturated with diethyl ether to give the title compound as a white solid (0.325 g).

Using the above procedure following examples were synthesized by using the corresponding carboxylic acid.

romethane (30 ml×3). Combined organic layer was dried over sodium sulphate and evaporated under vacuum to obtain crude white solid. It was then purified by column chromatography using $CHCl_3$:MeOH; 80:20) as a mobile phase to obtain title compound as white solid (Yield: 190 mg, 44%), MS 854 (M+H)$^+$ Mp: 213-214° C.

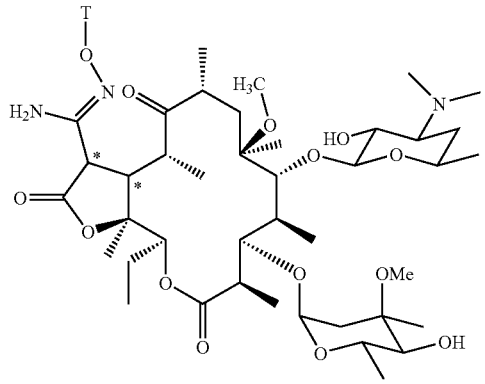

| Example | T | Carboxylic acid | MP (° C.) | Mass M + 1 |
|---|---|---|---|---|
| 107 | CO(CH$_2$)$_2$-(3-phenyl-[1,2,4]oxadiazol-5-yl) | 3-(3-Phenyl-[1,2,4]oxadiazol-5-yl)-propionic acid | 162-166 | 1030 |
| 108 | CO(CH$_2$)$_2$-(3-naphthalen-2-yl-[1,2,4]oxadiazol-5-yl) | 3-(3-Naphthalen-2-yl-[1,2,4]oxadiazol-5-yl)-propionic acid | 138-142 | 1080 |
| 109 | CO(CH$_2$)$_2$-(3-(pyridin-3-yl)-[1,2,4]oxadiazol-5-yl) | 3-(3-Pyridin-3-yl-[1,2,4]oxadiazol-5-yl)-propionic acid | 149-150 | 1031 |
| 110 | CO(CH$_2$)$_2$-[3-(4-methoxyphenyl)-[1,2,4]oxadiazol-5-yl] | 3-[3-(4-Methoxy-phenyl)-[1,2,4]oxadiazol-5-yl]-propionic acid | 132-134 | 1060 |

Example-111

Compound of Formula I-c where T is CH$_2$-(5-methyl-[1,2,4]oxadiazol-3-yl), R$_1$ is CH$_3$ Step A: To a stirred solution of Example 5 (1.0 g, 0.95 mmol) in 1,4-dioxan (10 ml) was added N,N-dimethylformamide dimethylacetal (2 ml) and heated at 70° C. for 2 h. After completion of reaction solvent was evaporated under vacuum, water was added to the crude reaction mass and extracted with ethyl acetate (50 ml×3). Combined organic layer was dried over anhydrous sodium sulphate and then evaporated yielding crude solid. It was then purified by column chromatography using (Ethyl acetate:n-hexane; 20:80) as a mobile phase. Pale solid compound was isolated Yield: 550 mg, (55%).

Step B: The compound obtained in Step A (550 mg, 0.50 mmol) was dissolved in acetonitrile (10 ml). 70% HF-Pyridine solution (44 µl, 3.0 equi.) was added to the above solution and stirred at room temperature for overnight under N$_2$ atmosphere. After completion of reaction solvent was evaporated under vacuum to obtain crude solid. Water (20 ml) was added to the crude product and then extracted with dichlo- Example-112

Compound of Formula I-c where T is CH$_2$CONH-(3-chloro)phenyl, R$_1$ is CH$_3$

Step-1: To the stirred solution of Example 5 (1.00 g, 0.94 mmol) in benzene (20 ml) was added sodium hydride (47 mg, 1.13 mmol, 60% suspension in mineral oil) at 25-30° C. temperature and stirred for 30 min. 2-Bromo-N-(3-chlorophenyl)-acetamide (0.25 g, 1.04 mmol) was added to reaction mixture and stirred for 1 hour at an 25-30° C. temperature. The reaction mixture was then poured in aqueous saturated ammonium chloride solution (30 ml). Organic layer was dried over Na$_2$SO$_4$. It was purified using silica gel column chromatography (10% Acetone:Hexane) to provide step-1 product as solid in 75% (0.87 g) yield. MS: m/z: 1229 (M+1)

Step-2: A mixture of step-1 product and (0.80 g, 0.65 mmol) 70% HF in pyridine (55 µl, 1.95 mmol) in THF (15 ml) was stirred under inert atmosphere for 15 h at 25-30° C. temperature. The solvent was evaporated under vacuum to provide a residue. The residue was dissolved in ethyl acetate (15 ml) and washed with water (2×10 ml). The organic layer was dried over Na$_2$SO$_4$ and evaporated under vacuum to provide crude solid which on trituration in diethyl ether afforded pale yellow solid as the title compound Example in 65% (0.42 g) yield. Mp: 128-131° C., Mass: M/z: 997.1 (M+1).

Following examples were prepared by using above procedure and by using reactant A.

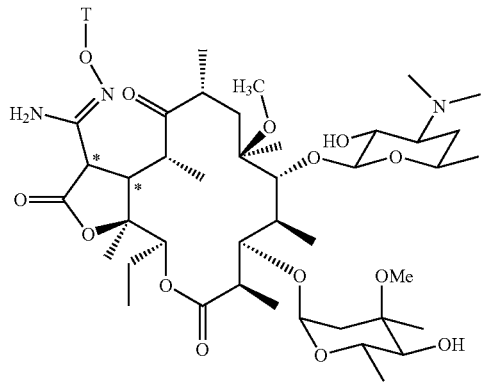

| Example | T | Reactant (A) | MP (° C.) | Mass (M + 1) |
|---|---|---|---|---|
| 113 | CH$_2$CONH$_2$ | 2-bromo-acetamide | 207-210 | 887.1 |
| 114 | CH$_2$CONH-(2-methoxy)phenyl | 2-Bromo-N-(2-methoxy-phenyl)-acetamide | 188-190 | 993.1 |
| 115 | CH$_2$CONH-(3-methoxy)phenyl | 2-Bromo-N-(3-methoxy-phenyl)-acetamide | 190-194 | 993.1 |
| 116 | CH$_2$CONH-(2-fluoro)phenyl | 2-Bromo-N-(2-fluoro-phenyl)-acetamide | 184-187 | 981.1 |
| 117 | CH$_2$CONH-(3-fluoro)phenyl | 2-Bromo-N-(3-fluoro-phenyl)-acetamide | 182-185 | 981.1 |
| 118 | CH$_2$CONH-(4-fluoro)phenyl | 2-Bromo-N-(4-fluoro-phenyl)-acetamide | 190-194 | 981.1 |
| 119 | CH$_2$CONH-(2,4-difluoro)phenyl | 2-Bromo-N-(2,4-difluoro-phenyl)-acetamide | 178-182 | 999.1 |
| 120 | CH$_2$CONH-(3,4-difluoro)phenyl | 2-Bromo-N-(3,4-difluoro-phenyl)-acetamide | 196-199 | 999.1 |
| 121 | CH$_2$CONH-(2,3,4-trifluoro)phenyl | 2-Bromo-N-(2,3,4-trifluoro-phenyl)-acetamide | 190-194 | 1017.1 |
| 122 | CH$_2$CONH-(3,5-dimethoxy)phenyl | 2-Bromo-N-(3,5-dimethoxy-phenyl)-acetamide | 184-187 | 1023.1 |
| 123 | CH$_2$CONH-cyclopropyl | 2-Bromo-N-cyclopropyl-acetamide | 180-183 | 927.1 |
| 124 | CH$_2$CON(CH$_3$)-(3-fluoro)phenyl | 2-Bromo-N-(3-fluoro-phenyl)-N-methyl-acetamide | 174-178 | 995.1 |
| 125 | CH$_2$CON(CH$_3$)-(4-chloro)phenyl | 2-Bromo-N-(4-chloro-phenyl)-N-methyl-acetamide | 198-201 | 1011.1 |
| 126 | CH$_2$CONH-(3-(pyrazol-1-yl)-pyridin-5-yl) | 2-Bromo-N-(6-pyrazol-1-yl-pyridin-3-yl)-acetamide | 172-175 | 1030.1 |
| 127 | CH$_2$-(1-(4-fluorophenyl)-1H-[1,2,3]-triazol-5-yl) | 4-Bromomethyl-1-(4-fluoro-phenyl)-1H-[1,2,3]-triazole | 158-160 | 1008.1 |
| 128 | CH$_2$-(1-(3-fluorophenyl)-1H-[1,2,3]-triazol-5-yl) | 4-bormomethyl-1-(3-fluorophenyl)-1H-[1,2,3]-triazole | 210-212 | 1008.1 |
| 129 | CH$_2$-(1-(3,5-difluoro phenyl)-1H-[1,2,3]-triazol-5-yl) | 4-bromomethyl-1-(3,5-difluoro-phenyl)-1H-[1,2,3]-trizole | 191-193 | 1026.1 |
| 130 | CH$_2$-(1-(3,4-difluoro phenyl)-1H-[1,2,3]-triazol-5-yl) | 4-bromomethyl-1-(3,4-difluoro-phenyl)-1H-[1,2,3]-triazole | 190-192 | 1026.1 |
| 131 | CH$_2$-(1-(3,4,5-trifluorophenyl)-1H-[1,2,3]-triazol-5-yl) | 4-bromomethyl-1-(2,3,4-trifluoro-phenyl)-1H-[1,2,3]-triazole | 180-182 | 1044.1 |
| 132 | CH$_2$-(1-(3-chlorophenyl)-1H-[1,2,3]-triazol-5-yl) | 4-bromomethyl-1-(3-chloro-phenyl)-1H-[1,2,3]-triazole | 191-193 | 1023.1 |
| 133 | CH$_2$-(5-(pyridin-2-yl)-[1,2,4]-oxadiazol-3-yl) | 2-(3-bromomethyl-[1,2,4]-oxadiazole-5-yl)-pyridine | 149-151 | 990.1 |

Example-134

Compound of Formula I-c where T is CH₂-phenyl, R₁ is CH₃

To the stirring solution of Example 5 (0.56 mmol) in benzene (10 ml) was added NaH (0.62 mmol) and stirred it for 30 min. To this stirring solution, benzyl bromide (0.68 mmol) was added and stirred the reaction mixture for 4 hours at 60° C. The reaction mixture was allowed to come at room temperature and then poured in water (20 ml). Separated organic layer and dried over Na₂SO₄. Purified it with silica gel column chromatography (20% Ethyl acetate:Hexane). Yield 54%. The above product (0.31 mmole) was taken in tetrahydrofuran (5 ml) and added HF-Pyridine complex (1.24 mmole). Stirred at room temperature for overnight. The reaction mixture was concentrated and water was added. Extracted the product in dichloromethane (2×10 ml). Dried it (Na₂SO₄) and concentrated to give title compound in yield 44%. MS 920 (M+H).

Using the above procedure following examples were synthesized by using the corresponding Reagent A.

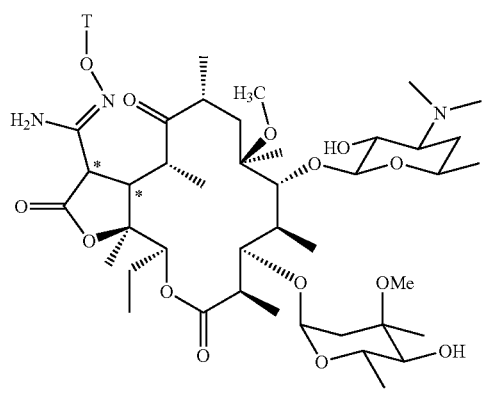

| Example | T | Reagent A | M.P. (° C.) | Mass M + 1 |
|---|---|---|---|---|
| 135 | CH₂C(CH₃)=CH₂ | 3-bromo-2-methyl-propene | 184-186 | 884 |
| 136 | CH₂-(4-nitro)phenyl | 4-nitrobenzyl bromide | 160-164 | 965 |
| 137 | CH₂CH₂-(4-(pyridin-2-yl)piperazinyl) | 1-(2-bromoethyl)-4-pyridin-2-yl-piperazine | 130-132 | 1019 |
| 138 | CH₂CH=CH-(2,3-dihydro-benzo[1,4]dioxin-6-yl) | 6-bromo-1,4-benzo dioxane | 176-178 | 1004 |
| 139 | CH₂CH=C(CH₃)₂ | 1-bromo-3-methyl-but-2-ene | 195-197 | 899.1 |
| 140 | CH₂CH₂CH=CH₂ | 4-bromo-but-1-ene | 194-196 | 885.1 |
| 141 | CH₂-(4-methyl-phenyl) | 4-methyl-benzyl bromide | 178-180 | 935.1 |
| 142 | CH₂-(2-methyl henyl) | 2-methyl benzyl bromide | 160-162 | 935.1 |
| 143 | CH₂-(3-methoxy phenyl) | 3-methoxy-benzyl bromide | 168-170 | 951.1 |
| 144 | CH₂-(2-fluorophenyl) | 2-fluoro-benzyl bromide | 172-174 | 939.1 |
| 145 | CH₂-(4-bromophenyl) | 4-bromo-benzyl bromide | 168-170 | 1000.1 |
| 146 | CH₂-(2,4-difluorophenyl) | 2,4-difluoro-benzyl bromide | 166-168 | 957.1 |
| 147 | CH₂-(2,5-difluorophenyl) | 2,5-difluoro-benzyl bromide | 166-168 | 957.1 |
| 148 | CH₂CO₂CH₂CH₃ | ethyl bromoacetate | 190-192 | 917.1 |

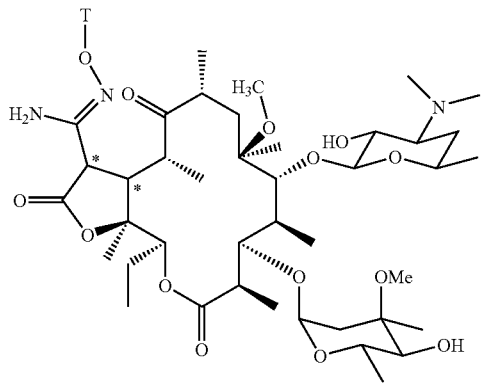

| Example | T | Reagent A | M.P. (° C.) | Mass M + 1 |
|---|---|---|---|---|
| 149 | CH₂CO-(4-phenyl-piperazin-1-yl) | 2-bromo-1-(4-phenyl-piperazin-1-yl)-ethanone | 179-181 | 1033.1 |
| 150 | CH₂CO-(4-(2-fluorophenyl)-piperazin-1-yl) | 2-bromo-1-[4-(2-fluoro-phenyl)-piperazin-1-yl]-ethanone | 194-196 | 1051.1 |

Example 151

Compound of Formula I-c where T is CH₂CN, R₁ is CH₃

Step A: To the stirring solution of the Example 5 (15.52 mmol) in acetone was added K₂CO₃ (1.2 eq), bromo acetonitrile (1.1 eq) and refluxed it for 48 hours. The reaction mixture was concentrated under vacuo. Water was added and filtered the residue. Dried it and purified it with column chromatography (EA; Hexane 20:80). Yield 77%.

Step B: To the stirring solution of the compound obtained in step B (0.52 mmol) in dry acetonitrile was added 70% HF in Pyridine complex (3.5 eq) The resulting mixture was stirred for 16 hours at room temperature under nitrogen atmosphere. The reaction mixture evaporated under vacuo. Water was added and extracted it in chloroform. Dried it over Na₂SO₄ and concentrated it. The residue was crystallized from ethanol:water (30:70) to give the title compound in yield 67%. MS 869 (M+H)⁺. Mp: 172-174° C.

Example 152

Compound of Formula I-c where T is CH₂C(NH₂)=N—OH, R₁ is CH₃

Step-1: To the solution of compound obtained in step A of above example (5.0 g, 4.55 mmol) in methanol (40 ml) was added hydroxylamine hydrochloride (3.25 g), and sodium bicarbonate (4.21 g, 50.1 mmol) stirred for 12 hr at room temperature. The reaction mass was concentrated under vacuum to obtain crude solid. The crude solid was stirred with water (100 ml). Solid separated was filtered under suction and dried under vacuum to provide step-1 product in 93% (4.8 g) yield. Mass: m/z: 1130 (M+1).

Step-2: A mixture of step-1 product (1.0 g, 0.9 mmol) and 70% hydrogen fluoride in pyridine (77 μl, 2.6 mmol) in THF (15 ml) was stirred under inert atmosphere at a temperature between 25-30° C. for 15 h. The solvent was evaporated under vacuum and the residue obtained was dissolved in ethyl acetate (25 ml) and washed with water (2×10 ml). The combined organic layer was dried over $Na_2SO_4$ and evaporated under reduced pressure to provide crude solid which on trituration in diethyl ether afforded pale yellow solid as the title compound in 60% (0.65 g) yield. Mp: 168-170° C. Mass: m/z: 903.1 (M+1).

Example-153

Compound of Formula I-c where T is $CH_2CH=CH_2$, $R_1$ is $CH_3$

Step A: To the stirring solution of Example 5 (0.56 mmol) in Toluene (10 ml) was added Potassium tert butoxide (0.62 mmol) and stirred it for 20 min. To this stirring solution, allyl bromide (0.68 mmol) was added and stirred the reaction mixture for 2 hours at room temperature. The reaction mixture was then poured in water (20 ml). Separated organic layer and dried over $Na_2SO_4$. Purified it with silica gel column chromatography (20% Ethyl acetate:Hexane). Yield 74%.

Step B: The product from step A (0.31 mmol) was taken in tetrahydrofuran (5 ml) and added HF-Pyridine complex (1.24 mmol). Stirred at room temperature for overnight. The reaction mixture was concentrated and water was added. Extracted the product in dichloromethane (2×10 ml). Dried it ($Na_2SO_4$) and concentrated to give title compound in yield 60%. MS 867 (M+H). M.P 194-196° C.

Example-154

Compound of Formula I-c where T is $CH_2CH=CH$-phenyl, $R_1$ is $CH_3$

Step-A: To the stirred solution of compound obtained in Step A of above example (1.5 g, 1.36 mmol) in DMF (15 ml) was added sodium acetate (0.24 ml, 2.73 mmol) at 25-30° C. temperature. To the above solution tetrakis triphenylphosphine palladium (0) (0.15 g, 0.13 mmol) and bromobenzene (0.31 g) were added and the reaction mixture was stirred at 120° C. temperature for 12 hours. The reaction mixture was quenched by pouring in aqueous saturated ammonium chloride solution (20 ml). The mixture was extracted with ethyl acetate (3×50 ml). Combined organic layer was dried over $Na_2SO_4$ to provide a residue. The residue was purified by using silica gel column chromatography (10% Acetone:Hexane) to provide step-1 product as a solid in 65% (1.0 g) yield. MS: m/z: 1226 (M+1).

Step-B: A mixture of step-2 product (0.90 g, 0.73 mmol) and 70% hydrogen fluoride in pyridine (63 μl, 2.20 mmol) in THF (15 ml) was stirred under inert atmosphere for 15 h. The solvent was evaporated under vacuum to provide a residue. The residue was dissolved in ethyl acetate (15 ml) and washed with water (2×10 ml). The organic layer was dried over $Na_2SO_4$ and evaporated under vacuum to provide crude solid which on trituration in diethyl ether afforded white solid as the title compound example in 55% (0.40 g) yield. Mass: m/z: 998.1 (M+1) Mp: 196-199° C.

Following examples were prepared by using above procedure and by using reactant A.

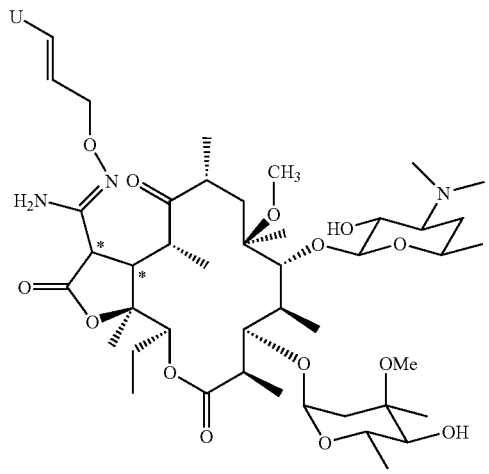

| Example | U | Reactant A | MP °C. | Mass M + 1 |
|---|---|---|---|---|
| 155 | (2-methoxy)phenyl | 1-bromo-2-methoxy-benzene | 120 | 976.2 |
| 156 | (3-fluoro)phenyl | 1-bromo-3-fluoro-benzene | 182 | 964.1 |
| 157 | (4-cyano)phenyl | 4-bromo-benzonitrile | 160 | 971.1 |
| 158 | (3-hydroxymethyl)phenyl | (3-bromophenyl)-methanol | 125 | 976.2 |
| 159 | (4-trifluoromethyl)phenyl | 1-bromo-4-trifluoromethyl-benzene | 96 | 1014.1 |
| 160 | (3-trifluoromethyl)phenyl | 1-bromo-3-trifluoro methyl-benzene | 176 | 1014.1 |
| 161 | (3-acetoxy)phenyl | 1-(4-bromophenyl)-ethanone | 155 | 988.2 |

Example-162

Compound of Formula I-c where T is CH₂-(3-(5-fluoro-2-methoxyphenyl)-isoxazol-5-yl), R₁ is CH₃

Step-1: To the stirred solution of compound obtained in Step A of example 153 (1.5 g, 1.36 mmol) in toluene (15 ml) was added triethylamine (0.38 ml, 2.73 mmol) followed by 2-methoxy-5-fluoro imidoyl chloride (0.34 g, 2.05 mmol) at 25-30° C. temperature. The reaction mixture was stirred at 90° C. temperature for 12 hours. It was diluted with ethyl acetate (50 ml) followed by addition of water (20 ml). Organic layer was dried over Na₂SO₄, evaporated under vacuum to provide a residue. The residue was purified by using silica gel column chromatography (10% Acetone:Hexane) to afford step-1 product as a solid in 70% (1.2 g) yield. MS 1264.1 (M+1).

Step-2: A mixture of step-1 product (1. g, 0.79 mmol) and 70% hydrogen fluoride in pyridine (68 μl, 2.37 mmol) in THF (15 ml) was stirred under inert atmosphere for 15 h. The solvent was evaporated under vacuum and the residue obtained was dissolved in ethyl acetate (25 ml) and washed with water (2×10 ml). The organic layer was dried over Na₂SO₄ and evaporated under vacuum to provide crude solid which upon trituration with diethyl ether afforded pale yellow solid as the title compound example in 60% (0.49 g) yield. Mass: M/z: 950.1 (M+1). Mp: 192-194° C.

Example-163

Compound of Formula I-c where T is CH₂C≡CH, R₁ is CH₃

Step A: To the stirring solution of Example 5 (0.56 mmol) in Toluene (10 ml) was added Potassium tert butoxide (0.62 mmol) and stirred it for 20 min. To this stirring solution, 3allyl bromide (0.68 mmol) was added and stirred the reaction mixture for 2 hours at room temperature. The reaction mixture was then poured in water (20 ml). Separated organic layer and dried over Na₂SO₄. Purified it with silica gel column chromatography (20% Ethyl acetate:Hexane). Yield 78%.

Step B: The product from step A (0.31 mmole) was taken in tetrahydrofuran (5 ml) and added HF-Pyridine complex (1.24 mmole). Stirred at room temperature for overnight. The reaction mixture was concentrated and water was added. Extracted the product in dichloromethane (2×10 ml). Dried it (Na₂SO₄) and concentrated to give title compound in yield 60%. MS 868 (M+H). M.P 168-170° C.

Example-164

Compound of Formula I-c where T is CH₂C≡C-(3-cyano-phenyl), R₁ is CH₃

Step-1: To the solution of compound obtained in step A of above example (1.4 g, 1.23 mmol) in DMF (40 ml) was added cesium carbonate (0.63 g, 3.2 mmol), bis-triphenylphosphine Palladium (II) chloride (0.10 g, 0.13 mmol), cuprous Iodide (0.05 g, 0.26 mmol) followed by 3-iodobenzonitrile (0.29 g, 1.27 mmol). The reaction mixture was stirred at 25-30° C. temperature under nitrogen atmosphere for 12 hrs. it was quenched with addition of ice-cold water (15 ml) to provide a suspension. Solid was filtered & dried under vacuum. The solid was purified by using silica gel column chromatography (20% ethyl acetate-Hexane) to provide step-1 product as a solid in 33% (0.5 g) yield. Mass: m/z: 1198 (M+1).

Step-2: A mixture of step-1 product (0.5 g, 0.41 mmol) and 70% hydrogen fluoride in pyridine (1.0 mmol) in THF (10 ml) was stirred under inert atmosphere at 25-30° C. temperature for 15 hr. The solvent was evaporated under vacuum, obtained residue was dissolved in ethyl acetate (15 ml) and washed with water (2×10 ml). The organic layer was dried over Na₂SO₄ and evaporated under vacuum to provide crude solid which on trituration in diethyl ether afforded off white solid as the title compound in 19% (0.075 g) yield. Mass: m/z: 970.1 (M+1). Mp: 158-159° C.

Following examples were prepared by using above procedure and by using reactant A.

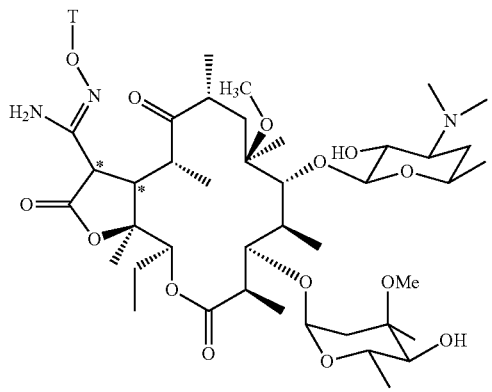

| Example | T | Reactant A | MP ° C. | Mass (M + 1) |
|---|---|---|---|---|
| 165 | CH₂C≡C-phenyl | Iodo-benzene | 150-151 | 945.1 |
| 166 | CH₂C≡C-(3-methyl)phenyl | 3-methyl-iodo-benzene | 194-195 | 959.1 |

Example-167

Compound of Formula I-c where T is CONH-phenyl, R₁ is CH₃

Step-1: To the stirred solution of Example-5 (0.75 g, 0.70 mmol) in dichloromethane (40 ml) was added phenylisocyanate (0.12 ml) at 25-30° C. temperature. The reaction mixture was stirred further for 2 h. The mixture was quenched by addition of water (20 ml) and extracted with dichloromethane (2×20 ml). Combined organic layer was dried over Na₂SO₄ and concentrated under vacuum to obtain crude solid. It was purified by using silica gel column chromatography (10% Acetone:n-Hexane) to furnish step-1 product as a pale yellow solid in 55% (0.48 g) yield. Mass: m/z: 1226 (M+1).

Step-2: A mixture of step-1 product (0.47 g, 0.38 mmol) and 70% hydrogen fluoride in pyridine (32 μl, 1.14 mmol) in THF (10 ml) was stirred under inert atmosphere for 15 h. The solvent was evaporated and the residue obtained was dissolved in ethyl acetate (15 ml) and washed with water (2×10 ml). The organic layer was dried over Na₂SO₄ and evaporated under vacuum to provide crude solid which on trituration in diethyl ether afforded title compound as a pale yellow solid in 60% (0.28 g) yield. Mp: 192-194° C., Mass: m/z: 950.1 (M+1).

Example-168

Compound of Formula I-c where T is
CONH-(4-ethyl-phenyl), $R_1$ is $CH_3$

Using above procedure and by using 4-ethyl-phenyl isocyanate in the place of phenyl isocyanate the title compound was prepared. Mp: 152-155° C., Mass: m/z: 978.1.

Example-169

Compound of Formula I-c where T is $CH_2CH_2CH_3$,
$R_1$ is $CH_3$

Step-A: A stirred suspension of product obtained from the Step A of Example 153 (1 g, 0.9 mmol) and 10% palladium on carbon (100 mg)) in tetrahydrofuran (10 ml) was stirred under atmospheric hydrogen pressure at 25-30° C. temperature for 12 hours. The reaction mixture was filtered over celite bed, and filtrate was evaporated under vacuum to provide step-1 product as a white solid in 90% (0.9 g) yield. It was used as such for the next reaction. Mass: m/z: 1101.1 (M+1).

Step-B: A mixture of step-1 product (0.9 g, 0.82 mmol) and 70% hydrogen fluoride in pyridine (24 µl, 2.5 mmol) in THF (10 ml) was stirred under inert atmosphere for 15 h. The solvent was evaporated and the residue obtained was dissolved in ethyl acetate (15 ml) and washed with water (2×10 ml). The organic layer was dried over $Na_2SO_4$ and evaporated under vacuum to provide crude solid which on trituration in diethyl ether afforded pale yellow solid title compound in 50% (70 g) yield. Mp: 182-184° C. Mass: m/z: 873.1 (M+1).

Following examples were prepared by using above procedure and by using the corresponding unsaturated compound

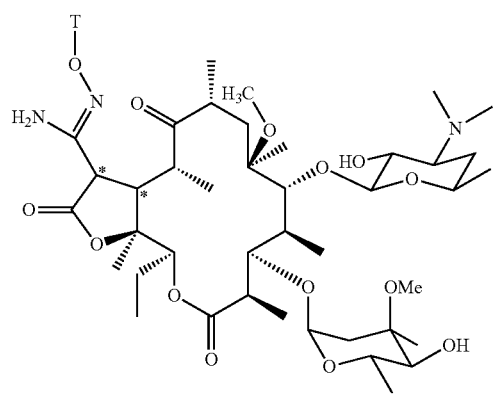

| Example | T | Starting material | Mp (° C.) | Mass (M + 1) |
|---|---|---|---|---|
| 170 | $CH_2CH(CH_3)_2$ | Example 135 | 210-212 | 887.1 |
| 171 | $CH_2CH_2CH(CH_3)_2$ | Example 139 | 184-186 | 901.1 |

Example-172

Compound of Formula I-e where Het is
[1,2,4]-oxadiazol-3-yl

Step A: To a stirred solution of Example 7 (1.0 g, 1.3 mmol) in (10 ml) 1,4-dioxan was added (2 ml) N,N dimethylformamide dimethylacetal and heated at 70° C. for 3 h. After completion of reaction solvent was evaporated under vacuum, water (30 ml) was added to the crude reaction mass and extracted with ethyl acetate (50 ml×3). Combined organic layer was dried over anhydrous sodium sulphate and then evaporated yielding crude solid. It was then purified by column chromatography using (Ethyl Acetate:n-hexane; 35:65) as a mobile phase. Pale solid was isolated. Yield: 450 mg, (45%).

Step B: To a stirred solution of the compound obtained in step A (450 mg, 0.6 mmol) in dichloromethane (10 ml) was added Dess Martin Periodinane reagent (2.0 ml, 1.2 equi., 15% solution) under $N_2$ atmosphere at room temperature for 30 min. After completion of reaction, additional 25 ml of dichloromethane was added and then quenched with 30 ml saturated aqueous solution of sodium thiosulphate:sodium bicarbonate. Organic layer was dried over anhydrous sodium sulphate and then distilled off under vacuum to obtain pale yellow solid. It was then purified by column chromatography using (Ethyl Acetate:n-Hexane; 30:70) as a mobile phase. Crystalline solid was isolated. Yield: 250 mg, (52%).

Step C: The compound obtained in step B (250 mg, 0.30 mmol) was dissolved in acetonitrile (10 ml). 70% HF-Pyridine solution (18 µl, 2.0 euqi.) was added to the above solution and stirred at room temperature for overnight under $N_2$ atmosphere. After completion of reaction solvent was evaporated under vacuum to obtain crude product. Water (20 ml) was added to the crude product and extracted with dichloromethane (25 ml×3). Combined organic layer was dried over sodium sulphate and evaporated under vacuum to obtain crude white solid. It was then purified by column chromatography using $CHCl_3$:MeOH (90:10) as a mobile phase to obtain title compound as white solid compound. Yield: 120 mg, (56%) MS: 681.1 (M+H)$^+$. Yield: 0.185 mg, (55%), M.P.: 208-210° C.

Example-173

Compound of Formula I-e where Het is
(5-trifluoromethyl)-[1,2,4]-oxadiazol-3yl

Step A: To a stirring solution of Example 9 (1.0 gm, 1.3 mmol) in dichloromethane (25 ml) was added trifluoroacetic anhydride (0.365 ml, 2.6 mmol) and triethyl amine (0.550 ml, 3.9 mmol). The resulting reaction mixture was heated at 45° C. for 12 h water (25 ml) was added to and extracted with dichloromethane (2×20 ml). Combined organic layer was dried over $Na_2SO_4$ and evaporated under reduced pressure. Resulting crude residue was purified by using column chromatography (15% Acetone-Hexane) to afford pale solid. Yield: 0.6 gm.

Step B: To a stirred solution of the compound obtained in step A (580 mg, 0.7 mmol) in dichloromethane (10 ml) was added Dess Martin Periodinane reagent (2.4 ml, 1.2 equi., 15% solution) under $N_2$ atmosphere at room temperature for 30 min. After completion of reaction, additional 25 ml of dichloromethane was added and then quenched with 30 ml saturated aqueous solution of sodium thiosulphate:sodium bicarbonate. Organic layer was dried over anhydrous sodium sulphate and then distilled off under vacuum to obtain pale yellow solid. It was then purified by column chromatography using (Ethyl Acetate:n-Hexane; 30:70) as a mobile phase. Crystalline solid was isolated. Yield: 300 mg, (52%).

Step C: The compound obtained in step B (280 mg, 0.35 mmol) was dissolved in acetonitrile (10 ml). 70% HF-Pyridine solution (19 µl, 2.0 euqi.) was added to the above solution and stirred at room temperature for overnight under $N_2$ atmosphere. After completion of reaction solvent was evaporated under vacuum to obtain crude product. Water (20 ml) was added to the crude product and extracted with dichloromethane (25 ml×3). Combined organic layer was dried over sodium sulphate and evaporated under vacuum to obtain crude white solid. It was then purified by column chromatography using $CHCl_3$:MeOH; 90:10) as a mobile phase to obtain title compound as white solid compound. Yield: 180 mg, (66%), Mass: 749.1 (M+H)$^+$ M.P. 200-202° C.

Example-174

Compound of Formula I-e where Het is (4,5)-dihydro-1H-imidazol-2-yl

Step A: To a mixture of Example 6 (1.0 g, 1.3 mmol) and ethylene diamine (3.0 ml) was added sulphur powder (21 mg, 0.66 mmol) and heated the resulting reaction mixture at 120° C. for 45 min. Reaction mixture was cooled to room temperature and ice cold water was added under stirring. Crude solid separated was filtered and dried. It was purified by using column chromatography (15% Acetone-n-Hexane) affording (0.8 gm) pale yellow solid.

Step B: The intermediate from step A (0.75 g, 0.94 mmol) was dissolved in dichloromethane (60 ml). To this reaction mixture a solution Dess-Martin periodinane (15% in DCM, 3.2 ml, 1.13 mmol) was added under an inert atmosphere. The reaction mixture was stirred at room temperature for 15 min. and a solution of $Na_2S_2O_3$ (10% in saturated aqueous solution of sodium bicarbonate, 60 ml) was added and stirred for 10 min. The organic layer was separated and the aqueous layer was extracted with dichloromethane (3×15 ml) and the combine organic layer was dried ($Na_2SO_4$). The removal of the solvent under reduced pressure provided the crude solid, which was purified by column chromatography over silica gel using n-hexane:EtOAc (8:2) as an eluent. The title compound was obtained a white solid (0.35 g). m\z ([MH]$^+$)=794.

Step C: To the solution of intermediate from step B (0.30 g, 0.37 mmol) in anhydrous THF (25 ml) was added 70% hydrogen fluoride in pyridine (16 μl, 0.56 mmol). The reaction mixture was stirred at an ambient temperature under inert atmosphere for 3 h. To the reaction mixture water (15 ml) was added and extracted with ethyl acetate (3×15 ml). The combined organic layer was dried ($Na_2SO_4$) and evaporated under reduced pressure. The thick liquid on trituration with n-pentane furnished the title compound as a white solid. Yield: 0.18 g (70%), Mass: 681.1 (M+H)$^+$, M.P.: 152-154° C.

Example 175

Compound of Formula I-e where Het is 1-(2-methoxyethoxy)-1H-tetrazol-5-yl

Example 176

Compound of Formula I-e where Het is 2-(2-methoxyethoxy)-2H-tetrazol-5-yl

Step-1: To the stirring solution of the product obtained in Step B, of above Example 12 (2 gm, 1.73 mmol) in acetonitrile (10 ml), 2N HCl (10 ml) was added and stirred reaction mixture at room temperature for 4-5 hours. Reaction mixture was neutralized with saturated sodium bicarbonate (20 ml) solution and then extracted in chloroform (2×20 ml). The combined organic layer was washed with water, dried over $Na_2SO_4$, and then concentrated it under reduced pressure to get the intermediate II. Yield 1.4 gm.

Step-2: To the stirring solution of compound-II (1.4 gm, 1.82 mmol) in acetone (20 ml) acetic anhydride (0.56 ml, 5.6 mmol) and $K_2CO_3$ (0.400 gm, 2.9 mmol) was added. The reaction mixture was stirred for 24 hours at room temperature. The solvent was removed under vacuo and water was added. It was extracted in chloroform (2×25 ml). The combined organic layer was washed with water and dried over $Na_2SO_4$ and evaporated under reduced pressure to yield crude solid compound III. Yield: 1.35 gm Step-3: To the stirring solution of compound-III (1.35 gm, 1.66 mmol)) in dichloromethane (20 ml) was added into 15% Dess-Martin periodinane reagent solution in DCM (5.6 ml, 2 mmol) and stirred it at room temperature under nitrogen for 30 minutes. The reaction mixture was diluted with 20 ml (1:1) 10% Sodium thiosulphate and sat. sodium bicarbonate solution. The organic layer was separated and washed with water and then dried it over $Na_2SO_4$. and evaporated under reduced pressure to obtain compound IV which was purified by column chromatography (15% Acetone-Hexane). Yield: 1.3 gm.

Step-4: Compound-IV (1.3 gm, 1.60 mmol) was stirred in methanol (25 ml) for 4-5 hours at room temperature. It was concentrated. It was a mixture of two regio isomers. It was then separated by using preparative HPLC (Ammonium acetate:acetonitrile). Yield: Isomer-A: 160 mg Mass: m/z: 781.1 (M+H). M.P. 112-114° C., Isomer-B: 190 mg, Mass: m/z: 781.1 (M+H), M. P. 122-123° C.

Example 177

Compound of Formula I-e where Het is 1-(allyl)-1H-tetrazol-5-yl

Example 178

Compound of Formula I-e where Het is 2-(allyl)-2H-tetrazol-5-yl

Using the above procedure the title compounds were prepared Isomer A: Mass: m/z: 721.1 (M+H), M. P. 130-132° C. Isomer B: Mass: m/z: 721.1 (M+H), M. P. 170-172° C.

Example-179

Compound of Formula I-f where T is $CH_2CH=CH_2$

Step A: To the stirring solution of the Example 7 (15.52 mmol) in acetone was added $K_2CO_3$ (1.2 eq), allyl bromide (1.1 eq) and refluxed it for 48 hours. The reaction mixture was concentrated under vacuo. Water was added and filtered the residue. Dried it and purified it with column chromatography (EA; Hexane 24:76). Yield 70%.

Step B: To the stirring solution of the compound obtained in step A (16.6 mmol) in dry DCM was added Dess-Martin periodinane (15% solution in DCM) (1.2 eq) under $N_2$ atmosphere for 30 min. The reaction mixture was diluted with 1:1 10% sodiumthiosulphate solution and saturated sodium bicarbonate solution. The organic layer was separated and washed with water and brine; it was dried over $Na_2SO_4$ and concentrated under vacuo. The residue was purified with column chromatography (Ethylacetate:Hexane 20:80) to afford title compound, yield 50%.

Step C: To the stirring solution of the compound obtained in step B (0.48 mmol) in dry acetonitrile was added 70% HF in Pyridine complex (3.5 eq) The resulting mixture was stirred for 16 hours at room temperature under nitrogen atmosphere. The reaction mixture evaporated under vacuo. Water was added and extracted it in chloroform. Dried it over $Na_2SO_4$ and concentrated it. The residue was crystallized from ethanol:water (30:70) to give the title compound in yield 70%. MS 710 (M+H)$^+$.

Example-180

Compound of Formula I-f where T is CH₂-(5-methyl[1,2,4]oxadiazol-3-yl)

Step A: To a stirred solution of Example 7 (1.0 g, 1.3 mmol) in (10 ml) 1,4-dioxan was added (2 ml) N,N-dimethylformamide dimethylacetal and heated at 70° C. for 3 h. After completion of reaction solvent was evaporated under vacuum, water (30 ml) was added to the crude reaction mass and extracted with ethyl acetate (50 ml×3). Combined organic layer was dried over anhydrous sodium sulphate and then evaporated yielding crude solid. It was then purified by column chromatography using (Ethyl Acetate:n-hexane; 35:65) as a mobile phase. Pale solid was isolated. Yield: 480 mg, (48%).

Step B: To a stirred solution of the compound obtained in step A (480 mg, 0.6 mmol) in dichloromethane (10 ml) was added Dess Martin Periodinane reagent (2.0 ml, 1.2 equi., 15% solution) under $N_2$ atmosphere at room temperature for 30 min. After completion of reaction, additional 25 ml of dichloromethane was added and then quenched with 30 ml saturated aqueous solution of sodium thiosulphate:sodium bicarbonate. Organic layer was dried over anhydrous sodium sulphate and then distilled off under vacuum to obtain pale yellow solid. It was then purified by column chromatography using (Ethyl Acetate:n-Hexane; 30:70) as a mobile phase. Crystalline solid was isolated. Yield: 250 mg, (52%).

Step C: The compound obtained in step B (250 mg, 0.30 mmol) was dissolved in acetonitrile (10 ml). 70% HF-Pyridine solution (18 μl, 2.0 eq.) was added to the above solution and stirred at room temperature for overnight under $N_2$ atmosphere. After completion of reaction solvent was evaporated under vacuum to obtain crude product. Water (20 ml) was added to the crude product and extracted with dichloromethane (25 ml×3). Combined organic layer was dried over sodium sulphate and evaporated under vacuum to obtain crude white solid. It was then purified by column chromatography using $CHCl_3$:MeOH; 90:10) as a mobile phase to obtain title compound as white solid compound. Yield: 120 mg, (56%) MS 694 (M+H)⁺.

Example-181

Compound of Formula I-f where T is CO(CH₂)₂-(3-fluorophenyl)

Step-1: To the stirred solution of 3-(3-fluoro-phenyl)-propionic acid (0.321 g, 1.91 mmol) in dichloromethane (10 ml) was added dicyclohexylcarbodiimide (0.788 g, 3.82 mmol) followed by 1-hydroxy-benzotriazole (HOBT) (0.129 g, 0.955 mmol) at a temperature between 25-30° C. The reaction mixture was stirred for 30 minutes. To the reaction mixture was added Example-7 (1.0 g, 1.3 mmol) followed by N,N-dimethylamino pyridine (0.077 g, 0.636 mmol) under stirring and it was stirred for additional 1 hour at 25-30° C. temperature. The resultant mixture was filtered under suction, the filtrate was evaporated under vacuum to provide step-1 product as a thick liquid in 0.91 g quantity, which was used without purification for further reaction MS: m/z: 936.1 (M+1).

Step-2: To the stirred solution of N-chlorosuccinimide (0.97 g, 7.28 mmol) in dichloromethane (15 ml) at 0° C. was added dimethyl sulfide (1.6 ml, 12.12 mmol). The mixture was stirred at 0° C. for additional for 30 minutes. The reaction mixture was cooled to −40° C. and the solution of step-1 product (0.91 g, 0.97 mmol) dissolved in dichloromethane (10 ml) was added. The resulting reaction mixture was stirred at −40° C. temperature for 2 hr and then allowed to warm at 25-30° C. while stirring. Triethyl amine (0.980 ml, 9.71 mmol) was added to the reaction mixture at 25-30° C. and it was stirred for additional 30 minutes. The reaction mixture was quenched by pouring in aqueous saturated sodium bicarbonate solution and was extracted with dichloromethane (3×25 ml). The combined separated organic layer was dried over $Na_2SO_4$ and was evaporated to provide residue. The residue was purified by using silica gel column chromatography (10% acetone:hexanes) to provide step-2 product as a off white solid in 80.3% (0.73 g) yield. MS: m/z: 934.1 (M+1).

Step-3: Deprotection: To a mixture of step-2 compound (0.73 g, 0.782 mmol) and 70% HF-pyridine solution (26 μl, 0.912 mmol) in acetonitrile (10 ml), was added at 25-30° C. temperature for 2 hr. The solvent was evaporated under vacuum to obtain a crude residue. To the crude residue, water (20 ml) was added and the mixture was extracted with dichloromethane (3×25 ml). Combined organic layer was dried over $Na_2SO_4$ and evaporated under vacuum to obtain crude solid. The crude solid was purified by using silica gel column chromatography ($CHCl_3$:MeOH; 90:10) to obtain title compound as white solid compound in 78.3% (0.570 g) yield. Mp: 174-177° C., MS: m/z: 820.1 (M+1).

Following examples were prepared by using above procedure and by using carboxylic acid A.

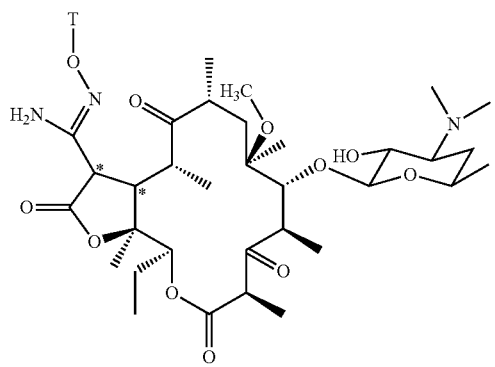

| Example | T | Carboxylic acid (A) | Mp (° C.) | Mass (M + 1) |
|---|---|---|---|---|
| 182 | CO(CH₂)₂-(3-(3-fluoro phenyl)-[1,2,4]oxadiazol-5-yl) | 3-[3-(3-fluoro-phenyl)-[1,2,4]oxadiazol-5-yl]-propionic acid | 166-168 | 888.1 |

-continued

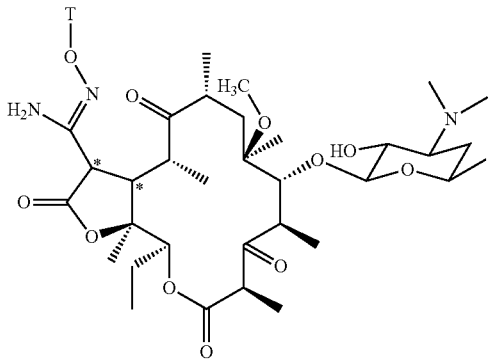

| Example | T | Carboxylic acid (A) | Mp (° C.) | Mass (M + 1) |
|---|---|---|---|---|
| 183 | $CO(CH_2)_2$-(3,4-dimethoxyphenyl) | 3-(3,4-dimethoxyphenyl)-propionic acid | 168-170 | 862.1 |
| 184 | $CO(CH_2)_2$-(4-methoxyphenyl) | 3-(4-methoxy-phenyl)-propionic acid | 154-160 | 803.1 |

Example-185

Compound of Formula I-f where T is $CH_2C\equiv CH$

Step-A: To the stirred solution of Example-7 (1.0 g, 1.3 mmol) in toluene (15 ml) was added potassium tert-butoxide (0.16 g, 1.43 mmol) and 18-crown-6-ether (0.048 g, 0.13 mmol) at 25-30° C. temperature. The reaction mixture was stirred for 10 min at 25-30° C. temperature. 3-bromo-propyne (127 µl, 1.43 mmol) was added to the reaction mixture and it was stirred for additional 1 hour. It was quenched by pouring it in aqueous saturated ammonium chloride solution (20 ml). The mixture was extracted with ethyl acetate (3×25 ml). Combined organic layer was dried over $Na_2SO_4$ and purified by using silica gel column chromatography (10% acetone: Hexane) to provide step-1 product as a pale yellow solid in 74% (0.77 g) yield. MS: m/z 825 (M+1).

Step-B: To the stirred solution of N-chlorosuccinimide (0.94 g, 7.0 mmol) in dichloromethane (20 ml) at 0° C. was added dimethyl sulfide (0.86 ml, 11.8 mmol). The reaction mixture was then stirred at 0° C. for 30 min. The step-1 product (0.77 g, 0.94 mmol) dissolved in dichloromethane (10 ml) was added to the reaction mixture at −40° C. The resulting reaction mixture was stirred at the 0° C. temperature for 2 hr and allowed to warm at 25-30° C. temperature under stirring. Triethyl amine (1.3 ml, 9.4 mmol) was added to the reaction mixture and stirred for additional 30 min. The mixture was poured in aqueous saturated sodium bicarbonate solution and extracted with dichloromethane (3×25 ml). The combined organic layer was dried over $Na_2SO_4$ and purified by using silica gel column chromatography (10% acetone: Hexane) to provide step-2 product as a off white solid in 80% (0.62 g) yield. MS: m/z: 823 (M+1).

Step-C: A mixture of step-2 product (0.62 g, 0.75 mmol) and 70% HF-pyridine solution (32 µl, 1.1 mmol) dissolved in acetonitrile (10 ml) was stirred at 25-30° C. for 2 hr. After completion of reaction, solvent was evaporated under vacuum to obtain a residue. Water (20 ml) was added to the residue and the mixture was extracted with dichloromethane (3×25 ml). Combined organic layer was dried over sodium sulphate and evaporated under vacuum to obtain a crude solid. The crude solid was purified by using silica gel column chromatography (10% MeOH:$CHCl_3$) to obtain title compound as white solid in 60% (0.37 g) yield. Mp: 202-204° C., MS: m/z: 709.1 (M+1).

Example-186

Compound of Formula I-f where T is $CH_2CH\equiv C$-(pyridin-2-yl)

Step-A: To the stirred suspension of $Pd(PPh_3)_2Cl_2$ (0.13 g, 0.18 mmol), CuI (46 mg, 0.24 mmol) and 2-iodoyridine (0.25 g, 1.2 mol) a solution of compound obtained in step A of the above example (1.0 g, 1.2 mmol) dissolved in diethyl amine (5.0 ml) was added at 25-30° C. temperature. The reaction mixture was stirred under inert atmosphere for additional 3 hr at 25-30° C. It was poured in ice cold water and extracted with ethyl acetate (3×25 ml). Combined organic layer was dried over $Na_2SO_4$ and evaporated under vacuum to provide a crude mass. The crude mass was purified by using silica gel column chromatography (15% acetone-Hexane) to yield step-1 product as a pale yellow solid in 60% (0.65 g) yield. MS: m/z: 901 (M+1)

Step-B: To the stirred solution of N-chlorosuccinimide (0.73 g, 5.5 mmol) in dichloromethane (20 ml) at 0° C. was added dimethyl sulfide (0.66 ml, 9.1 mmol). The reaction mixture was stirred under inert atmosphere at 0° C. for 30 min. The step-1 product (0.65 g, 0.73 mmol) dissolved in dichloromethane (10 ml) was added to the reaction mixture at −40° C. The resulting reaction mixture was stirred at the 0° C. temperature for 2 hr and allowed to warm at 25-30° C. temperature. Triethyl amine (1.0 ml, 7.3 mmol) was added to the reaction mixture and stirred for additional 30 min. The reaction mixture was poured in aqueous saturated sodium bicarbonate solution. The separated organic layer dried over $Na_2SO_4$ and purified by using silica gel column chromatography (10% Acetone:Hexane) to obtain step-2 product as a off white solid in 75% (0.49 g) yield. MS: m/z: 899 (M+1).

Step-C: A mixture of step-2 product (0.48 g, 0.53 mmol) and 70% HF-pyridine solution (23 µl, 0.8 mmol) dissolved in acetonitrile (10 ml) was stirred at 25-30° C. for 2 hr under $N_2$ atmosphere. After completion of reaction, solvent was evaporated under vacuum to obtain crude mass. Water (20 ml) was added to the crude mass and the mixture was extracted with dichloromethane (3×25 ml). Combined organic layer was dried over sodium sulphate and evaporated under vacuum to obtain crude solid. The crude solid was purified by using column chromatography (CHCl$_3$:MeOH; 90:10) to obtain title compound as white solid in 70% (0.29 g) yield. MS: m/z: 785 (M+1). Mp: 179-183° C.

Following examples were prepared by using above procedure and by using reactant A.

and was stirred for additional 30 minutes. The mixture was poured in aqueous saturated sodium bicarbonate solution (50 ml) and it was extracted with dichloromethane (3×25 ml). The combined organic layer was dried over Na$_2$SO$_4$ and was evaporated to provide a residue. The residue was purified by using silica gel column chromatography (10% acetone:hexanes) to provide step-2 product as a off white solid in 79% (0.67 g) yield. MS: m/z; 874 (M+1).

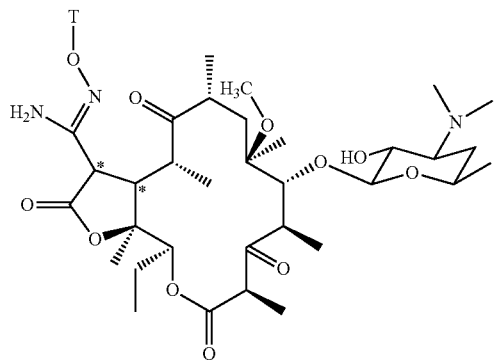

| Example | T | Reactant (A) | Mp (° C.) | Mass (M + 1) |
|---------|---|--------------|-----------|--------------|
| 187 | CH$_2$C≡C-(3-cyano)phenyl | 3-Iodo-benzo nitrile | 139-142 | 809.1 |
| 188 | CH$_2$C≡C-(3-fluoro)phenyl | 1-Fluoro-3-iodo-benzene | 175-178 | 802.1 |
| 189 | CH$_2$C≡C-(3-chloro)phenyl | 1-Chloro-3-iodo-benzene | 171-174 | 818.1 |
| 190 | CH$_2$C≡C-(3-methoxy) phenyl | 1-Iodo-3-methoxy-benzene | 168-171 | 814.1 |
| 191 | CH$_2$C≡C-(2-chloro pyridin-5-yl) | 2-Chloro-5-iodo-pyridine | 167-170 | 819.1 |
| 192 | CH$_2$C≡C-(2-fluoro pyridin-5-yl) | 2-Fluoro-5-iodo-pyridine | 173-176 | 803.1 |
| 193 | CH$_2$C≡C-(pyridin-3-yl) | 3-Iodo-pyridine | 132-137 | 785.1 |

Example-194

Compound of Formula I-f where T is CH$_2$-phenyl

Step-1: To the solution of Example-7 (1.0 g, 1.3 mmol) in toluene (10 ml) was added potassium tert-butoxide (0.160 g, 1.43 mmol), 18-crown-6-ether (0.048 g, 0.13 mmol), followed by benzyl bromide (182 μl, 1.56 mmol) at a 25-30° C. The reaction mixture was stirred at 25-30° C. temperature for 1 hour. After completion of the reaction, the reaction mixture was poured in saturated aqueous ammonium chloride solution (20 ml). The mixture was extracted with ethyl acetate (3×25 ml). Combined organic layer was dried over Na$_2$SO$_4$ and evaporated under vacuum to provide a residue. The residue was purified by using silica gel column chromatography (10% acetone:hexanes) to provide step-1 product as a off white solid in 76.2% (0.85 g) yield. MS: m/z: 876 (M+1)

Step-2: Method A: To the stirred solution of N-chlorosuccinimide (0.97 g, 7.28 mmol) in dichloromethane (15 ml) at 0° C. was added dimethyl sulfide (1.6 ml, 12.12 mmol). The reaction mixture was stirred at 0° C. for additional 30 minutes. The complex was cooled to –40° C. and the solution of step-1 product (0.85 g, 0.97 mmol) dissolved in dichloromethane (10 ml) was added. The resulting reaction mixture was stirred at –40° C. temperature for 2 hr and allowed to warm at 25-30° C. under stirring. Triethyl amine (0.980 ml, 9.71 mmol) was added to the reaction mixture at 25-30° C.

Method B: Alternatively, oxidation was carried our by using Dess-martin periodinane reagent as follows: To the stirred solution of the step-1 product (1.5 g, 1.6 mmol) in dichloromethane (10 ml), was added Dess-martin periodinane (5.0 ml, 1.76 mmol, 15% solution in dichloromethane). The reaction mixture was stirred at a temperature 25-30° C. for 30 min. The reaction mixture was poured in 1:1 mixture of aqueous saturated sodium bicarbonate solution and aqueous saturated sodium thiosulphate solution and it was extracted with dichloromethane (3×25 ml). The combined organic layer was dried over Na$_2$SO$_4$ and purified by using silica gel column chromatography (10% Acetone:Hexane) to provide step-2 product in 46% (0.7 g) yield. MS: m/z; 874 (M+1).

Step-3: To a mixture of step-2 product (0.67 g, 0.76 mmol) and 70% HF-pyridine solution (26 μl, 0.912 mmol) in acetonitrile (10 ml), was stirred at 25-30° C. temperature for 2 hr. The solvent was evaporated under vacuum to obtain a crude residue. To the crude residue, water (20 ml) was added and the mixture was extracted with dichloromethane (3×25). Combined organic layer was dried over Na$_2$SO$_4$ and evaporated under vacuum to obtain a crude solid. The crude solid was purified by using silica gel column chromatography (CHCl$_3$:MeOH; 90:10) to afford title compound as white solid compound in 76.2% (0.51 g) yield. MS: m/z: 761.1 (M+1). Mp: 200-204° C.

Following examples were prepared by using above procedure and by using reactant A.

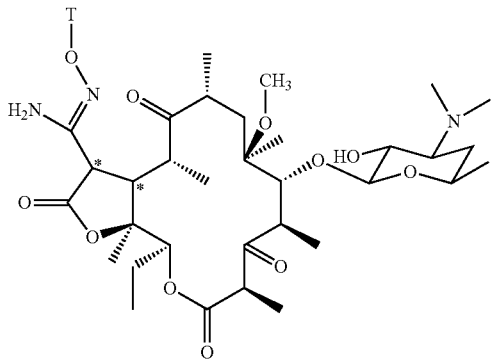

| Example | T | Reactant (A) | Mp (° C.) | Mass (M + 1) |
|---|---|---|---|---|
| 195 | CH$_2$-(4-methoxyphenyl) | 1-bromomethyl-4-methoxy-benzene | 184-187 | 790.1 |
| 196 | CH$_2$-(3-chlorophenyl) | 1-bromomethyl-3-chloro-benzene | 212-214 | 794.1. |
| 197 | CH$_2$-(3-methoxyphenyl) | 1-bromomethyl-3-methoxy-benzene | 212-215 | 790.1 |
| 198 | CH$_2$-(4-(1H-[1,2,4]triazol)phenyl) | 1-(4-bromo methylphenyl)-1H-[1,2,4]triazole | 150-154 | 827.1 |
| 199 | CH$_2$-(4-(isopropyl)phenyl) | 1-Bromomethyl-4-isopropyl-benzene | 189-191 | 802.1 |
| 200 | CH$_2$-(2-fluorophenyl) | 1-Bromomethyl-2-fluoro-benzene | 176-179 | 778.1 |
| 201 | CH$_2$-(4-(pyrimidin-5-yl)phenyl) | 5-(4-bromo methyl-phenyl)-pyrimidine | 164-167 | 838.1 |
| 202 | CH$_2$-(4-(pyridin-2-yl)phenyl) | 2-(4-bromo methyl-phenyl)-pyridine | 170-172 | 837.1 |
| 203 | CH$_2$C(=CH$_2$)CH$_3$ | 3-Chloro-2-methyl-propene | 174-177 | 714.1 |
| 204 | CH$_2$CH=CHCH$_3$ | 1-Chloro-but-2-ene | 221-224 | 724.1 |
| 205 | CH$_2$CH=C(CH$_3$)$_2$ | 1-Chloro-3-methyl-but-2-ene | 244-248 | 738.1 |
| 206 | CH$_2$C(F)=CH$_2$ | 3-Chloro-2-fluoro-1-propene | 174-176 | 728.1 |

Example-207

Compound of Formula I-f where T is CH$_2$CH=CH-(pyridin-3-yl)

Step A: To the stirring solution of Step A product from Example 179 (1.5 g, 1.81 mmol) in DMF (15 ml) was added sodium acetate (0.24 g, 2.73 mmol). To the above solution Tetrakis triphenyl phosphine palladium (0) (0.21 g, 0.18 mmol) and 3-bromopyridine (0.195 µl, 1.99 mmol) were added and stirred the reaction mixture for 12 hour at 120° C. temperature. The reaction mixture was then poured in sat. ammonium chloride solution (20 ml) and extracted with ethyl acetate (50 ml×3). Combined organic layer was dried over Na$_2$SO$_4$ it was then purified over silica gel column chromatography (18% Acetone:Hexane), yield (0.65 g, 53%).

Step B: To the stirred solution of step-1 compound (0.65 g, 0.72 mmol) in DCM (130 ml) was added Dess-Martin perriodinane reagent (15% solution in DCM) (3.4 ml, 1.18 mmol) at 25-30° C. temperature. The reaction mixture was stirred further for 30 min. The reaction mixture was quenched with 1:1 mixture of aqueous saturated sodium bicarbonate solution and aqueous sodium thiosulfate solution (2×200 ml) the organic layer was washed with brine (100 ml). Combined organic layer was dried over Na$_2$SO$_4$ and concentrated under vacuum to provide a crude mass. The crude material was purified by flash column chromatography using acetone:hexane 2.2:7.8 mixture to provide pale yellow solid in 45% (0.35 g) yield.

Step C: To the solution of compound obtained from above step (0.35 g, 0.37 mmol) in acetonitrile (15 ml) was added 70% hydrogen fluoride in pyridine (16 µl, 0.58 mmol) under inert atmosphere and stirred for 3 h. The residue obtained after evaporation of solvent under reduced pressure was dissolved in ethyl acetate (15 ml) and washed with water (2×10 ml). The organic layer was dried over Na$_2$SO$_4$ and evaporated under reduced pressure to provide crude solid which on trituration in diethyl ether afforded white solid as the title compound. Yield: 0.180 g (60%), Mass: m/z: 787.1 (M+H), Mp: 212-215° C.

Following examples were prepared by using above procedure and by using reactant A.

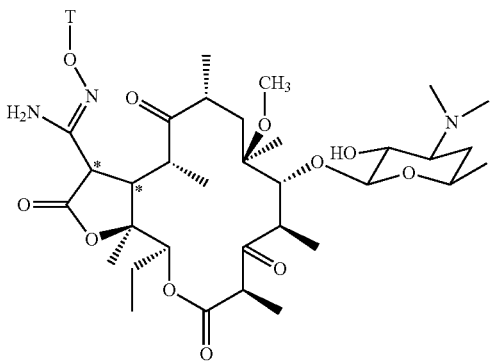

| Example | T | Reactant (A) | Mp (°C.) | Mass (M+1) |
|---|---|---|---|---|
| 208 | CH$_2$CH=CH-phenyl | iodobenzene | 202-205 | 786.1 |
| 209 | CH$_2$CH=CH-(4-trifluoromethyl)phenyl | 1-iodo-4-trifluoromethyl-benzene | 96-100 | 854.1 |
| 210 | CH$_2$CH=CH-(3-trifluoromethyl)phenyl | 1-iodo-3-trifluoromethyl-benzene | 206-210 | 854.1 |
| 211 | CH$_2$CH=CH-(3-fluoro)phenyl | 1-fluoro-3-iodo-benzene | 214-216 | 804.1 |
| 212 | CH$_2$CH=CH-(3-chloro)phenyl | 1-chloro-3-iodo-benzene | 154-158 | 820.1 |
| 213 | CH$_2$CH=CH—(pyrimidin-5-yl) | 5-Iodo-pyrimidine | 158-160 | 788.1 |

Example-214

Compound of Formula I-f where T is CH$_2$CONH-(3-chlorophenyl)

Step-1: To the stirred solution of m-chloro aniline (2.0 g, 1.57 mmol) in THF (20 ml) was added triethyl amine (2.62 ml, 1.88 mmol), bromoacetyl bromide (1.51 ml, 1.73 mmol) at 5° C. and the reaction mixture was stirred for 1 hour at 25-30° C. temperature. The reaction mixture was poured in aqueous saturated ammonium chloride solution (20 ml) and extracted with ethyl acetate (3×25 ml). Combined organic layer dried over Na$_2$SO$_4$ and distilled under reduced pressure. Yellow coloured compound was obtained as a step-1 product and utilized for the next step.

Step-2: To the stirred solution of Example-7 (2.00 g, 2.50 mmol) in toluene (10 ml) was added potassium hydride (3.41 g, 0.30 mmol) and 18-crown-6-ether (0.08 mg, 0.30 mmol) at 25-30° C. temperature. The reaction mixture was stirred for additional 10 min. and step-1 product 2-bromo-N-(3-chlorophenyl)-acetamide (0.69 g, 2.81 mmol) was added. The reaction mixture was stirred for 1 hour at 25-30° C. temperature. It was poured in aqueous saturated ammonium chloride solution (30 ml) and extracted with ethyl acetate (3×25 ml). Combined organic layer was dried over Na$_2$SO$_4$ and purified by using silica gel column chromatography (10% Acetone:Hexane) to provide step-2 product as a off white solid in 70% (1.68 g) yield. MS: m/z: 953 (M+1).

Step-3: To the stirred solution of N-chlorosuccinimide (1.77 gm, 13.22 mmol) in dichloromethane (20 ml) at 0° C. was added dimethyl sulfide (1.62 ml, 22.00 mmol). The reaction mixture was stirred at 0° C. for next 30 min. The Step-1 product (1.68 gm, 1.76 mmol) dissolved in dichloromethane (10 ml) was added to the reaction mixture at −40° C. The resulting reaction mixture was stirred at the same temperature for 2 hr and allowed to warm at 25-30° C. temperature. Triethyl amine (2.45 ml, 17.62 mmol) was added to the reaction mixture and stirred for additional 30 min. The reaction mixture was poured in aqueous saturated sodium bicarbonate solution and extracted with dichloromethane (3×25 ml). The combined organic layer dried over Na$_2$SO$_4$ and purified by using silica gel column chromatography (10% acetone:hexane) to provide step-3 product as a off white solid in 80% (1.34 g) yield. MS: m/z: 951 (M+1).

Step-4: A mixture of step-3 product (1.34 gm, 1.40 mmol) and 70% HF-pyridine solution (60 µl, 2.16 mmol) in acetonitrile (10 ml) was stirred at 25-30° C. for 2 hr. After completion of reaction, solvent was evaporated under vacuum to obtain crude mass. Water (20 ml) was added to the crude mass and extracted with dichloromethane (3×25 ml). Combined organic layer was dried over sodium sulphate and evaporated under vacuum to obtain crude solid. The crude solid was purified by using silica gel column chromatography (10% MeOH:CHCl$_3$) to obtain title compound as white solid in 35% (0.42 g) yield. MS: m/z: 838 (M+1). Mp: 183-186° C.

Following examples were prepared by using above procedure and by using reactant A.

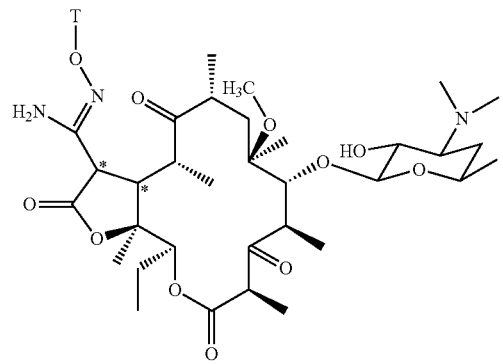

| Example | T | Reactant (A) | Mp (°C.) | Mass (M+1) |
|---|---|---|---|---|
| 215 | CH$_2$CONH-(3-fluorophenyl) | 2-bromo-N-(3-fluorophenyl)-acetamide | 176-178 | 821.1 |
| 216 | CH$_2$CO-(4-phenyl-piperazin-1-yl) | 2-bromo-1-(4-phenyl-piperazin-1-yl-ethanone | 214-218 | 872.1 |
| 217 | CH$_2$CONH$_2$ | 2-bromoacetamide | 220-222 | 727.1 |
| 218 | CH$_2$CON(CH$_3$)$_2$ | 2-bromo-N,N-dimethylacetamide | 210-214 | 755.1 |
| 219 | CH$_2$CONH-(cyclopropyl) | 2-bromo-N-cyclopropyl-acetamide | 214-218 | 767.1 |

Example-220

Compound of Formula I-f where T is CH$_2$-(5-(pyridin-3-yl)[1,3,4]oxadiazol-2-yl)

Step-1: To a mixture of 3-cyanopyridine (12 g, 115 mmol) and trimethylsilyl azide (20 ml, 150 mmol), was added a solution of 0.1 M tetra-n-butylammonium fluoride in THF (57 ml, 56 mmol) at 25-30° C. temperature. The resulting mixture was heated at 80° C. for overnight. The mixture is allowed to warm at 25-30° C. temperature and then quenched in ice-water mixture. Solid precipitated out was filtered and washed with water (2×25 ml) and dried under vacuum to provide step-1 compound in 62% (10.5 g) yield. MS: 148 (M+1).

Step-2: To the stirred solution of 3-(1H-tetrazol-5-yl)-pyridine (10.5 g, 71.42 mmol) in toluene (50 ml) was added chloroacetic anhydride (25 g, 92.80 mmol) and resulting mixture was heated at 100° C. for 2-3 hours. The reaction mixture was allowed to warm at 25-30° C. temperature. The mixture was quenched with saturated aqueous sodium bicarbonate solution (500 ml) and extracted with chloroform (2×200 ml). The combined organic layer was washed with brine, dried over $Na_2SO_4$ and concentrated under reduced pressure to provide a crude mass. The crude mass was purified over silica gel column chromatography to provide title compound in 56% (7.8 g) yield. MS: 196 (M+1).

Step-3: To the stirred solution of potassium hydride (5.5 g, 41 mmol) and 18-crown-6 (1.1 g, 4.1 mmol) in toluene (200 ml) was added Example-7 (25 g, 32 mmol). It was allowed to stir at 25-30° C. temperature for 30 min. (5-chloromethyl-1,3,4-oxadiazole-2-yl)-pyridine (7.8 g, 38 mmol) was added to the reaction mixture. The reaction mixture was stirred at 25-30° C. temperature for 30 minutes. It was quenched with aqueous saturated ammonium chloride solution (500 ml). The organic layer was washed with brine (500 ml), dried over $Na_2SO_4$ and concentrated under vacuum to provide a crude mass. The crude mass was purified by flash column chromatography (acetone:hexane 2.5:7.5) to provide off white solid in 43% (13 g) yield. MS: m/z 945 (M+1).

Step-4: To the stirred solution of step-3 compound (13 g, 14 mmol) in DCM (130 ml) was added Dess-Martin periodinane reagent (15% solution in DCM) (58 ml, 21 mmol) at 25-30° C. temperature. The reaction mixture was stirred further for 30 min. The reaction mixture was quenched with 1:1 mixture of aqueous saturated sodium bicarbonate solution and aqueous sodium thiosulfate solution (2×200 ml) the organic layer was washed with brine (100 ml). Combined organic layer was dried over $Na_2SO_4$ and concentrated under vacuum to provide a crude mass. The crude material was purified by flash column chromatography using acetone:hexane 2.2:7.8 mixture to provide pale yellow solid in 45% (7.4 g) yield. MS: m/z: 943 (M+1).

Step-5: A mixture of step-4 compound (7.4 g, 7.8 mmol) in acetonitrile (74 ml) and 70% HF-pyridine complex (0.3 ml, 12 mmol) was stirred at 25-30° C. temperature for 3-4 hours. The reaction mixture was concentrated under reduced pressure and water was added and the mixture was extracted with DCM (2×40 ml). Combined organic layer was dried over $Na_2SO_4$ and concentrated under vacuum. The crude mass was purified by flash column chromatography (MeOH:$CHCl_3$ 1.2:8.8) to give title compound as a white solid in 45% (3.4 g) yield. MS: m/z: 829 (M+1). Mp: 212-214° C.

Following examples were prepared by using above procedure and by using reagent A.

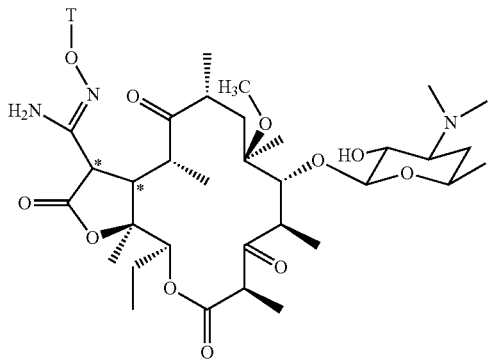

| Example | T | Reagent A | Mp (° C.) | Mass (M + 1) |
|---|---|---|---|---|
| 221 | $CH_2$-(5-phenyl[1,3,4]oxadiazol-2-yl) | 2-chloromethyl-5-phenyl [1,3,4]-oxadiazole | 134-136 | 829.1 |
| 222 | $CH_2$-(5-(3-fluorophenyl)[1,3,4]oxadiazol-2-yl) | 2-chloromethyl-5-(3-fluoro-phenyl)-[1,3,4]-oxadiazole | 125-127 | 845.1 |
| 223 | $CH_2$-(5-(4-methoxy phenyl)[1,3,4]oxadiazol-2-yl) | 2-chloromethyl-5-(4-methoxy-phenyl)-[1,3,4]-oxadiazole | 130-133 | 857.1 |
| 224 | $CH_2$-(5-(pyridin-2-yl)[1,3,4]oxadiazol-2-yl) | 2-(5-chloromethyl-[1,3,4]-oxadiazol-2-yl)-pyridine | 205-208 | 829.1 |
| 225 | $CH_2$-(5-(pyrazin-2-yl)[1,3,4]oxadiazol-2-yl) | 2-(5-chloromethyl-[1,34,]-oxadiazol-2-yl)-pyrazine | 188-190 | 831.1 |
| 226 | $CH_2$-(5-(3,5-dimethoxy phenyl)[1,3,4]oxadiazol-2-yl) | 2-chloromethyl-5-(3,5-dimethoxy-phenyl)-[1,3,4]-oxadiazole | 171-179 | 887.1 |
| 227 | $CH_2$-(5-(pyrimidin-2-yl)[1,3,4]oxadiazol-2-yl) | 2-(5-chloromethyl-[1,3,4]-oxadiazol-2-yl)-pyrimidine | 187-191 | 831.1 |
| 228 | $CH_2$-((5-cyclopropyl)-[1,3,4]oxadiazol-2-yl) | 2-chloromethyl-5-cyclopropyl-[1,3,4]-oxadiazole | 186-192 | 791.1 |

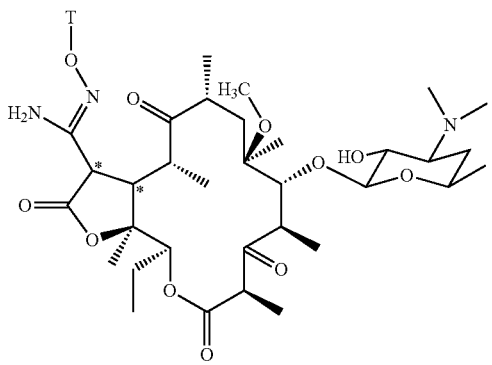

| Example | T | Reagent A | Mp (° C.) | Mass (M + 1) |
|---|---|---|---|---|
| 229 | CH$_2$-(5-(6-methoxy-pyridin-2-yl)[1,3,4]oxadiazol-2-yl) | 2-(5-chloromethyl-[1,3,4]-oxadiazol-2-yl)-6-methoxy-pyridine | 225-230 | 860.1 |
| 230 | CH$_2$-(5-(5-methyl-pyridin-2-yl)[1,3,4]oxadiazol-2-yl) | 2-(5-chloromethyl-[1,3,4]-oxadiazol-2-yl)-5-methyl-pyridine | — | 844.1 |
| 231 | CH$_2$-(5-(5-cyclopropyl-pyridin-2-yl)[1,3,4]oxadiazol-2-yl) | 2-(5-chloromethyl-[1,3,4]-oxadiazol-2-yl)-5-cyclopropyl-pyridine | — | 870.1 |
| 232 | CH$_2$-(5-(5-cyano-pyridin-2-yl)[1,3,4]oxadiazol-2-yl) | 2-(5-chloromethyl-[1,3,4]-oxadiazol-2-yl)-5-cyano-pyridine | — | 855.1 |
| 234 | CH$_2$-(5-(5-dimethyl amino-pyridin-2-yl)[1,3,4]oxadiazol-2-yl) | 2-(5-chloromethyl-[1,3,4]-oxadiazol-2-yl)-5-dimethyl amino-pyridine | — | 874.1 |
| 235 | CH$_2$-(5-(5-methoxy-pyridin-2-yl)[1,3,4]oxadiazol-2-yl) | 2-(5-chloromethyl-[1,3,4]-oxadiazol-2-yl)-5-methoxy-pyridine | — | 860.1 |
| 236 | CH$_2$-(5-(5-fluoro-pyridin-2-yl)[1,3,4]oxadiazol-2-yl) | 2-(5-chloromethyl-[1,3,4]-oxadiazol-2-yl)-5-fluoro-pyridine | — | 848.1 |
| 237 | CH$_2$-(5-(5-chloro-pyridin-2-yl)[1,3,4]oxadiazol-2-yl) | 2-(5-chloromethyl-[1,3,4]-oxadiazol-2-yl)-5-chloro-pyridine | — | 864.1 |
| 238 | CH$_2$-(5-(pyrimidin-5-yl[1,3,4]oxadiazol-2-yl) | 5-(5-chloromethyl-[1,3,4]-oxadiazol-2-yl)-pyrimidine | — | 831.1 |

Example-239

Compound of Formula I-f, where T is CH$_2$-(3-(pyridin-2-yl)[1,2,4]oxadiazol-5-yl)

Step-1: To the stirred suspension of hydroxylamine hydrochloride (8.01 g, 120 mmol) in methanol (100 ml) was added sodium bicarbonate (10.50 g, 130 mmol) followed by pyridine-2-carbonitrile (10 g, 96 mmol). The reaction mixture was refluxed for 2 hours. The solvent was removed under vacuum to provide a residue. Water (200 ml) was added to the residue. The solid separated was filtered under suction and washed with water (100 ml) dried under vacuum to provide step-1 product as a white solid in 93% (12.5 g) yield. MS: m/z: 138 (M+1).

Step-2: To the stirred suspension of step-1 product (12.50 g, 91.2 mmol) in acetone (100 ml), chloroacetyl chloride (7.36 ml, 120 mmol) was added drop-wise at 25-30° C. temperature. The reaction mixture was stirred for 30 minutes. The solid separated was filtered and stirred with saturated aqueous NaHCO$_3$ solution (200 ml). The suspension was filtered and washed with water, dried under vacuum to provide step-2 product as a off white solid in 83% (18 g) yield. The solid was used as it is for the next step. MS: m/z: 214.6 (M+1).

Step-3: The step-2 product (18 g, 85 mmol) was refluxed in toluene (200 ml) along with 4 Å molecular sieves for 2 hrs. The reaction mixture was concentrated under vacuum to provide a crude residue. The crude residue was triturated with diethyl ether to afford 5-chloromethyl-1,2,4-oxadiazol-3-yl)-pyridine, as step-3 product as a off white solid in 96% (16 g) yield. MS: m/z: 197.6 (M+1).

Step-4: To the stirred mixture of potassium hydride (2.1 g, 17 mmol), 18-crown-6 (0.33 g, 1.2 mmol) in toluene (100 ml) was added Example-7 (10 g, 13 mmol). The reaction mixture was stirred at 25-30° C. temperature for 30 min and step-3 product, 2-(5-chloromethyl-1,2,4-oxadiazol-3-yl)-pyridine (3.2 g, 14 mmol) dissolved in toluene (5 ml) was added to the reaction mixture. It was stirred for additional 30 min. The reaction mixture was quenched by addition of saturated aqueous ammonium chloride solution (250 ml). Layers were separated. The organic layer was washed with brine (250 ml), dried over Na$_2$SO$_4$, concentrated under vacuum to provide crude solid. The crude solid was purified by flash column chromatography (acetone:hexane 2.5:7.5) to isolate step-4 product as a off white solid in 58% (7.0 g) yield. MS: m/z: 945 (M+1).

Step-5: To a stirred solution of N-chlorosuccinimide (8.66 g, 56 mmol) in dry toluene (100 ml) at 0° C. was added dimethyl sulfide (7.7 ml, 93 mmol). A white precipitate appeared. The mixture was cooled to −40° C., and a solution of step-4 product (7.0 g, 7.4 mmol) in DCM (30 ml) was added over 30 min. Stirring was continued for 3 hours at same temperature. TEA (12.5 ml, 74 mmol) was added to the reaction mixture and the reaction mixture was allowed warm at 25-30° C. temperature. It was quenched with saturated aqueous sodium bicarbonate solution (100 ml). The organic layer was washed with brine (100 ml), dried over $Na_2SO_4$ concentrated under vacuum to provide a crude mass. The crude mass was purified by using silica gel column chromatography (acetone:Hexane; 20:80) to isolate step-5 product as a off white solid in 67% (4.7 g) yield. MS: m/z: 943 (M+1).

Step-6: A mixture of the step-5 product (4.7 g, 5.0 mmol) and 70% HF-Pyridine complex (0.17 ml, 7.5 mmol) in acetonitrile (40 ml) was stirred at 25-30° C. temperature for 3-4 hours. The reaction mixture was concentrated under vacuum to provide a residue and to the residue, water (50 ml) was added. The product was extracted in DCM (2×30 ml), dried over $Na_2SO_4$ and concentrated under vacuum to provide a crude solid. The crude solid was purified by using flash column chromatography ($MeOH:CHCl_3$; 1.5:8.5) to give title compound in 61% (2.5 g) yield. MS: m/z: 829 (M+1) Mp: 172-175° C.

Following examples were prepared by using above procedure and by using Reagent A in the place of 2-(5-chloromethyl-1,2,4-oxadiazol-3-yl)-pyridine.

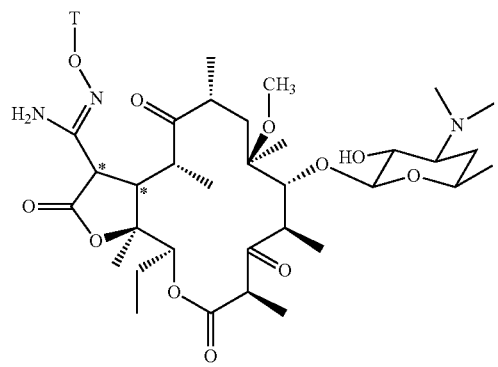

| Example | T | Reagent (A) | Mp (° C.) | Mass (M + 1) |
|---|---|---|---|---|
| 240 | $CH_2$(3-phenyl[1,2,4]oxadiazol-5-yl) | 5-chloromethyl-3-phenyl-[1,2,4]-oxadiazole | 162-165 | 827.1 |
| 241 | $CH_2$-(3-(3-fluorophenyl)[1,2,4]oxadiazol-5-yl) | 5-chloromethyl-3-fluoro phenyl-[1,2,4]-oxadiazole | 150-152 | 845.1 |
| 242 | $CH_2$-(3-(3-chlorophenyl)[1,2,4]oxadiazol-5-yl) | 5-chloromethyl-3-chloro phenyl-[1,2,4]oxadiazole | 154-157 | 861.1 |
| 243 | $CH_2$-(3-(4-methoxyphenyl)[1,2,4]oxadiazol-5-yl) | 5-chloromethyl-4-methoxy-phenyl-[1,2,4] oxadiazole | 173-176 | 857.1 |
| 244 | $CH_2$-(3-(pyridin-3-yl)[1,2,4]oxadiazol-5-yl) | 3-(5-chloromethyl-[1,2,4]oxadiazol-3-yl)-pyridine | 210-214 | 829.1 |
| 245 | $CH_2$-(3-(4-chlorophenyl)[1,2,4]oxadiazol-5-yl) | 5-chloromethyl-4-chlorophenyl-[1,2,4]oxadiazole | 135-138 | 861.1 |
| 246 | $CH_2$-(3-(3,5-dimethoxy phenyl)[1,2,4]oxadiazol-5-yl) | 5-chloromethyl-3,5-dimethoxy phenyl-[1,2,4] oxadiazole | 154-158 | 887.1 |
| 247 | $CH_2$-(3-(pyrimidin-2-yl)[1,2,4]oxadiazol-5-yl) | 2-(5-chloromethyl-[1,2,4] oxadiazol-3-yl)-pyrimidine | 162-165 | 831.1 |
| 248 | $CH_2$-(3-cyclopropyl[1,2,4]oxadiazol-5-yl) | 5-chloromethyl-3-cyclo propyl-[1,2,4]oxadiazole | 176-178 | 792.1 |
| 249 | $CH_2$-(3-(6-methyl pyridin-2-yl)[1,2,4] oxadiazol-5-yl) | 2-(5-chloromethyl-[1,2,4] oxadiazol-3-yl)-6-methyl-pyridine | 202-205 | 842.1 |
| 250 | $CH_2$-(3-(3-methyl pyridin-2-yl)[1,2,4] oxadiazol-5-yl) | 2-(5-chloromethyl-[1,2,4] oxadiazol-3-yl)-3-methyl-pyridine | 194-198 | 842.1 |
| 251 | $CH_2$-(3-(5-methyl-pyridin-2-yl)[1,2,4] oxadiazol-5-yl) | 2-(5-chloromethyl-[1,2,4]-oxadiazol-3-yl)-5-methyl-pyridine | — | 844.1 |
| 252 | $CH_2$-(3-(5-cyclopropyl-pyridin-2-yl)[1,2,4] oxadiazol-5-yl) | 2-(5-chloromethyl-[1,2,4]-oxadiazol-3-yl)-5-cyclo propyl-pyridine | — | 870.1 |
| 253 | $CH_2$-(3-(5-cyano-pyridin-2-yl)[1,2,4]oxadiazol-5-yl) | 2-(5-chloromethyl-[1,2,4]-oxadiazol-3-yl)-5-cyano-pyridine | — | 855.1 |

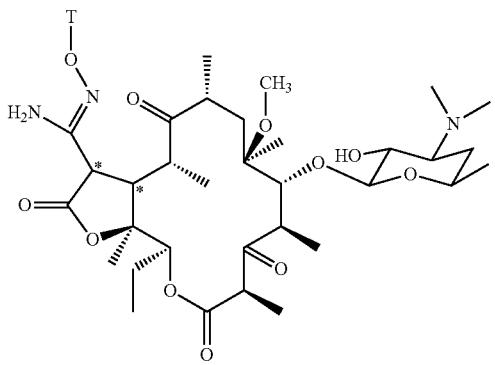

| Example | T | Reagent (A) | Mp (° C.) | Mass (M + 1) |
|---|---|---|---|---|
| 254 | $CH_2$-(3-(5-dimethyl amino-pyridin-2-yl)[1,2,4]oxadiazol-5-yl) | 2-(5-chloromethyl-[1,2,4]-oxadiazol-3-yl)-5-dimethyl amino-pyridine | — | 874.1 |
| 255 | $CH_2$-(3-(5-methoxy-pyridin-2-yl)[1,2,4]oxadiazol-5-yl) | 2-(5-chloromethyl-[1,2,4]-oxadiazol-3-yl)-5-methoxy-pyridine | — | 860.1 |
| 256 | $CH_2$-(3-(5-fluoro-pyridin-2-yl)[1,2,4]oxadiazol-5-yl) | 2-(5-chloromethyl-[1,2,4]-oxadiazol-3-yl)-5-fluoro-pyridine | — | 848.1 |
| 257 | $CH_2$-(3-(5-chloro-pyridin-2-yl)[1,2,4]oxadiazol-5-yl) | 2-(5-chloromethyl-[1,2,4]-oxadiazol-3-yl)-5-chloro-pyridine | — | 864.1 |
| 258 | $CH_2$-(3-(pyrimidine-5-yl)[1,2,4]oxadiazol-5-yl) | 5-(5-chloromethyl-[1,2,4]-oxadiazol-3-yl)-pyrimidine | — | 831.1 |

Example-259

Compound of Formula I-f where T is $CH_2$-(5-(pyridin-3-yl)[1,2,4]oxadiazol-3-yl)

Step-1: To the stirred solution of 2-chloroacetamidoxime (1.0 g, 9.2 mmol, prepared as per the procedure given in PCT/US02/22897) in toluene (15 ml) was added nicotinyl chloride (1.37 g, 9.67 mmol) and heated at 110° C. for 4 hr. The reaction mixture was diluted with ethyl acetate (50 ml) and washed with aqueous saturated sodium bicarbonate solution (2×25). Organic layer was evaporated under vacuum to yield the crude product. The crude product was purified using silica gel column chromatography (15% Acetone-Hexane) to give 2-(3-chloromethyl-[1,2,4]-oxadiazole-5-yl)-pyridine in 55% (0.550 g) yield. MS: m/z: 196.7 (M+1).

Step-2: The 2-(3-chloromethyl-[1,2,4]-oxadiazol-5-yl)-pyridine (0.550 g, 2.8 mmol) was dissolved in acetone (20 ml). To the clear solution, sodium iodide (0.843 g, 5.62 mmol) and tetra-n-butyl-ammonium iodide (0.259 g, 0.70 mmol) were added. The reaction mixture was refluxed for 2 hr. It was quenched by addition of water (20 ml) and extracted with ethyl acetate (2×25 ml). The combined organic layer was dried over $Na_2SO_4$ and evaporated under vacuum to yield 2-(3-Iodomethyl-[1,2,4]oxadiazole-5-yl)-pyridine in 90% (0.750 g) yield. MS: m/z: 288.1 (M+1).

Step-3: To the stirring solution of Example-7 (1.0 gm, 1.3 mmol) in toluene (10 ml) was added potassium hydride (0.16 g, 1.43 mmol) and 18-crown-6-ether (0.048 g, 0.13 mmol) at a temperature 25-30° C. and stirred for 10 min. To this reaction mixture, step-2 product, 2-(3-iodomethyl-[1,2,4]oxadiazole-5-yl)-pyridine (0.401 g, 1.43 mmol) was added and stirred for 1 hour at temperature 25-30° C. The reaction mixture was then poured in aqueous saturated ammonium chloride solution (20 ml) and the mixture was extracted with ethyl acetate (3×25 ml). Combined organic layer was dried over $Na_2SO_4$ and purified by using silica gel column chromatography (15% Acetone:Hexane). To afford step-3 product as yellow solid in 65% (0.780 g) yield. MS: m/z: 946.3 (M+1).

Step-4: To the stirred solution of N-chlorosuccinimide (0.826 g, 6.18 mmol) in toluene (15 ml) at 0° C. was added dimethyl sulfide (757 µl, 10.3 mmol) to provide a complex. The complex was stirred at 0° C. for additional for 30 minutes. The complex was cooled to and the solution of step-3 product (0.780 g, 0.825 mmol) dissolved in toluene or dichloromethane (10 ml) was added. The resulting reaction mixture was stirred at –40° C. temperature for 2 hr and then allowed to warm at 25-30° C. while stirring. Triethyl amine (1.14 ml, 8.25 mmol) was added to the reaction mixture at 25-30° C. and it was stirred for additional 30 minutes. The reaction mixture was poured in aqueous saturated sodium bicarbonate solution and the mixture was extracted with dichloromethane (3×25 ml). The combined separated organic layer was dried over $Na_2SO_4$ and was evaporated to provide residue. The residue was purified by using silica gel column chromatography (10% acetone:hexanes) to provide step-4 product as a off white solid in 75% (0.582 g) yield. MS: m/z: 944.3 (M+1).

Step-5: A mixture of step-4 compound (0.582 g, 0.617 mmol) and 70% HF-Pyridine solution (19.3 µl, 0.678 mmol) in acetonitrile (10 ml), was stirred at 25-30° C. temperature for 2 hr. The solvent was evaporated under vacuum to obtain a crude residue. To the crude residue, water (20 ml) was added and the mixture was extracted with dichloromethane (25 ml×3). Combined separated organic layer was dried over $Na_2SO_4$ and evaporated under vacuum to obtain crude solid. The crude solid was purified by using silica gel column chromatography ($CHCl_3$:MeOH; 90:10) to obtain title compound as white solid compound in 40% (0.230 g) yield. MS: m/z: 829.1 (M+1). Mp: 160-163° C.

Following examples were prepared by using above procedure and by using reagent A.

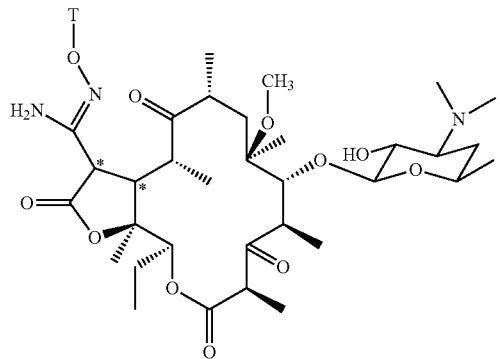

| Example | T | Reagent (A) | Mp (° C.) | Mass (M + 1) |
|---|---|---|---|---|
| 260 | CH$_2$-(5-(pyridin-4-yl)[1,2,4]oxadiazol-3-yl) | 4-(3-chloromethyl-[1,2,4]-oxadiazol-5-yl)-pyridine | 151-155 | 829.1 |
| 261 | CH$_2$-(5-(2-chloro pyridin-3-yl)[1,2,4] oxadiazol-3-yl) | 2-chloro-3-(3-chloromethyl-[1,2,4]-oxadiazol-5-yl)-pyriidne | 148-151 | 863.1 |
| 262 | CH$_2$-(5-(3-fluoro phenyl)[1,2,4] oxadiazol-3-yl) | 3-chloromethyl-5-(3-fluoro-phenyl)-[1,2,4]-oxadiazole | 150-153 | 845.1 |
| 263 | CH$_2$-(5-(3-cyano phenyl)[1,2,4]oxadiazol-3-yl) | 3-(3-chloromethyl-[1,2,4]-oxadiazol-5-yl)-benzonitrile | 184-188 | 852.1 |
| 264 | CH$_2$-(5-(3-chloro phenyl)[1,2,4]oxadi-azol-3-yl) | 3-chloromethyl-5-(3-chlorophenyl)-[1,2,4]-oxadiazole | 133-136 | 861.1 |
| 265 | CH$_2$-(5-(pyridin-2-yl)[1,2,4]oxadiazol-3-yl) | 3-(3-chloromethyl-[1,2,4]-oxadiazol-5-yl)-pyridine | 164-166 | 829.1 |
| 266 | CH$_2$-(5-(2-methoxy pyridin-3-yl)[1,2,4] oxadiazol-3-yl) | 2-methoxy-3-(3-chloromethyl-[1,2,4]-oxadiazol-5-yl)-pyridine | 123-125 | 859.1 |
| 267 | CH$_2$-(5-(3-fluoro-4-methoxyphenyl)[1,2,4] oxadiazol-3-yl) | 3-chloromethyl-5-(3-fluoro-4-methoxy-phenyl)-[1,2,4]-oxadiazole | 161-165 | 875.1 |
| 268 | CH$_2$-5-(2-fluoro pyridin-3-yl)[1,2,4] oxadiazol-3-yl) | 2-fluoro-3-(3-chloromethyl-[1,2,4]-oxadiazol-5-yl)-pyridine | 132-135 | 847.1 |
| 269 | CH$_2$-(5-phenyl[1,2,4] oxadiazol-3-yl) | 3-chloromethyl-5-phenyl-[1,2,4]-oxadiaozle | 189-192 | 827.1 |
| 270 | CH$_2$-(5-methyl[1,2,4] oxadiazol-3-yl) | 3-chloromethyl-5-methyl-[1,2,4]-oxadiazole | 170-173 | 766.1 |
| 271 | CH$_2$-(5-(pyridazin-2-yl)-[1,2,4]oxadiazol-3-yl) | 2-(3-chloromethyl-[1,2,4]-oxadiazol-5-yl)-pyridazine | 145-147 | 831.1 |
| 272 | CH$_2$-(5-trifluoromethyl [1,2,4]oxadiazol-3-yl) | 3-chloromethyl-5-trifluoromethyl-[1,2,4]-oxadiazole | 154-157 | 820.1 |
| 273 | CH$_2$(5-(6-methylpyridin-2-yl)[1,2,4]oxadiazol-3-yl) | 2-(3-chloromethyl-[1,2,4]-oxadiazol-5-yl)-6-methyl-pyridine | 194-197 | 843.1 |
| 274 | CH$_2$-(5-(2-methyl-oxazol-4-yl)-[1,2,4] oxadiazol-3-yl) | 3-chloromethyl-5-(2-methyl-oxazol-4-yl)-[1,2,4]-oxadiazole | 136-140 | 833.1 |
| 275 | CH$_2$-(5-cyclopropyl [1,2,4]oxadiazol-3-yl) | 3-Chloromethyl-5-cyclopropyl-[1,2,4]-oxadiazole | 175-178 | 791.1 |
| 276 | CH$_2$-(5-(5-methyl-pyridin-2-yl)-[1,2,4] oxadiazol-3-yl) | 2-(5-chloro methyl-[1,2,4]-oxadiazol-5-yl)-5-methyl-pyridine | — | 844.1 |
| 277 | CH$_2$-(5-(5-cyclopropyl-pyridin-2-yl)-[1,2,4] oxadiazol-3-yl) | 2-(5-chloromethyl-[1,2,4]-oxadiazol-5-yl)-5-cyclopropyl-pyridine | — | 870.1 |
| 278 | CH$_2$-(5-(5-cyano-pyridin-2-yl)-[1,2,4] oxadiazol-3-yl) | 2-(5-chloromethyl-[1,2,4]-oxadiazol-5-yl)-5-cyano-pyridine | — | 855.1 |

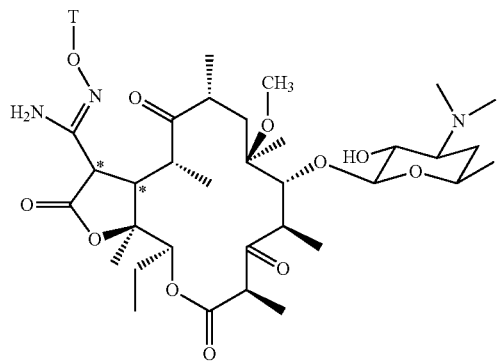

| Example | T | Reagent (A) | Mp (° C.) | Mass (M + 1) |
|---|---|---|---|---|
| 279 | CH$_2$-(5-(5-dimethyl amino-pyridin-2-yl)-[1,2,4]oxadiazol-3-yl) | 2-(5-chloromethyl-[1,2,4]-oxadiazol-5-yl)-5-dimethylamino-pyridine | — | 874.1 |
| 280 | CH$_2$-(5-(5-methoxy-pyridin-2-yl)-[1,2,4]oxadiazol-3-yl) | 2-(5-chloromethyl-[1,2,4]-oxadiazol-5-yl)-5-methoxy-pyridine | — | 860.1 |
| 281 | CH$_2$(5-(5-fluoro-pyridin-2-yl)-[1,2,4]oxadiazol-3-yl) | 2-(5-chloromethyl-[1,2,4]-oxadiazol-5-yl)-5-fluoro-pyridine | — | 848.1 |
| 282 | CH$_2$-(5-(5-chloro-pyridin-2-yl)-[1,2,4]oxadiazol-3-yl) | 2-(5-chloromethyl-[1,2,4]-oxadiazol-5-yl)-5-chloro-pyridine | — | 864.1 |
| 283 | CH$_2$-(5-(pyrimidin-5-yl)-[1,2,4]oxadiazol-3-yl) | 5-(5-chloromethyl-[1,2,4]-oxadiazol-5-yl)-pyrimidine | — | 831.1 |

Example-284

Compound of Formula I-f where T is CH$_2$-(3-(pyridin-2-yl)-isoxazol-5-yl)

Step-1: To the stirred solution of 2-pyridinecarboxaldehyde (2.00 ml, 18.69 mmol) in methanol (20 ml) was added sodium acetate (1.83 g, 22.44 mmol). To this reaction mixture hydroxylamine hydrochloride (1.51, 20.56 mmol) was added and stirred for 2 hour at 20-30° C. temperature. The reaction mixture was evaporated under vacuum to provide a crude mass. To the crude mass was stirred with water (20 ml), to effect precipitation and the separated solid was filtered under suction, dried under vacuum to provide step-1 product in 85% (1.93 g) yield. MS: m/z 123 (M+1).

Step 2: To the stirred solution of step-1 product pyridine-2-carbaldehyde oxime (1.80 g, 14.75 mmol) in DMF (20 ml), was added N-chloro succinimide (2.55 g, 19.19 mmol) and the reaction mixture was stirred for 8 hour at 25-30° C. temperature. Ice-water was added (20 ml) to the reaction mixture to effect precipitation and solid was filtered at suction and dried under vacuum to provide imidoyl chloride as step-2 product imidoyl chloride in 70% (1.61 g) yield. This was used directly for the next reaction. MS: m/z 157 (M+1).

Step-3: To the stirred solution of product obtained from step A of Example 185 (1.5 gm, 1.82 mmol) in toluene (15 ml) was added triethyl amine (0.50 ml, 3.64 mmol). N-hydroxy-pyridine-2-carboximidoyl chloride (0.42 g, 2.73 mmol) was added to the reaction mixture and heated at 90° C. temperature for 12 hr. The reaction mixture was poured in aqueous saturated ammonium chloride solution (20 ml). The mixture was extracted with ethyl acetate (3×25 ml). Combined organic layer was dried over Na$_2$SO$_4$ and purified by using silica gel column chromatography (10% Acetone:Hexane) to provide off white solid as a step-3 product in 78% (1.34 g) yield. MS: m/z: 945 (M+1).

Step-4: To the stirred solution of N-chlorosuccinimide (1.27 g, 9.53 mmol) in dichloromethane (15 ml) at 0° C. was added dimethyl sulfide (1.16 ml, 15.88 mmol). The reaction mixture was stirred at 0° C. for 30 min. The step-3 product (1.2 gm, 1.27 mmol) dissolved in dichloromethane (10 ml) was added to the reaction mixture at −40° C. The resulting reaction mixture was stirred at the same temperature for 2 hr and allowed to warm at 25-30° C. temperature. Triethyl amine (1.76 ml, 12.71 mmol) was added and it was stirred for additional 30 min. The reaction mixture was poured in aqueous saturated sodium bicarbonate solution (100 ml) and the mixture was extracted with dichloromethane (3×25 ml). The combined organic layer was dried over Na$_2$SO$_4$ and purified by using silica gel column chromatography (10% Acetone:Hexane) to provide step-4 product as a off white solid in 75% (0.9 g) yield. MS: m/z: 943 (M+1).

Step-5: The mixture of step-4 product (0.9 g, 0.90 mmol) and 70% HF-Pyridine solution (41 µl, 1.43 mmol) dissolved in acetonitrile (10 ml) was stirred at 25-30° C. for 2 hr under N$_2$ atmosphere. After completion of reaction, solvent was evaporated under vacuum to obtain crude product. Water (20 ml) was added to the crude product and extracted with dichloromethane (3×25 ml). Combined organic layer was dried over sodium sulphate and evaporated under vacuum to obtain crude mass. The crude mass was purified by using silica gel column chromatography (10% MeOH:CHCl$_3$) to obtain title compound in 50% (0.39 g) yield. Mp: 198-201° C., MS: m/z: 829 (M+1).

Following examples were prepared by using above procedure and by using reagent A.

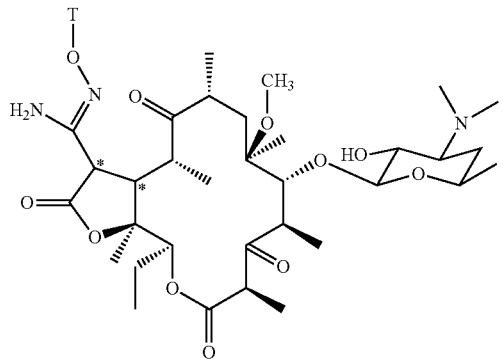

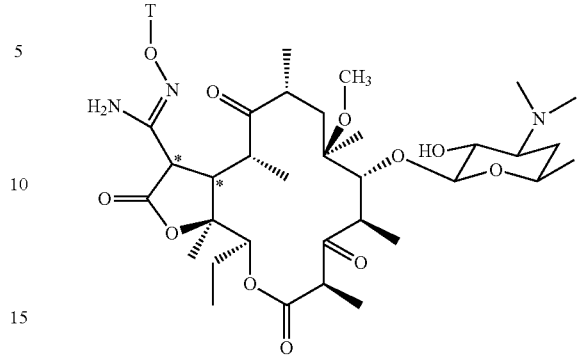

| Example | T | Reagent (A) | Mp (° C.) | Mass (M + 1) |
|---|---|---|---|---|
| 285 | $CH_2$-(3-(pyridin-3-yl)-isoxazol-5-yl) | N-hydroyxpyridine-3-carboximidoyl chloride | 172-174 | 828.1 |
| 286 | $CH_2$-(3-(3-fluoro phenyl)-isoxazol-5-yl) | 3-fluoro-N-hydroxy benzene-carboximidoyl chloride | 146-148 | 845.1 |
| 287 | $CH_2$-(3-(3-chloro phenyl)-isoxazol-5-yl) | 3-chloro-N-hydroxy benzene-carboximidoyl choride | 176-180 | 861.1 |
| 288 | $CH_2$-(3-(4-fluoro-phenyl)-isoxazol-5-yl) | 4-fluoro-N-hydroxy benzene-carboximidoyl chloride | 212-214 | 845.1 |
| 289 | $CH_2$-(3-(3-methoxy phenyl)-isoxazol-5-yl) | N-hydroxy-3-methoxy-benzene-carboximidoyl chloride | 217-221 | 857.1 |
| 290 | $CH_2$-(3-phenyl-isoxazol-5-yl) | N-hydroxybenzene-carboximidoyl chloride | 223-225 | 827.1 |
| 291 | $CH_2$-(3-methyl-isoxazol-5-yl) | (1Z)-N-hydroxy ethanimidoyl chloride | 185-189 | 765.1 |
| 292 | $CH_2$-(3-(6-methoxy-pyridin-2-yl)-isoxazol-5-yl) | N-hydroxy-6-methoxypyridine-2-carboximidoyl chloride | 180-182 | 858.1 |
| 293 | $CH_2$-(3-(2-methoxy-pyridin-5-yl)-isoxazol-5-yl) | N-hydroxy-6-methoxypyridine-3-carboximidoyl chloride | 184-186 | 858.1 |
| 294 | $CH_2$-(3-(5-methyl-pyridin-2-yl)-isoxazol-5-yl) | N-hydroxy-5-methyl pyridine-2-carboximidoyl chloride | — | 843.1 |
| 295 | $CH_2$-(3-(5-cyclo-propyl-pyridin-2-yl)-isoxazol-5-yl) | 5-cyclopropyl-N-hydroxy-pyridine-2-carboximidoyl chloride | — | 869.1 |
| 296 | $CH_2$-(3-(5-cyano-pyridin-2-yl)-isoxazol-5-yl) | 5-cyano-N-hydroxy-pyridine-2-carboximidoyl chloride | — | 854.1 |
| 297 | $CH_2$-(3-(5-dimethyl amino-pyridin-2-yl)-isoxazol-5-yl) | 5-(dimethylamino)-N-hydroxy-pyridine-2-carboximidoyl chloride | — | 873.1 |
| 298 | $CH_2$-(3-(5-methoxy-pyridin-2-yl)-isoxazol-5-yl) | N-hydroxy-5-methoxypyridine-2-carboximidoyl chloride | — | 859.1 |
| 299 | $CH_2$-(3-(5-fluoro-pyridin-2-yl)-isoxazol-5-yl) | 5-fluoro-N-hydroxy-pyridine-2-carboximidoyl chloride | — | 847.1 |
| 300 | $CH_2$-(3-(5-chloro-pyridin-2-yl)-isoxazol-5-yl) | 5-chloro-N-hydroxy-pyridine-2-carboximidoyl chloride | — | 863.1 |
| 301 | $CH_2$-(3-(pyrimidin-5-yl)-isoxazol-5-yl) | N-hydroxy-pyrimidine-5-carboximidoyl chloride | — | 830.1 |

Example-302

Compound of Formula I-f where T is $CH_2$-(5-(pyridin-3-yl)-isoxazol-3-yl)

Step A: To the stirred solution of Example 7 (1.0 g, 1.3 mmol) in toluene (15 ml) is added potassium tert-butoxide (0.16 g, 1.43 mmol) and 18-crown-6-ether (0.048 g, 0.13 mmol) at 25-30° C. temperature. The reaction mixture is stirred for 10 min at 25-30° C. temperature. 2-(3-Chloromethyl-isoxazol-5-yl)-pyridine (0.28 mol, 1.43 mmol) is added to the reaction mixture and it is stirred for additional 1 hour. It is quenched by pouring it in aqueous saturated ammonium chloride solution (20 ml). The mixture is extracted with ethyl acetate (3×25 ml). Combined organic layer is dried over $Na_2SO_4$ and purified by using silica gel column chromatography (10% Acetone:Hexane) to provide step-1 product as a pale yellow solid in 48% (0.57 g) yield. MS: m/z: 945.1 (M+1).

Step B: To the stirred solution of N-chlorosuccinimide (0.6 g, 4.5 mmol) in dichloromethane (15 ml) at 0° C. is added dimethyl sulfide (0.48 ml, 7.5 mmol). The reaction mixture is stirred at 0° C. for 30 min. The step-1 product (0.55 gm, 0.6 mmol) dissolved in dichloromethane (10 ml) is added to the reaction mixture at −40° C. The resulting reaction mixture is stirred at the same temperature for 2 hr and allowed to warm at 25-30° C. temperature. Triethyl amine (0.84 ml, 6.0 mmol) is added and it is stirred for additional 30 min. The reaction mixture is poured in aqueous saturated sodium bicarbonate solution (100 ml) and the mixture is extracted with dichloromethane (3×25 ml). The combined organic layer is dried over $Na_2SO_4$ and purified by using silica gel column chromatography (10% Acetone:Hexane) to provide step-4 product as a off white solid in 72% (0.4 g) yield. MS: m/z: 943 (M+1).

Step C: The mixture of step-4 product (0.4 g, 0.42 mmol) and 70% HF-Pyridine solution (18 μl, 0.64 mmol) dissolved in acetonitrile (10 ml) is stirred at 25-30° C. for 2 hr under $N_2$ atmosphere. After completion of reaction, solvent is evaporated under vacuum to obtain crude product. Water (20 ml) is added to the crude product and extracted with dichloromethane (3×25 ml). Combined organic layer is dried over sodium sulphate and evaporated under vacuum to obtain crude mass. The crude mass is purified by using silica gel column chromatography (10% MeOH:$CHCl_3$) to obtain title compound in 65% (0.25 g) yield. MS: m/z: 829 (M+1).

Following examples are prepared by using above procedure and by using reagent A.

| | | | | |
|---|---|---|---|---|
| Example | T | Reagent (A) | Mp (° C.) | Mass (M + 1) |
| | | 5-carboximidoyl chloride | | |

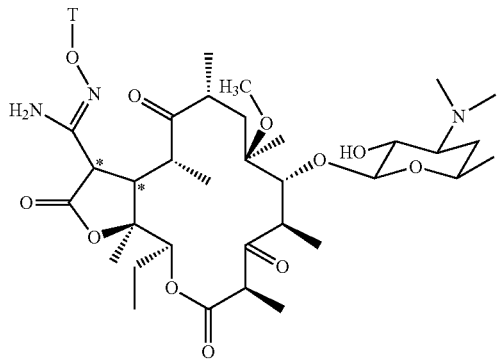
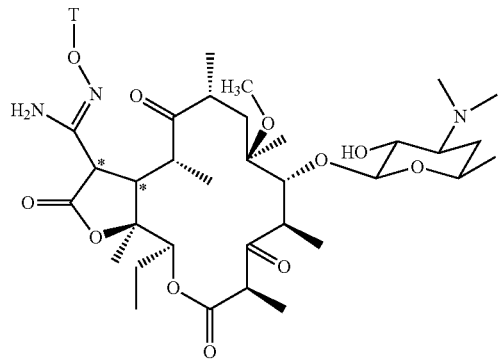

| Example | T | Reagent A | Mass (M + 1) |
|---|---|---|---|
| 303 | $CH_2$-(5-(3-fluorophenyl)-isoxazol-3-yl) | 3-chloromethyl-5-(3-fluoro-phenyl)-isoxazole | 845.1 |
| 304 | $CH_2$-(5-(3-chlorophenyl)-isoxazol-3-yl) | 3-chloromethyl-5-(3-chloro-phenyl)-isoxazole | 861.1 |
| 305 | $CH_2$-(5-(4-fluorophenyl)-isoxazol-3-yl) | 3-chloromethyl-5-(4-fluoro-phenyl)-isoxazole | 845.1 |
| 306 | $CH_2$-(5-(3-methoxy phenyl)-isoxazol-3-yl) | 3-chloromethyl-5-(3-methoxy-phenyl)-isoxazole | 857.1 |
| 307 | $CH_2$-(5-phenyl)-isoxazol-3-yl) | 3-chloromethyl-5-phenyl-isoxazole | 827.1 |
| 308 | $CH_2$-(5-methyl)-isoxazol-3-yl) | 3-chloromethyl-5-methyl-isoxazole | 765.1 |
| 309 | $CH_2$-(5-(6-methoxy-pyridin-2-yl)-isoxazol-3-yl) | 2-(3-chloromethyl-isoxazol-5-yl)-6-methoxy-pyridine | 858.1 |
| 310 | $CH_2$-(5-(2-methoxy-pyridin-5-yl)-isoxazol-3-yl) | 5-(3-chloromethyl-isoxazol-5-yl)-2-methoxy-pyridine | 858.1 |
| 311 | $CH_2$-(5-(5-methyl-pyridin-2-yl)-isoxazol-3-yl) | 2-(3-chloromethyl-isoxazol-5-yl)-5-methyl-pyridine | 843.1 |
| 312 | $CH_2$-(5-(5-cyclopropyl-pyridin-2-yl)-isoxazol-3-yl) | 2-(3-chloromethyl-isoxazol-5-yl)-5-cyclopropyl-pyridine | 869.1 |
| 313 | $CH_2$-(5-(5-cyano-pyridin-2-yl)-isoxazol-3-yl) | 2-(3-chloromethyl-isoxazol-5-yl)-5-cyano-pyridine | 854.1 |
| 314 | $CH_2$-(5-(5-dimethylamino-pyridin-2-yl)-isoxazol-3-yl) | 2-(3-chloromethyl-isoxazol-5-yl)-5-dimethylamino-pyridine | 873.1 |
| 315 | $CH_2$-(5-(5-methoxy-pyridin-2-yl)-isoxazol-3-yl) | 2-(3-chloromethyl-isoxazol-5-yl)-5-methoxy-pyridine | 859.1 |
| 316 | $CH_2$-(5-(5-fluoro-pyridin-2-yl)-isoxazol-3-yl) | 2-(3-chloromethyl-isoxadiazol-5-yl)-5-fluoro-pyridine | 847.1 |
| 317 | $CH_2$-(5-(5-chloro-pyridin-2-yl)-isoxazol-3-yl) | 2-(3-chloromethyl-isoxazol-5-yl)-5-chloro-pyridine | 863.1 |
| 318 | $CH_2$-(pyrimidin-5-yl)-isoxazol-3-yl) | 5-(3-chloromethyl-isoxazol-5-yl)-pyrimidine | 830.1 |
| 319 | $CH_2CH_2$-(4-(pyridin-2-yl)-1H-imidazol-1-yl) | 2-[1-(2-Chloro-ethyl)-1H-imidazol-4-yl]-pyridine | 842.1 |
| 320 | $CH_2CH_2$-(4-(pyridin-3-yl)-1H-imidazol-1-yl) | 3-[1-(2-Chloro-ethyl)-1H-imidazol-4-yl]-pyridine | 842.1 |
| 321 | $CH_2CH_2$-(4-(6-methyl-pyridin-2-yl)-1H-imidazol-1-yl) | 2-[1-(2-Chloro-ethyl)-1H-imidazol-4-yl]-6-methyl-pyridine | 856.1 |
| 322 | $CH_2CH_2$-(4-(4-methoxy-pyridin-2-yl)-1H-imidazol-1-yl) | 2-[1-(2-Chloro-ethyl)-1H-imidazol-4-yl]-4-methoxy-pyridine | 872.1 |
| 323 | $CH_2$-(4-(pyridin-2-yl)-pyrazol-4-yl) | 2-(4-Chloromethyl-pyrazol-1-yl)-pyridine | 828.1 |
| 324 | $CH_2$-(4-(pyridin-3-yl)-pyrazol-4-yl) | 3-(4-Chloromethyl-pyrazol-1-yl)-pyridine | 828.1 |
| 325 | $CH_2$-(4-(6-methyl-pyridin-2-yl)-pyrazol-4-yl) | 2-(4-Chloromethyl-pyrazol-1-yl)-6-methyl-pyridine | 842.1 |
| 326 | $CH_2$-(4-(4-methoxy-pyridin-2-yl)-pyrazol-4-yl) | 2-(4-Chloromethyl-pyrazol-1-yl)-4-methoxy-pyridine | 858.1 |
| 327 | $CH_2$-(4-(5-methoxy-pyridin-2-yl)-pyrazol-4-yl) | 2-(4-Chloromethyl-pyrazol-1-yl)-5-methoxy-pyridine | 858.1 |
| 328 | $CH_2$-(1-(pyridin-2-yl)-1H-imidazol-4-yl) | 2-(4-Chloromethyl-imidazol-1-yl)-pyridine | 828.1 |
| 329 | $CH_2$-(1-(pyridin-3-yl)-1H-imidazol-4-yl) | 3-(4-Chloromethyl-imidazol-1-yl)-pyridine | 828.1 |
| 330 | $CH_2$-(1-(6-methyl-pyridin-2-yl)-1H-imidazol-4-yl) | 2-(4-Chloromethyl-imidazol-1-yl)-6-methyl-pyridine | 842.1 |
| 331 | $CH_2$-(1-(4-methoxy-pyridin-2-yl)-1H-imidazol-4-yl) | 2-(4-Chloromethyl-imidazol-1-yl)-4-methoxy-pyridine | 858.1 |
| 332 | $CH_2$-(1-(5-methoxy-pyridin-2-yl)-1H-imidazol-4-yl) | 2-(4-Chloromethyl-imidazol-1-yl)-5methoxy-pyridine | 858.1 |
| 333 | $CH_2$-(2-(pyridin-2-yl)-oxazol-4-yl) | 2-(4-Chloromethyl-oxazol-2-yl)-pyridine | 829.1 |
| 334 | $CH_2$-(2-(pyridin-3-yl)-oxazol-4-yl) | 3-(4-Chloromethyl-oxazol-2-yl)-pyridine | 829.1 |
| 335 | $CH_2$-(2-(6-methyl-pyridin-2-yl)-oxazol-4-yl) | 2-(4-Chloromethyl-oxazol-2-yl)-6-methyl-pyridine | 843.1 |
| 336 | $CH_2$-(2-(4-methoxy-pyridin-2-yl)-oxazol-4-yl) | 2-(4-Chloromethyl-oxazol-2-yl)-4-methoxy-pyridine | 859.1 |
| 337 | $CH_2$-(2-(5-methoxy-pyridin-2-yl)-oxazol-4-yl) | 2-(4-Chloromethyl-oxazol-2-yl)-5-methoxy-pyridine | 859.1 |

Example-338

Compound of Formula I-f where Q is CN

A mixture of Example 8 (0.95 g, 1.3 mmol) and 70% hydrogen fluoride in pyridine (50 μl, 1.8 mmol) in acetonitrile (15 ml) was stirred under inert atmosphere at a temperature between 25-30° C. for 3 h. The solvent was evaporated under vacuum and the residue obtained was dissolved in ethyl acetate (25 ml) and washed with water (2×10 ml). The combined organic layer was dried over $Na_2SO_4$ and evaporated under reduced pressure to provide crude solid which on trituration in diethyl ether afforded pale yellow solid as the title compound in 60% (0.58 g) yield. MP: 230-232° C., Mass: m/z: 638.1 (M+1).

Example-339

Compound of Formula I-f where T is H

A mixture of Example 9 (0.95 g, 1.2 mmol) and 70% hydrogen fluoride in pyridine (50 μl, 1.8 mmol) in acetonitrile (15 ml) was stirred under inert atmosphere at a temperature between 25-30° C. for 15 h. The solvent was evaporated under vacuum and the residue obtained was dissolved in ethyl acetate (25 ml) and washed with water (2×10 ml). The combined organic layer was dried over $Na_2SO_4$ and evaporated under reduced pressure to provide crude solid which on trituration in diethyl ether afforded pale yellow solid as the title compound in 75% (0.7 g) yield. MP: 174-176° C., Mass: m/z: 671.1 (M+1).

Example-340

Compound of Formula I-f where T is $(CH_2)_2CH_3$

To a stirring solution of Example 179 (0.3 gm, 0.37 mm) in THF (10 ml) was added 10% Pd/C (30 mg, 10%) and stirred under $H_2$ atmosphere for 15 hr. The reaction mixture was filtered through celite and concentrated under reduced pressure. Crude solid was triturated in diethyl ether affording white solid. Yield: 250 mg (84%), MP: 182-184° C., Mass: m/z: 713.1 (M+H).

Following examples were prepared as per the procedure mentioned above by using the corresponding unsaturated starting material.

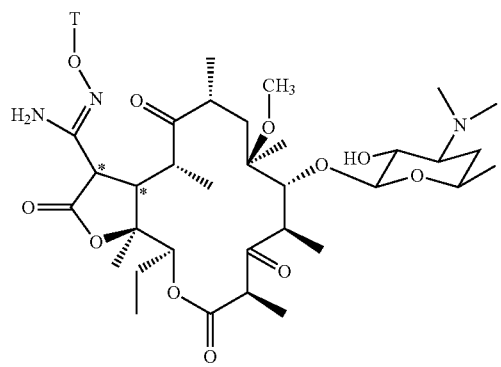

| Example | Starting material | T | Mp (° C.) | Mass (M + 1) |
|---|---|---|---|---|
| 341 | Example 205 | $CH_2CH_2CH(CH_3)_2$ | 244-246 | 741.1 |
| 342 | Example 208 | $CH_2(CH_2)_2Ph$ | 172-174 | 789.1 |

While the present invention has been described in terms of its specific embodiments, certain modifications and equivalents will be apparent to those skilled in the art and are intended to be included within the scope of the present invention.

The invention claimed is:

1. Compounds having the structure of Formula I:

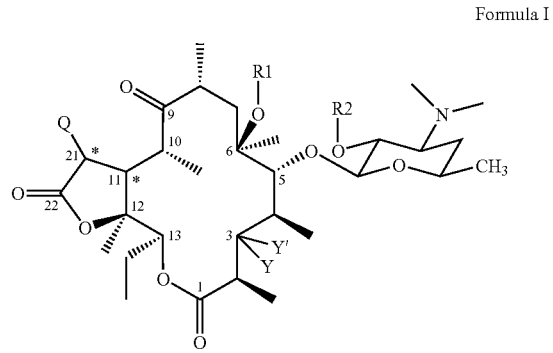

Formula I and their pharmaceutically acceptable salts, pharmaceutically acceptable enantiomers or diastereomers, wherein

* indicates a chiral center;

$R_1$ is hydrogen or methyl;

$R_2$ is hydrogen or hydroxyl protecting group,
  wherein hydroxyl protecting groups are selected from the group consisting of triethylsilyl, trimethylsilyl, acetyl, benzoyl, methoxymethyl, benzyl, methoxyethoxymethyl or tertbutyldimethylsilyl;

Q is Het or

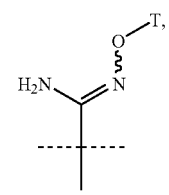

wherein
Het is selected from

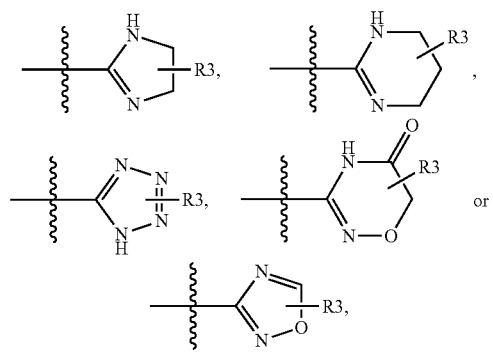

wherein $R_3$ is one or more substituent selected from the group consisting of $NO_2$, CN, halogen, $C_1$-$C_6$ alkyl, $C_2$-$C_6$ alkenyl, $CH_2CONH_2$, $CH_2CO_2Et$, $CH_2CN$, $CH_2CH_2OH$, $CH_2OCH_2CH_2OCH_3$, $NH_2$, substituted $C_1$-$C_6$ alkyl and substituted $C_2$-$C_6$ alkenyl;

T is selected from the group consisting of:
hydrogen, —$(CH_2)_m$—$R_5$, —$(CH_2)_m$—CH=CH—$R_5$, —$(CH_2)_m$—C≡C—$R_5$, $(CH_2)_m$—$R_5$, -A-$(CH_2)_m$—

CH=CH—R$_5$, -A-(CH$_2$)$_m$—C≡C—R$_5$, —(CH$_2$)$_m$—B—R$_5$, (CH$_2$)$_m$—B—R$_5$, —(CH$_2$)$_m$—X—R$_6$, —(CH$_2$)$_m$—B-X—R$_6$, —(CH$_2$)$_m$—CH=CH—X—R$_6$, —(CH$_2$)$_m$—C≡C—X—R$_6$, -A-(CH$_2$)$_m$—X—R$_6$, -A-(CH$_2$)$_m$—B—X—R$_6$, -A-(CH$_2$)$_m$—CH=CH—X—R$_6$ and -A-(CH$_2$)$_m$—C≡C—X—R$_6$;

wherein, m is 0, 1, 2 or 3;

R$_5$ is selected from the group consisting of:
hydrogen, cyano, halogen, hydroxyl, CO$_2$(C$_1$-C$_6$ alkyl), CO NR$_a$R$_b$,
NR$_a$R$_b$, C$_1$-C$_6$ alkyl or substituted C$_1$-C$_6$ alkyl, C$_2$-C$_6$ alkenyl or substituted C$_2$-C$_6$ alkenyl, C$_2$-C$_6$ alkynyl or substituted C$_2$-C$_6$ alkynyl, 6 membered substituted or unsubstituted aryl, 5-6 membered substituted or unsubstituted heteroaryl, 3-6 membered substituted or unsubstituted cycloalkyl and 3-6 membered substituted or unsubstituted heterocyclyl;
wherein R$_a$ and R$_b$ are independently hydrogen, C$_1$-C$_6$ alkyl or
R$_a$ and R$_b$ together with the nitrogen to which they are attached form a 5-6 membered heterocyclic ring wherein the heterocycle has one or more heteroatoms selected from N, O, S;

A is —CO— or —CONH—;

B is —O—, —S—, —SO—, —SO$_2$—, —CO—, —CONH—, —CON(CH$_3$)—, —NHCONH—, —C(NH$_2$)=N—O—,

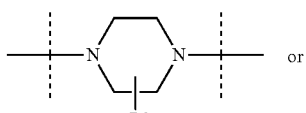

or

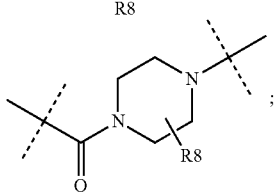

wherein

R$_8$ is a substitutent at any one of carbon of the heterocycle,

R$_8$ is selected from the group comprising of hydrogen, C$_1$-C$_6$ alkyl, substituted C$_1$-C$_6$ alkyl, C$_2$-C$_6$ alkenyl and substituted C$_2$-C$_6$ alkenyl;

X is a 6 membered aryl or a 5-6 membered heteroaryl;

R$_6$ is aryl, heteroaryl, substituted aryl or substituted heteroaryl;

Y' is hydrogen and Y is OR$_7$, wherein R$_7$ is hydrogen or

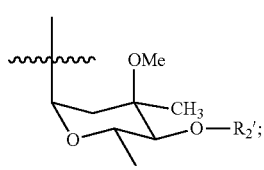

wherein R$_{2'}$ is hydrogen, (when R$_{2'}$ is hydrogen, R$_7$ is designated as cladinose) or hydroxyl protecting group, wherein hydroxyl protecting groups are selected from the group consisting of triethylsilyl, trimethylsilyl, acetyl, benzoyl, methoxymethyl, methoxyethoxymethyl, benzyl or tertbutyldimethylsilyl; or Y and Y' together with the carbon to which they are attached form C=O.

2. The compound of claim 1, wherein R$_1$ is CH$_3$ and Het is

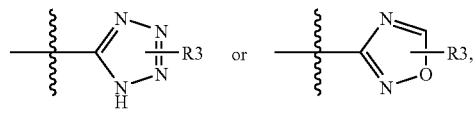

wherein R$_3$ is one or more substituent selected from C$_1$-C$_6$ alkyl, C$_2$-C$_6$ alkenyl, CH$_2$CONH$_2$, CH$_2$CO$_2$(C$_1$-C$_6$ alkyl), CH$_2$CN, CH$_2$CH$_2$OH, CH$_2$OCH$_2$CH$_2$OCH$_3$.

3. The compound of claim 1, wherein Q is

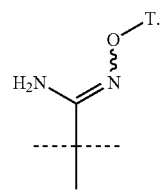

4. The compound of claim 3, wherein T is selected from
—(CH$_2$)$_m$—R$_5$, —(CH$_2$)$_m$—C≡C—R$_5$, —(CH$_2$)$_m$—C=C—R$_5$, -A-(CH$_2$)$_m$—R$_5$, -A-(CH$_2$)$_m$—CH=CH—R$_5$, -A-(CH$_2$)$_m$—C≡C—R$_5$, —(CH$_2$)$_m$—B—R$_5$, -A-(CH$_2$)$_m$—B—R$_5$, wherein m is 1 or 2; A is —CO—; B is piperazinyl;

R$_5$ is substituted/unsubstituted phenyl or heteroaryl;
wherein heteroaryl is selected from pyridin-4-yl, pyridin-3-yl, pyridin-2-yl, pyrimidinyl, pyrazzolyl, imidazolyl, triazolyl, tetrazolyl, oxadiazolyl, oxazolyl or isoxazolyl;

phenyl or heteroaryl may be substituted with one or more substituents selected from the group comprising of C$_1$-C$_6$ alkyl, C$_1$-C$_6$ alkoxy, cyano, halogen, dimethylamino.

5. The compound of claim 1, wherein T is selected from
—(CH$_2$)$_m$—X—R$_6$, —(CH$_2$)$_m$—CH=CH—X—R$_6$, —(CH$_2$)$_m$—C≡C—X—R$_6$, -A-(CH$_2$)$_m$—X—R$_6$, -A-(CH$_2$)$_m$—CH=CH—X—R$_6$, -A-(CH$_2$)$_m$—C≡C—X—R$_6$.

6. The compound of claim 5, wherein X—R$_6$ is

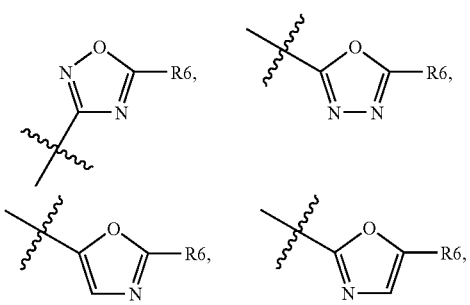

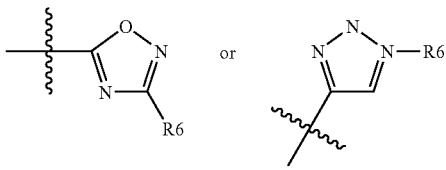

wherein R₆ is phenyl, substituted phenyl, heteroaryl or substituted heteroaryl; wherein heteroaryl is selected from one or more of pyridin-4-yl, pyridin-3-yl, pyridin-2-yl, pyrimidinyl, pyrazzolyl, imidazolyl, triazolyl, tetrazolyl, oxadiazolyl, oxazolyl or isoxazolyl; wherein the phenyl or heteroaryl is substituted with one or more substituents selected from the group comprising of $C_1$-$C_6$ alkyl, $C_1$-$C_6$ alkoxy, cyano, halogen and dimethylamino.

7. The compound of claim 1, wherein T is —(CH₂)ₘ—X—R₆, wherein R₆.

8. The compound of claim 7, wherein X—R₆ is

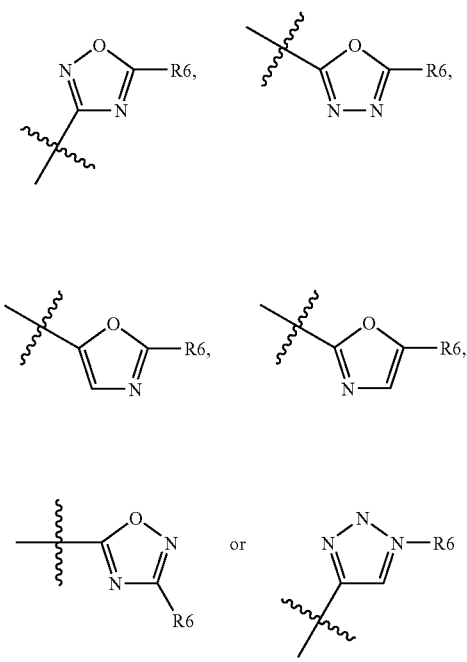

wherein R₆ is phenyl, substituted phenyl, heteroaryl or substituted heteroaryl.

9. The compound of claim 8, wherein heteroaryl is pyridin-4-yl, pyridin-3-yl, pyridin-2-yl, pyrimidinyl, pyrazzolyl, imidazolyl, triazolyl, tetrazolyl, oxadiazolyl, oxazolyl or isoxazolyl.

10. The compound of claim 8, wherein the phenyl or heteroaryl is substituted with one or more substituents selected from the group comprising of $C_1$-$C_6$ alkyl, $C_1$-$C_6$ alkoxy, cyano, halogen, dimethylamino.

11. A compound of Formula I-c, wherein the compound is selected from the group consisting of:

Formula I-c

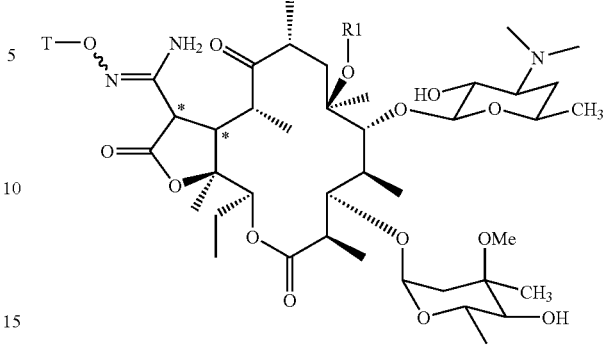

Compound of Formula I-c, where T is CH₂CH₂-(1-(3-methoxy)phenyl-1H-[1,2,3]triazol-4-yl), R₁ is CH₃;
Compound of Formula I-c, where T is COCH=CH-(pyridin-4-yl), R₁ is CH₃;
Compound of Formula I-c, where T is COCH=CH-(pyridin-3-yl), R₁ is CH₃;
Compound of Formula I-c, where T is CO(CH₂)₂-(pyridin-3-yl), R₁ is CH₃;
Compound of Formula I-c, where T is CO(CH₂)₂-(3-methoxy)phenyl, R₁ is CH₃;
Compound of Formula I-c, where T is CO(CH₂)₂-(4-methoxy)phenyl, R₁ is CH₃;
Compound of Formula I-c, where T is CO(CH₂)₂-(4-dimethylamino)phenyl, R₁ is CH₃;
Compound of Formula I-c, where T is CO(CH₂)₂-(3-cyano)phenyl, R₁ is CH₃;
Compound of Formula I-c, where T is COCH₂O-(3-chloro)phenyl, R₁ is CH₃;
Compound of Formula I-c, where T is CO(CH₂)₂-(3,5-dimethoxy)phenyl, R₁ is CH₃;
Compound of Formula I-c, where T is CO(CH₂)₂-(2,3-dimethoxy)phenyl, R₁ is CH₃;
Compound of Formula I-c, where T is CO(CH₂)₂-(3-fluoro)phenyl, R₁ is CH₃;
Compound of Formula I-c, where T is CO(CH₂)₂-(4-(2-methylphenyl)-piperazinyl), R₁ is CH₃;
Compound of Formula I-c, where T is CO(CH₂)₂-(4-(phenyl)piperazinyl), R₁ is CH₃;
Compound of Formula I-c, where T is CO(CH₂)₂-(1-(4-methoxyphenyl)-1H-[1,2,3]triazol-4-yl), R₁ is CH₃;
Compound of Formula I-c, where T is CO(CH₂)₂-(1-(pyridin-3-yl)-[1,2,3]triazol-4-yl), R₁ is CH₃;
Compound of Formula I-c, where T is CO(CH₂)₂-(1-(4-fluorophenyl)-1H-[1,2,3]triazol-4-yl), R₁ is CH₃;
Compound of Formula I-c, where T is CO(CH₂)₂-(1-(3-methylphenyl)-1H-[1,2,3]triazol-4-yl), R₁ is CH₃;
Compound of Formula I-c, where T is CO(CH₂)₂-(1-(3-chlorophenyl)-1H-[1,2,3]triazol-4-yl), R₁ is CH₃;
Compound of Formula I-c, where T is CO(CH₂)₂-(3-(3-bromophenyl)-[1,2,4]oxadiazol-5-yl), R₁ is CH₃;
Compound of Formula I-c, where T is CO(CH₂)₂-(3-(3-fluorophenyl)-[1,2,4]oxadiazol-5-yl), R₁ is CH₃;
Compound of Formula I-c, where T is CO(CH₂)₂-(3-(pyridin-4-yl)-[1,2,4]oxadiazol-5-yl), R₁ is CH₃;
Compound of Formula I-c, where T is CO(CH₂)₂-(3-(pyridin-3-yl)-[1,2,4]oxadiazol-5-yl), R₁ is CH₃;
Compound of Formula I-c, where T is CO(CH₂)₂-[3-(4-methoxyphenyl)-[1,2,4]oxadiazol-5-yl], R₁ is CH₃;
Compound of Formula I-c, where T is CO(CH₂)₂-(1-(2-methoxy)phenyl)-1H-[1,2,3]triazol-4-yl), R₁ is CH₃;

Compound of Formula I-c, where T is CO(CH$_2$)$_2$-(1-(3-fluorophenyl)-1H-[1,2,3]triazol-4-yl), R$_1$ is CH$_3$;

Compound of Formula I-c, where T is CO(CH$_2$)$_2$-(3-phenyl-[1,2,4]oxadiazol-5-yl), R$_1$ is CH$_3$;

Compound of Formula I-c, where T is CO(CH$_2$)$_2$-(3-naphthalen-2-yl-[1,2,4]oxadiazol-5-yl), R$_1$ is CH$_3$ and Compound of Formula I-c, where T is CO(CH$_2$)$_2$-(1-(3,5-difluoro-phenyl)-1H-[1,2,3]triazol-4-yl), R$_1$ is CH$_3$.

12. A compound of Formula I-f, wherein the compound is selected from the group consisting of:

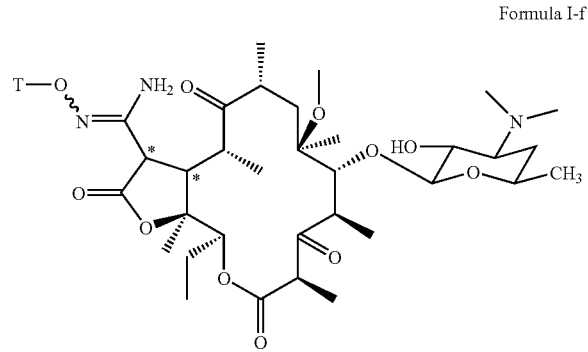

Formula I-f

Compound of Formula I-f, where T is CH$_2$C(F)=CH$_2$;
Compound of Formula I-f, where T is CH$_2$CH=C-(2-fluoropyridin-5-yl);
Compound of Formula I-f, where T is CH$_2$CH=C-(pyridin-3-yl);
Compound of Formula I-f, where T is CH$_2$-(3-chlorophenyl);
Compound of Formula I-f, where T is CH$_2$-(2-fluorophenyl);
Compound of Formula I-f, where T is CH$_2$-(4-(1H-[1,2,4]-triazol)phenyl);
Compound of Formula I-f, where T is CH$_2$-(5-phenyl[1,3,4]oxadiazol-2-yl);
Compound of Formula I-f, where T is CH$_2$-(5-(pyridin-3-yl)[1,3,4]oxadiazol-2-yl);
Compound of Formula I-f, where T is CH$_2$-(5-(3-fluorophenyl)[1,3,4]oxadiazol-2-yl);
Compound of Formula I-f, where T is CH$_2$-(5-(pyridin-2-yl)[1,3,4]oxadiazol-2-yl);
Compound of Formula I-f, where T is CH$_2$-(3-phenyl[1,2,4]oxadiazol-5-yl);
Compound of Formula I-f, where T is CH$_2$-(3-(3-fluorophenyl)[1,2,4]oxadiazol-5-yl);
Compound of Formula I-f, where T is CH$_2$-(3-(3-chlorophenyl)[1,2,4]oxadiazol-5-yl);
Compound of Formula I-f, where T is CH$_2$-(3-(4-chlorophenyl)[1,2,4]oxadiazol-5-yl);
Compound of Formula I-f, where T is CH$_2$-(3-(4-methoxyphenyl)[1,2,4]oxadiazol-5-yl);
Compound of Formula I-f, where T is CH$_2$-(3-(pyridin-3-yl)[1,2,4]oxadiazol-5-yl);
Compound of Formula I-f, where T is CH$_2$-(3-(pyridin-2-yl)[1,2,4]oxadiazol-5-yl);
Compound of Formula I-f, where T is CH$_2$-(3-cyclopropyl[1,2,4]oxadiazol-5-yl);
Compound of Formula I-f, where T is CH$_2$-(5-phenyl[1,2,4]oxadiazol-3-yl);
Compound of Formula I-f, where T is CH$_2$-(5-(pyridin-2-yl)[1,2,4]oxadiazol-3-yl);
Compound of Formula I-f, where T is CH$_2$-(5-(2-fluoropyridin-3-yl)[1,2,4]oxadiazol-3-yl);
Compound of Formula I-f, where T is CH$_2$-(5-cyclopropyl[1,2,4]oxadiazol-3-yl);
Compound of Formula I-f, where T is CH$_2$-(5-methyl[1,2,4]oxadiazol-3-yl);
Compound of Formula I-f, where T is CH$_2$-(5-(pyridazin-2-yl)[1,2,4]oxadiazol-3-yl);
Compound of Formula I-f, where T is CH$_2$-(5-(2-methylthiazol-4-yl)[1,2,4]oxadiazol-3-yl);
Compound of Formula I-f, where T is CH$_2$-(3-(3-fluorophenyl)-isoxazol-5-yl);
Compound of Formula I-f, where T is CH$_2$-(3-(3-chlorophenyl)-isoxazol-5-yl);
Compound of Formula I-f, where T is CH$_2$-(3-(4-fluorophenyl)-isoxazol-5-yl);
Compound of Formula I-f, where T is CH$_2$-(3-(pyridin-2-yl)-isoxazol-5-yl);
Compound of Formula I-f, where T is CH$_2$-(3-phenyl-isoxazol-5-yl);
Compound of Formula I-f, where T is CH$_2$-(3-(5-methyl-pyridin-2-yl)-isoxazol-5-yl);
Compound of Formula I-f, where T is CH$_2$-(3-(5-cyclopropyl-pyridin-2-yl)-isoxazol-5-yl);
Compound of Formula I-f, where T is CH$_2$-(3-(5-cyano-pyridin-2-yl)-isoxazol-5-yl);
Compound of Formula I-f, where T is CH$_2$-(3-(5-dimethylamino-pyridin-2-yl)-isoxazol-5-yl);
Compound of Formula I-f, where T is CH$_2$-(3-(5-methoxy-pyridin-2-yl)-isoxazol-5-yl);
Compound of Formula I-f, where T is CH$_2$-(3-(5-fluoro-pyridin-2-yl)-isoxazol-5-yl);
Compound of Formula I-f, where T is CH$_2$-(3-(5-chloro-pyridin-2-yl)-isoxazol-5-yl) and
Compound of Formula I-f where T is CH$_2$-(3-(pyrimidin-5-yl)-isoxazol-5-yl).

13. A pharmaceutical composition comprising a therapeutically effective amount of a compound as defined in claim 1, optionally together with one or more pharmaceutically acceptable carriers, excipients or diluents.

14. A method for treating bacterial or portozoa infections in a human or an animal, comprising administering to said animal or human, a therapeutically effective amount of a compound of claim 1.

15. The method for treating bacterial or protozoa infections in an animal or a human comprising administering to said animal or human, a pharmaceutical composition according to claims 13.

16. A process for preparing a compound of Formula I as defined in claim 1 or its pharmaceutically acceptable salts, pharmaceutically acceptable enantiomers or diastereomers, the process comprising one or more of the following steps of:

a) treating the compound of Formula VIIa or VIIb with a suitable carboxylic acid reagent of the Formula R$_9$—COOH, wherein R$_9$ represents —(CH$_2$)$_m$—R$_5$, —(CH$_2$)$_m$—CH=CH—R$_5$, —(CH$_2$)$_m$—C=C—R$_5$, —(CH$_2$)$_m$—B—R$_5$, —(CH$_2$)$_m$—CH=CH—R$_5$, —(CH$_2$)$_m$—C=C—R$_5$, —(CH$_2$)$_m$—X—R$_6$, —(CH$_2$)$_m$—CH=CH—X—R$_6$, —(CH$_2$)$_m$—C≡C—X—R$_6$, in presence of esterifying agent to give corresponding compound of Formula XIa or XIb, wherein * is a chiral centre, and subjecting the resulting compound to one or more of the following reactions:

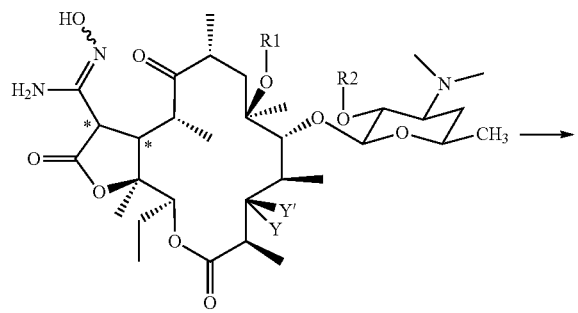

VIIa, Y' is H, Y is Ocladinose, R2, R2' is TES
VIIb, Y' is H, Y is OH, R2, is TES

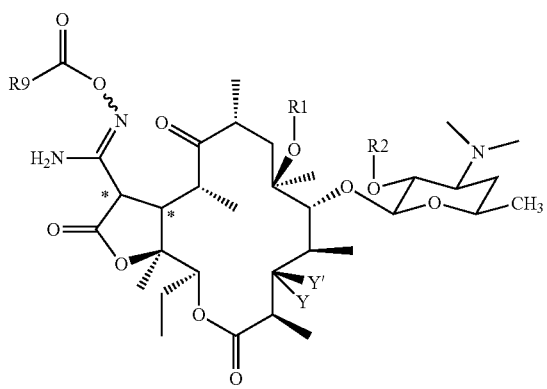

XIa, Y' is H, Y is Ocladinose, R2, R2' is TES
XIb, Y' is H, Y is OH, R2, is TES i) deprotecting the hydroxyl protecting groups of compound of Formula XIa to give the corresponding macrolide of Formula XIIa;

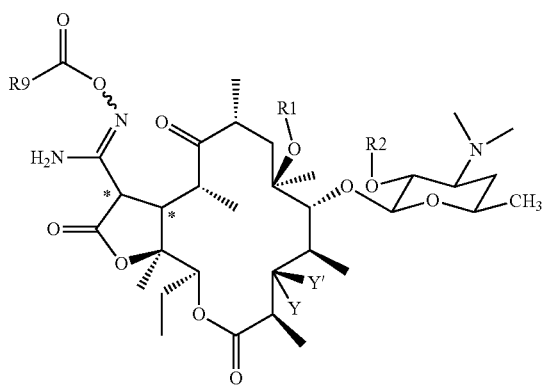

XIIa or ii) oxidizing the compound of Formula XIb to give the 3-ketone derivative of Formula XIII;

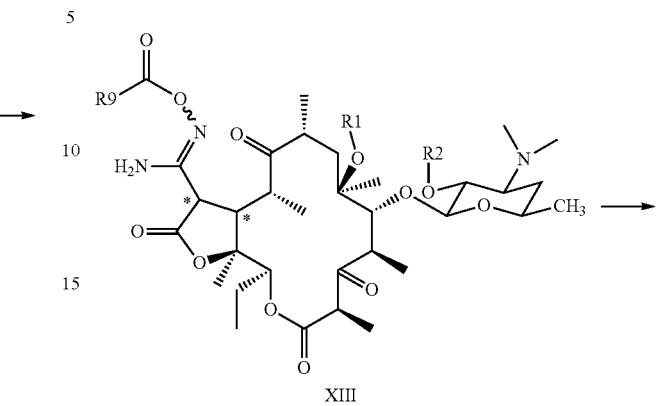

XIII

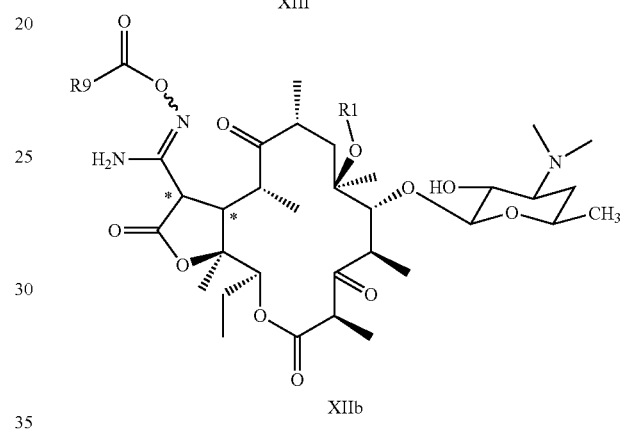

XIIb iii) deprotecting the hydroxyl protecting groups to give the corresponding ketolide of Formula XIIb;

b) treating the compound of Formula VIIa or VIIb with a suitable isocyanate reagent of Formula $R_9$—N=C=O, wherein $R_9$ represents —$(CH_2)_m$—$R_5$, —$(CH_2)_m$—CH=CH—$R_5$, —$(CH_2)_m$—C≡C—$R_5$, —$(CH_2)_m$—B—$R_5$, —$(CH_2)_m$—CH=CH—$R_5$, —$(CH_2)_m$—C≡C—$R_5$, —$(CH_2)_m$—X—$R_6$, —$(CH_2)_m$—CH=CH—X—$R_6$, —$(CH_2)_m$—C≡C—X—$R_6$, wherein $R_5$, $R_6$, X, B and m are as defined above, to give compound of Formula XIVa or XIVb, wherein * is a chiral centre, and subjecting the resulting compound to one or more of the following reactions:

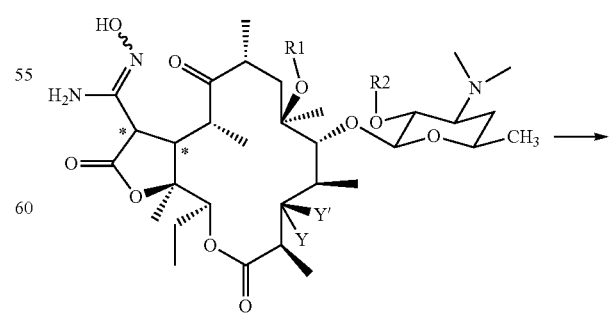

VIIa, Y' is H, Y is Ocladinose, $R_2$, $R_{2'}$ is TES
VIIb, Y' is H, Y is OH, $R_2$, is TES -continued

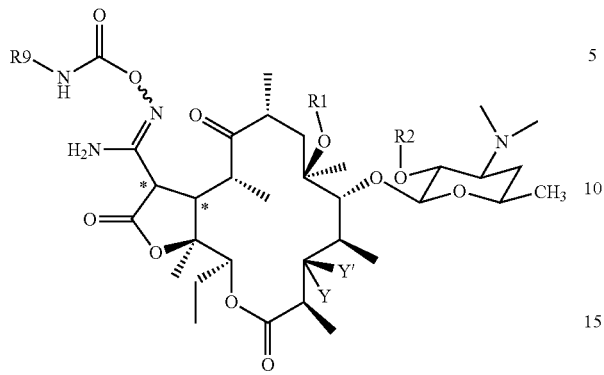

XIVa, Y' is H, Y is Ocladinose, R₂, R₂' is TES
XIVb, Y' is H, Y is OH, R₂, is TES i) deprotecting the hydroxyl protecting groups of compound of Formula XIVa to give the corresponding macrolide of Formula XVa;

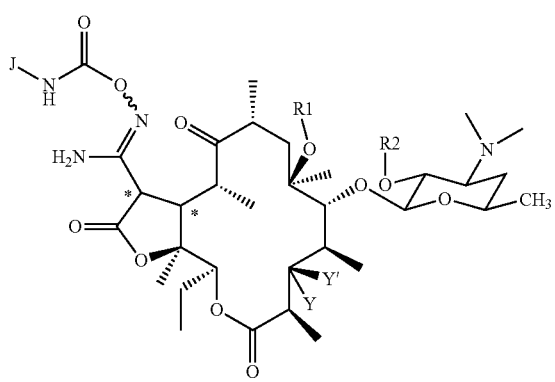

XVa or ii) converting the 3-hydroxyl derivative XIVb to 3-ketone derivative of Formula XVI;

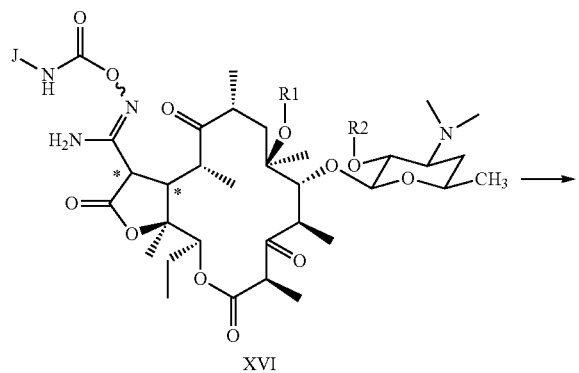

XVI

-continued

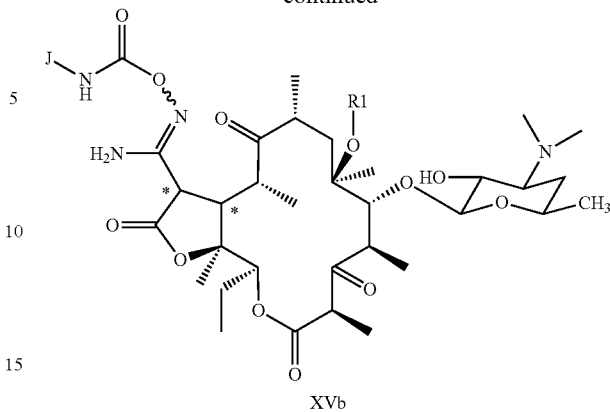

XVb iii) deprotecting the hydroxyl protecting groups of XVI to give the corresponding ketolide of Formula XVb;

c) treating the compound of Formula VIIa or VIIb with a suitable alkylating reagent of Formula halo-R₉, wherein R₉ represents —(CH₂)ₘ—R₅, —(CH₂)ₘ—CH=CH—R₅, —(CH₂)ₘ—C≡C—R₅, —(CH₂)ₘ—B—R₅, —(CH₂)ₘ—CH=CH—R₅, —(CH₂)ₘ—C≡C—R₅, —(CH₂)ₘ—X—R₆, —(CH₂)ₘ—CH=CH—X—R₆, —(CH₂)ₘ—C≡C—X—R₆, wherein B, X, R₅, R₆ and m are as defined above and halo is a chlorine, bromine or iodine, in presence of base to give compound of Formula XVIa or XVIb, wherein * is a chiral centre, and subjecting the resulting compound XVIa or XVIb, to one or more of the following reactions:

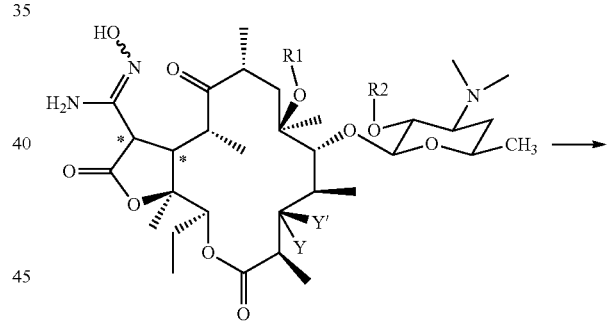

VIIa, Y' is H, Y is Ocladinose, R2, R2' is TES
VIIb, Y' is H, Y is OH, R2, is TES

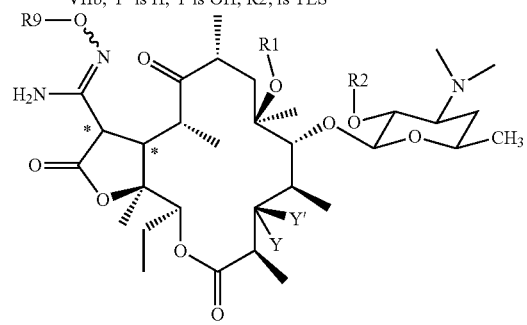

XVIa, Y' is H, Y is Ocladinose, R2, R2' is TES
XVIb, Y' is H, Y is OH, R2, is TES iv) deprotecting the hydroxyl protecting groups of Formula XVIa to give the corresponding macrolide of Formula XVIIa;

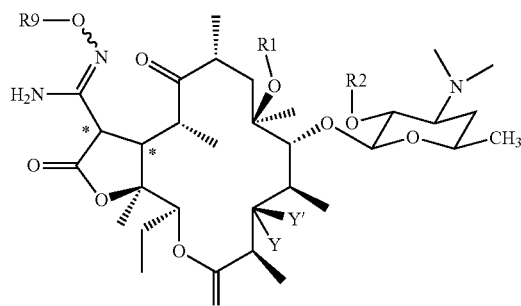

or v) converting the 3-hydroxyl derivative of Formula XVIa to 3-oxo derivative of Formula XVIIb';

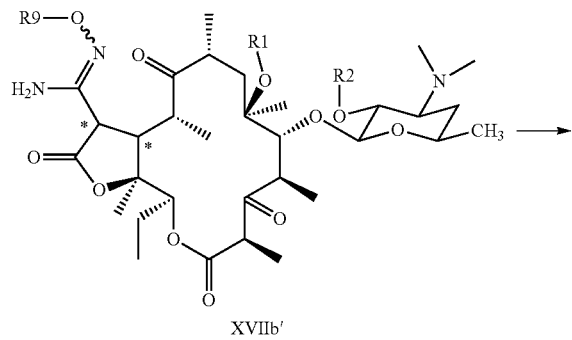

XVIIb'

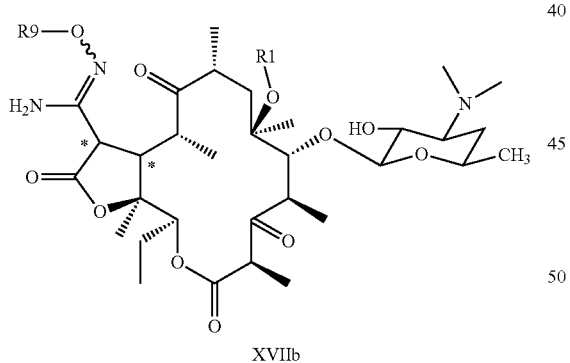

XVIIb iii) deprotecting the hydroxyl protecting groups of compound of Formula XVIIb' to give the corresponding ketolide of Formula XVIIb;

d) treating the compound of Formula XVIIIa or XVIIIb with a suitable halo-aryl reagent of Formula halo-$R_5$ or halo-X—$R_6$ in the presence of suitable palladium catalyst and phosphine derivative under heck coupling reaction conditions to give compound of Formula XIXa or XIXb,

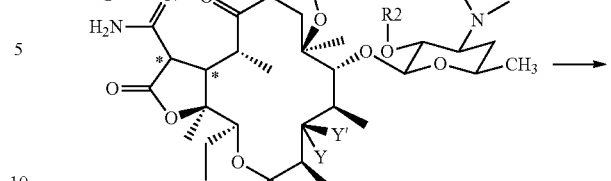

XVIIIa, Y' is H, Y is Ocladinose, R2, R2' is TES
XVIIIb, Y' is H, Y is OH, R2, is TES

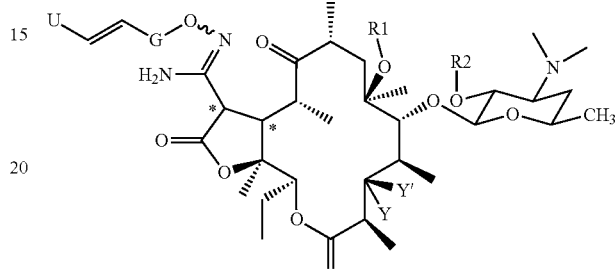

XIXa, Y' is H, Y is Ocladinose, R2, R2' is TES
XIXb, Y' is H, Y is OH, R2, is TES wherein G is —$(CH_2)_m$—, -A-$(CH_2)_m$—; U is —$R_5$, —X—$R_6$ and * is a chiral centre;

and subjecting the resulting compound to one or more of the following reactions:

i) deprotecting the hydroxyl protecting groups to give the corresponding macrolide of Formula XXa;

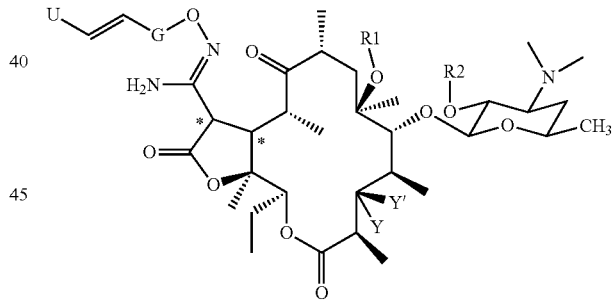

XXa or ii) converting the 3-hydroxyl derivative XIXb to 3-ketone of Formula XXb';

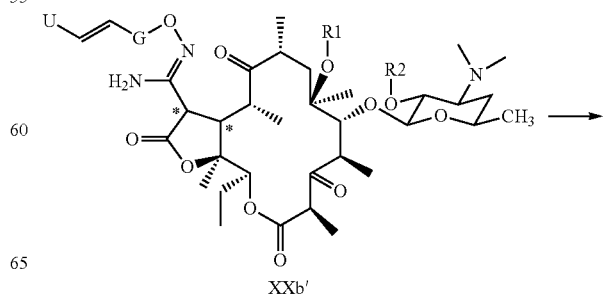

XXb'

115

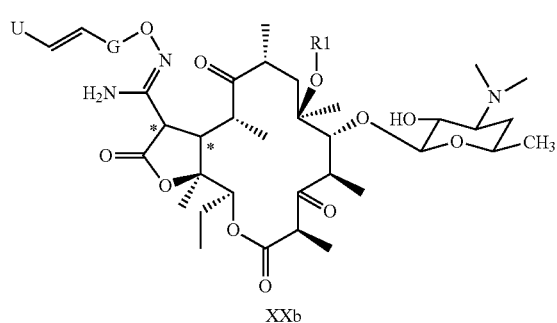

XXb iii) deprotecting the hydroxyl protecting groups of Formula XXb' to give the corresponding ketolide of Formula XXb;

e) treating the compound of Formula XXIa or XXIb with a suitable halo-aryl reagent in the presence of suitable palladium catalyst under sonagashira coupling reaction conditions to give corresponding compound of Formula XXIIa or XXIIb,

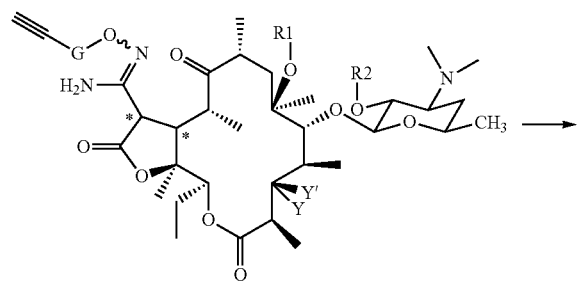

XXIa, Y' is H, Y is Ocladinose, R2, R2' is TES
XXIb, Y' is H, Y is OH, R2, is TES

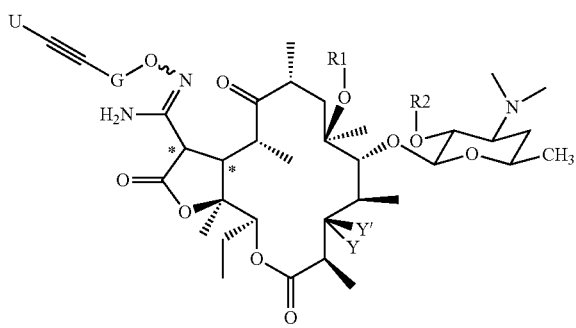

XXIIa, Y' is H, Y is Ocladinose, R2, R2' is TES
XXIIb, Y' is H, Y is OH, R2, is TES wherein G is —(CH$_2$)$_m$—, -A-(CH$_2$)$_m$—; U is —R$_5$, —X—R$_6$ and * is a chiral centre;

and subjecting the resulting compound of Formula XXIIa or XXIIb to one or more of the following reactions:

i) deprotecting the hydroxyl protecting groups to give the corresponding macrolide of Formula XXIIIa,

116

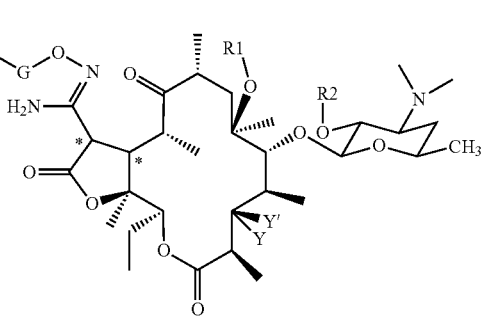

XXIIIa or ii) converting the 3-hydroxyl derivative of Formula XXIIb to 3-ketone derivative of Formula XXIV,

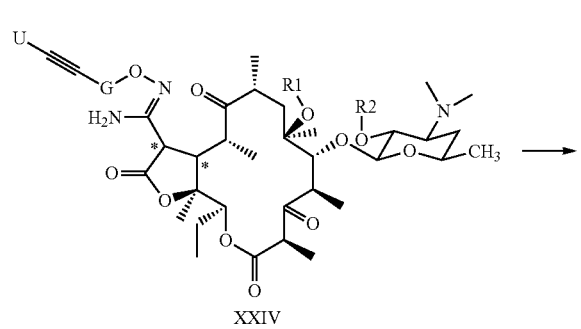

XXIV

XXIIIb iii) deprotecting the hydroxyl protecting groups of XXIV to give the corresponding ketolide of Formula XXIIIb;

f) Optionally, hydrogenating the compound obtained by any of the above steps to obtain the corresponding saturated compound.

17. The process of claim 16, wherein the process of preparation of compound of Formula VII, comprises treating a compound of Formula VI with hydroxylamine in a suitable solvent

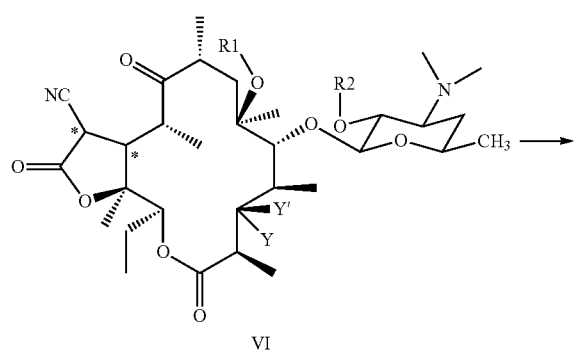

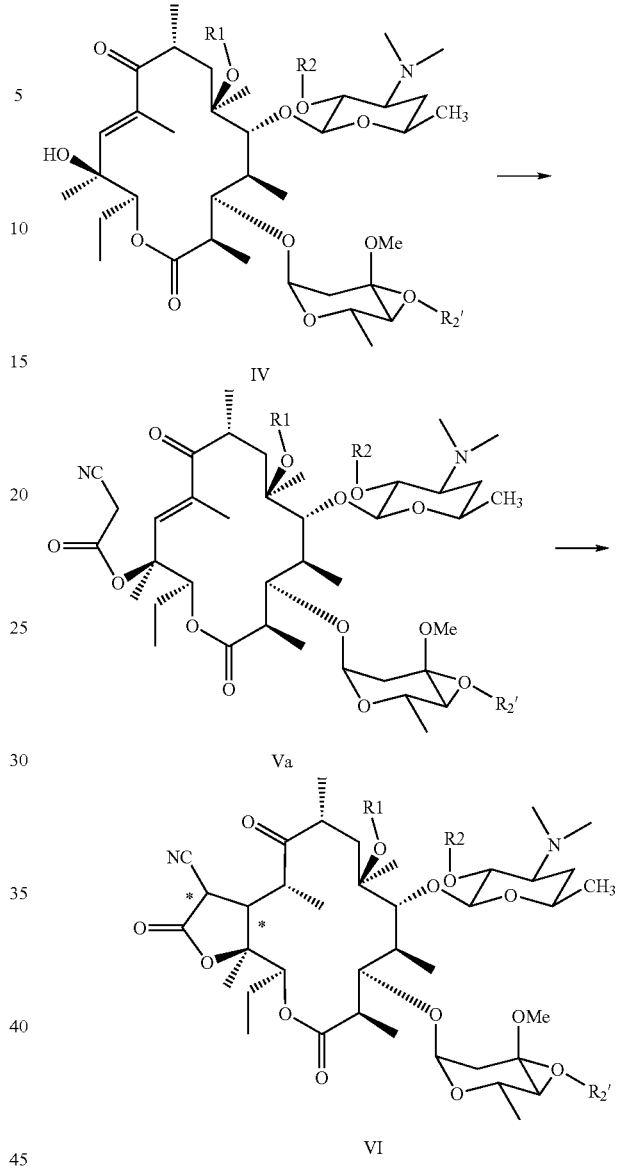

wherein:

R₁ is hydrogen or methyl;

R₂ is hydrogen or hydroxyl protecting group, wherein hydroxyl protecting groups are selected from the group consisting of triethylsilyl, trimethylsilyl, acetyl, benzoyl, methoxymethyl, benzyl, methoxyethoxymethyl or tertbutyldimethylsilyl; and Y' is hydrogen and Y is OR₇ wherein R₇ is hydrogen or

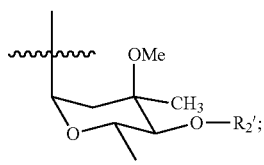

wherein R₂' is hydrogen, (when R₂' is hydrogen, R₇ is designated as cladinose) or hydroxyl protecting group, wherein hydroxyl protecting groups are selected from the group consisting of triethylsilyl, trimethylsilyl, acetyl, benzoyl, methoxymethyl, methoxyethoxymethyl, benzyl or tertbutyldimethylsilyl; or Y and Y' together with the carbon to which they are attached form C=O.

18. The process of claim 17, wherein the process of preparation of compound of Formula VI comprises the steps of:

a) treating a compound of Formula IV with cyanoacetic acid in presence of a base to give compound of Formula Va b) treating the compound of Formula Va with a base to give compound of Formula VI wherein:

R₁ is hydrogen or methyl;

R₂ is hydrogen or hydroxyl protecting group, wherein hydroxyl protecting groups are selected from the group consisting of triethylsilyl, trimethylsilyl, acetyl, benzoyl, methoxymethyl, benzyl, methoxyethoxymethyl or tertbutyldimethylsilyl; and wherein R₂' is hydrogen, (when R₂' is hydrogen R₇ is designated as cladinose) or hydroxyl protecting group, wherein hydroxyl protecting groups are selected from the group consisting of triethylsilyl, trimethylsilyl, acetyl, benzoyl, methoxymethyl, methoxyethoxymethyl, benzyl or tertbutyldimethylsilyl.

* * * * *